United States Patent [19]

Karasawa et al.

[11] Patent Number: 5,575,756
[45] Date of Patent: Nov. 19, 1996

[54] ENDOSCOPE APPARATUS

[75] Inventors: Hitoshi Karasawa; Norio Kobayashi, both of Hachioji; Tatsuya Yamaguchi, Hino; Tetsumaru Kubota, Hachioji; Yukio Kawase, Tokyo; Mitsumasa Okada; Takao Yamaguchi, both of Hachioji, all of Japan

[73] Assignee: Olympus Optical Co., Ltd., Tokyo, Japan

[21] Appl. No.: 289,226

[22] Filed: Aug. 12, 1994

[30] Foreign Application Priority Data

| Aug. 16, 1993 | [JP] | Japan | 5-202335 |
| Oct. 4, 1993 | [JP] | Japan | 5-248173 |
| Oct. 8, 1993 | [JP] | Japan | 5-253286 |
| Apr. 5, 1994 | [JP] | Japan | 6-066905 |

[51] Int. Cl.⁶ ........................ A61B 1/12
[52] U.S. Cl. ............ 600/157; 600/123; 600/156; 600/121
[58] Field of Search ................. 600/121, 123, 600/125, 153, 155, 156, 157, 158

[56] References Cited

U.S. PATENT DOCUMENTS

| 4,860,731 | 8/1989 | Matsuura . |
| 5,207,213 | 5/1993 | Auhll et al. . |
| 5,313,934 | 5/1994 | Wiita et al. ................. 600/157 X |
| 5,400,767 | 3/1995 | Murdolh .................... 128/4 |
| 5,419,309 | 5/1995 | Biehl ........................ 128/4 |

FOREIGN PATENT DOCUMENTS

| 57-42802 | 3/1982 | Japan . |
| 57-187504 | 11/1982 | Japan . |
| 60-142835 | 7/1985 | Japan . |
| 62-30766 | 7/1987 | Japan . |
| 64-884 | 1/1989 | Japan . |
| 64-83241 | 3/1989 | Japan . |
| 1-50406 | 10/1989 | Japan . |
| 2-7522 | 2/1990 | Japan . |
| 2-131714 | 11/1990 | Japan . |
| 5-11841 | 3/1993 | Japan . |
| 5-103749 | 4/1993 | Japan . |
| WO92/2074 | 11/1992 | WIPO . |
| 9405200 | 3/1994 | WIPO .................. 600/156 |

*Primary Examiner*—Stephen R. Crow
*Assistant Examiner*—Beverly M. Flanagan
*Attorney, Agent, or Firm*—Armstrong, Westerman, Hattori, McLeland & Naughton

[57] ABSTRACT

An endoscope apparatus includes: an endoscope having an insertion section; and a sheath attached thereto so as to cover at least the insertion section of the endoscope, wherein the endoscope apparatus is equipped with: a forward end gap portion formed between the inner surface of an edge portion formed in the forward end portion of the sheath and the outer surface of the forward end portion of the insertion section of the endoscope; and a fluid passage which communicates with the forward end gap portion and which is formed between the inner surface of the sheath and the outer surface of the insertion section of the endoscope, and wherein a liquid feeding passage or a suction passage for passing a cleaning fluid or a sucked object is provided in the fluid passage, and a nozzle section for spraying the cleaning fluid onto an observation window portion in the forward end portion of the insertion section of the endoscope is provided in the forward end gap portion.

13 Claims, 33 Drawing Sheets

FIG.21(a) FIG.21(b) FIG.21(c)
FIG.22
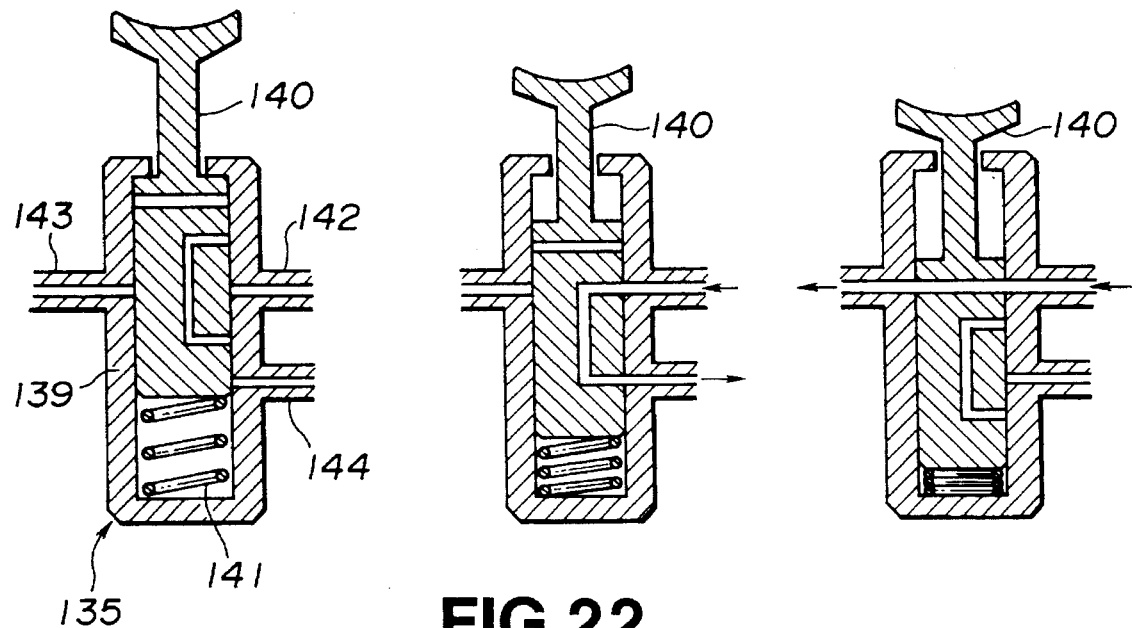
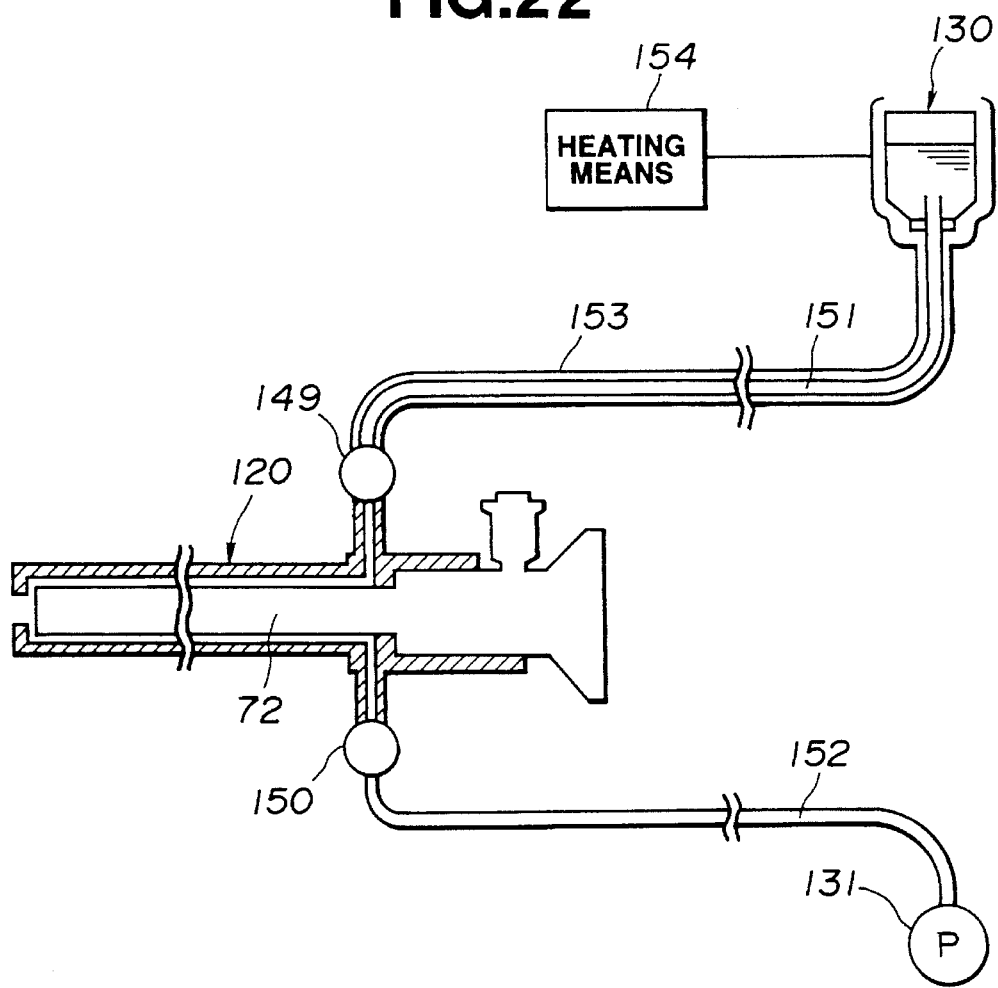

FIG.28
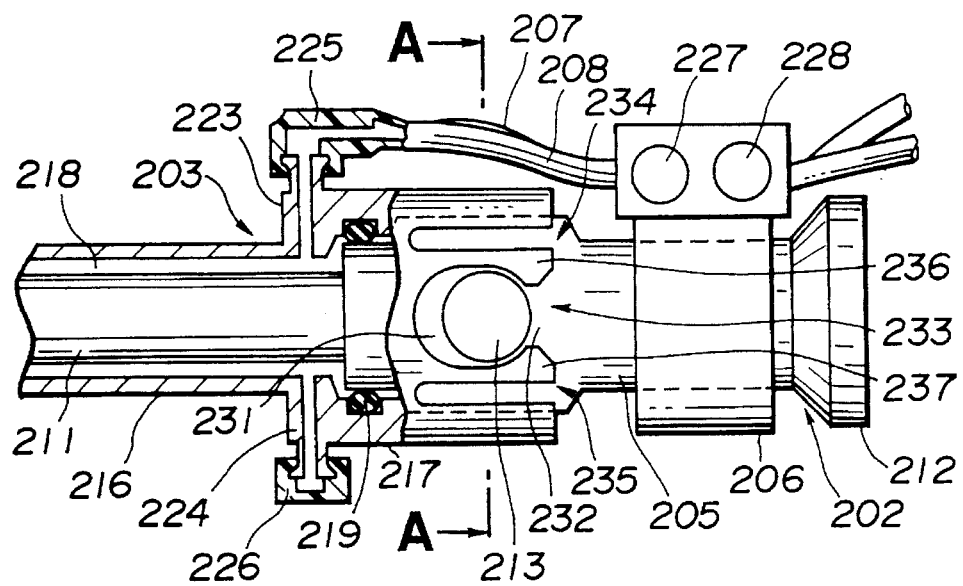
FIG.29
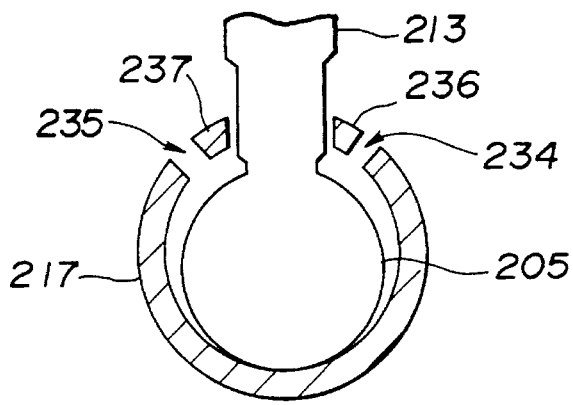
FIG.30(a)     FIG.30(b)
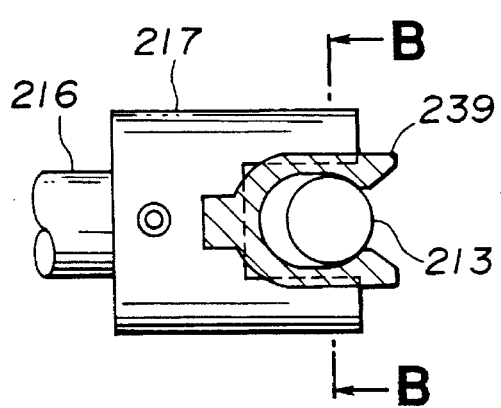     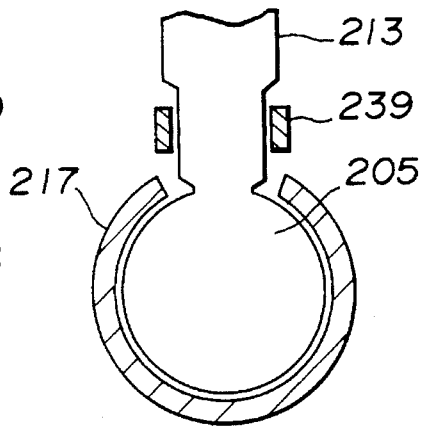

FIG.52(b) FIG.52(a)
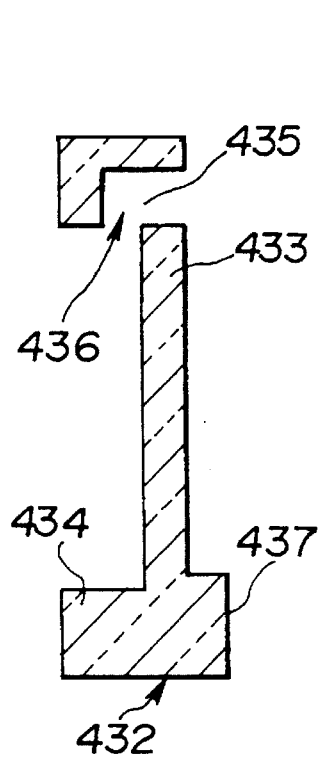
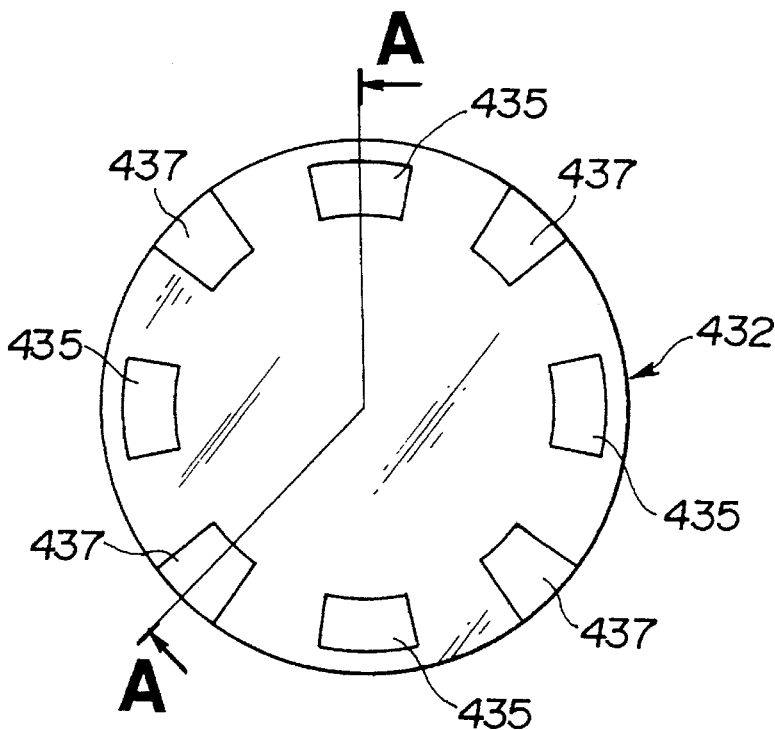
FIG.53
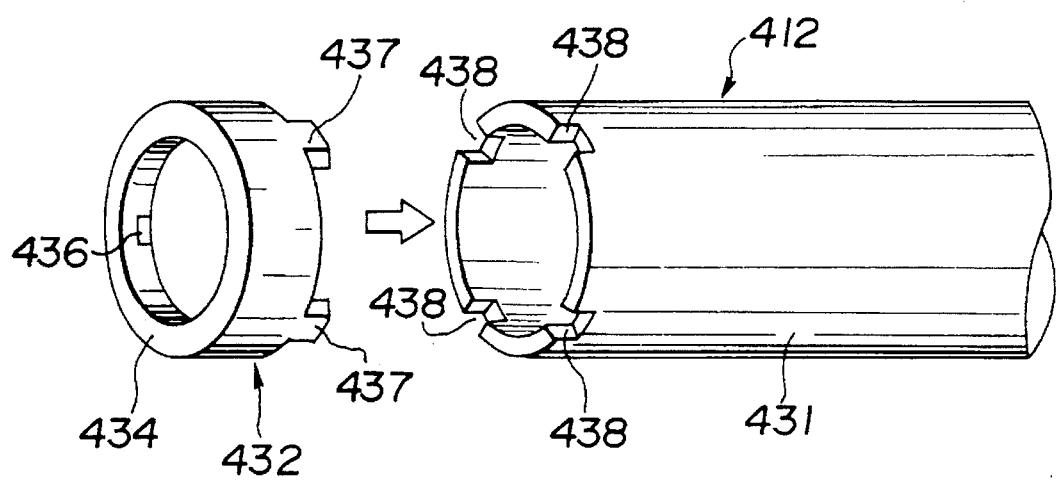

ENDOSCOPE APPARATUS

BACKGROUND OF THE INVENTION

1. Field of the Invention

The present invention relates to an endoscope apparatus which performs observation and therapeutic procedure within a body cavity and, more particularly, to an endoscope apparatus which is provided with cleaning means for performing feed liquid, feed gas, suction or the like with respect to a view window portion at a forward-end part or a distal part of an insertion section of the endoscope apparatus, to maintain a superior field of view.

2. Description of Related Art

At present, various kinds of endoscopes for performing observation and therapeutics procedure within a body cavity or the like have been used in various kinds of fields such as a medical treatment or the like. There are many cases where such endoscopes are used under environments in which inserting sections or distal parts thereof are apt to become dirty. A view window which is provided in the distal part of the endoscope must particularly be kept always clean, in order to produce a superior field of view.

In view of the above, a prior art endoscope is provided, for example, with, as cleaning means, means in which a flow passage for passing fluid such as water or the like for cleaning is provided, and a nozzle which is in communication with the flow passage is provided at a distal part, for blowing the cleaning fluid against a viewing window at the distal part of an inserting section, feed liquid of the cleaning fluid is performed toward the viewing window to wash away dirt and dulling or hazing, or feed gas is performed to the observation window to remove remaining water drops. Further, there is also a case where, as the cleaning means, the endoscope is provided with means, in addition to the feed water means to the observation window, in which a suction passage is provided to suck the dirt and the water drops remaining in the vicinity of the observation window.

As the endoscope apparatus which is provided with the cleaning means for performing feed liquid, feed gas, suction or the like with respect to the observation window at the distal part of the insertion section, an arrangement in which the passage or a nozzle is provided at the insertion section of an endoscope body is general. However, as an arrangement in which a sheath is detachably covered on the inserting section of the endoscope, an arrangement or the like has been proposed in which the passage or the nozzle is provided in the sheath.

With the arrangement of the endoscope apparatus which is provided with the prior art cleaning means as described above, the cleaning passage or nozzle is provided in the sheath which covers the endoscope body or the endoscope. For this reason, there have been cases where the apparatus arrangement complicates assembly of a line tube and a nozzle; formation of the nozzle which is provided at the distal part has been particularly difficult, and formation of the cleaning passage and the nozzle has been difficult so that much labors have been required. Accordingly, the following problems have been generated. That is, the arrangement of the cleaning means becomes expensive, with increased time consumption during operation upon assembling.

Moreover, there are the following problems. That is, for the arrangement in which the cleaning passage and nozzle are provided in the endoscope body or in the sheath as is in the prior art, since an elongated line and a nozzle whose shape or form is narrow and is complicated are assembled with the endoscope body or the sheath, it is difficult to wash or clean a portion of the line or the nozzle when washing or cleaning is performed after use of the endoscope during inspection or examination so that much time is consumed for cleaning and disinfection or sterilization.

Furthermore, in recent years, as an arrangement of a disposable or throwaway type in which a treatment tool or the like is cancelled without being washed or cleaned after use, a medical harness has been put to practical use in which a new sterilized arrangement is used during every use, and time spent in cleaning or the like is reduced so that therapeutics procedure and examination can efficiently be performed while easily keeping a clean state or condition.

For example, in the situation where an endoscope in which an inserting section which is used during insertion into a peritoneal cavity or the like in a patient to perform observation is difficult to adapt to a disposable type, since a complicated arrangement including a hard mirror as in the prior art is expensive, it is impossible to apply the endoscope to the disposable type as it is. Particularly, in case where the aforementioned cleaning means is added, the arrangement or structure is further complicated. In order to arrange the hard endoscope provided with the cleaning means, at a low cost, so as to be disposable, it is necessary that the number of parts is reduced as much as possible, while improving ease of assembly.

SUMMARY OF THE INVENTION

An object of the present invention is to provide an endoscope apparatus of the type which is provided with a cleaning means for cleaning a view window at a forward-end part of the endoscope apparatus to ensure a satisfactory viewing field, wherein a passage or nozzle for cleaning can be easily formed in a simple structure.

Another object of the present invention is to provide an endoscope apparatus in which the passage or nozzle for cleaning can be easily formed solely by combining the endoscope insertion section with a sheath for covering the insertion section.

Still another object of the present invention is to provide an endoscope apparatus in which it is possible to form a passage or nozzle for at low costs and in a simple structure without having to provide a line tube or nozzle having a thin and narrow and complicated structure for the purpose of cleaning the forward-end part of the endoscope, thereby enabling the endoscope insertion section, etc. to be easily cleaned and disinfected.

A further object of the present invention is to provide an endoscope apparatus of the type which is provided with a cleaning means, wherein the endoscope apparatus has a relatively low price, a satisfactory assembling performance, and a structure of a throwaway type that is disposable after use.

In accordance with the present invention, there is provided an endoscope apparatus comprising an endoscope including an insertion section, and a sheath attached thereto so as to cover at least the this insertion section, wherein the endoscope apparatus is equipped with: a forward end gap portion formed between an inner surface of an edge portion formed in a forward end portion of the sheath and an outer surface of a forward end portion of the insertion section of the endoscope; and a fluid passage which communicates with the forward end gap portion and which is formed between an inner surface of the sheath and an outer surface of the insertion section of the endoscope.

Other features and advantages of the present invention will become apparent from the following description.

BRIEF DESCRIPTION OF THE DRAWINGS

FIG. 2 is an enlarged explanatory view of a distal part of insertion section of an endoscope according to the first embodiment;

FIG. 3 is an explanatory view of the inserting section of the endoscope which is viewed from the side of the distal part of the endoscope according to the first embodiment;

FIG. 9(b) is a cross-sectional view taken along a line B—B in FIG. 8;

FIG. 9(c) is a cross-sectional view taken along a line C—C in FIG. 8;

FIG. 12(b) is a cross-sectional view taken along a line B—B in FIG. 11;

FIG. 12(c) is a cross-sectional view taken along a line C—C in FIG. 11;

FIG. 14 is a cross-sectional explanatory view of the sheath inserting section under a state in which the endoscope is not inserted;

FIG. 17(b) is a cross-sectional view taken along a line B—B in FIG. 16;

FIG. 17(c) is a cross-sectional view taken along a line C—C in FIG. 16;

FIG. 18 is a cross-sectional view taken along a line D—D in FIG. 17(b);

FIGS. 21(a), 21(b) and 21(c) are explanatory views showing an arrangement of a three-way activity plug;

FIG. 22 is an arrangement explanatory view showing a second arrangement example of a cleaning mechanism;

FIG. 25 is an arrangement explanatory view showing a whole arrangement of the lens-blur preventing means including the light source device;

FIGS. 27 to 37 relate to a seventh embodiment of the invention, FIG. 27 being a whole arrangement view of an endoscope apparatus;

FIG. 28 is a cross-sectional view showing an arrangement in the vicinity of a sheath body;

FIG. 29 is a cross-sectional view taken along a line A—A in FIG. 28;

FIG. 30(a) is a top plan view showing a modification of a sheath mounting structure or arrangement which is different from that in FIG. 28;

FIG. 30(b) is an enlarged cross-sectional view taken along a line B—B in FIG. 30(a);

FIG. 31 is a top plan view of a sheath body;

FIG. 32 is a view as viewed from a direction C in FIG. 31;

FIG. 33 is a perspective view showing a valve unit;

FIG. 35 is a cross-sectional view showing an arrangement of a valve unit;

FIG. 36 is an enlarged cross-sectional view taken along a line D—D in FIG. 35;

FIG. 37 is an enlarged cross-sectional view taken along a line E—E in FIG. 35;

FIG. 40(*b*) is a cross-sectional view in an axial direction;

FIG. 52(*a*) is a rear view of a forward-end cover member in the endoscope apparatus according to the tenth embodiment;

FIG. 52(*b*) is a cross-sectional view taken along a line A—A in FIG. 52(*a*);

FIG. 53 is an exploded perspective view showing a pipe member for sheath and a forward-end cover member in the endoscope apparatus according to the tenth embodiment;

FIG. 54(*b*) is a front elevation view of a transparent plate according to the eleventh embodiment of the invention;

FIG. 59(*b*) is a view in which a transparent plate according to the thirteenth embodiment is viewed from the front;

FIG. 60(*b*) is a perspective view of a cover member according to the fourteenth embodiment;

FIG. 61(*b*) is a cross-sectional view of the distal part of the endoscope apparatus shown in FIG. 61(*a*);

DETAILED DESCRIPTION OF THE PREFERRED EMBODIMENTS

Figure 1:
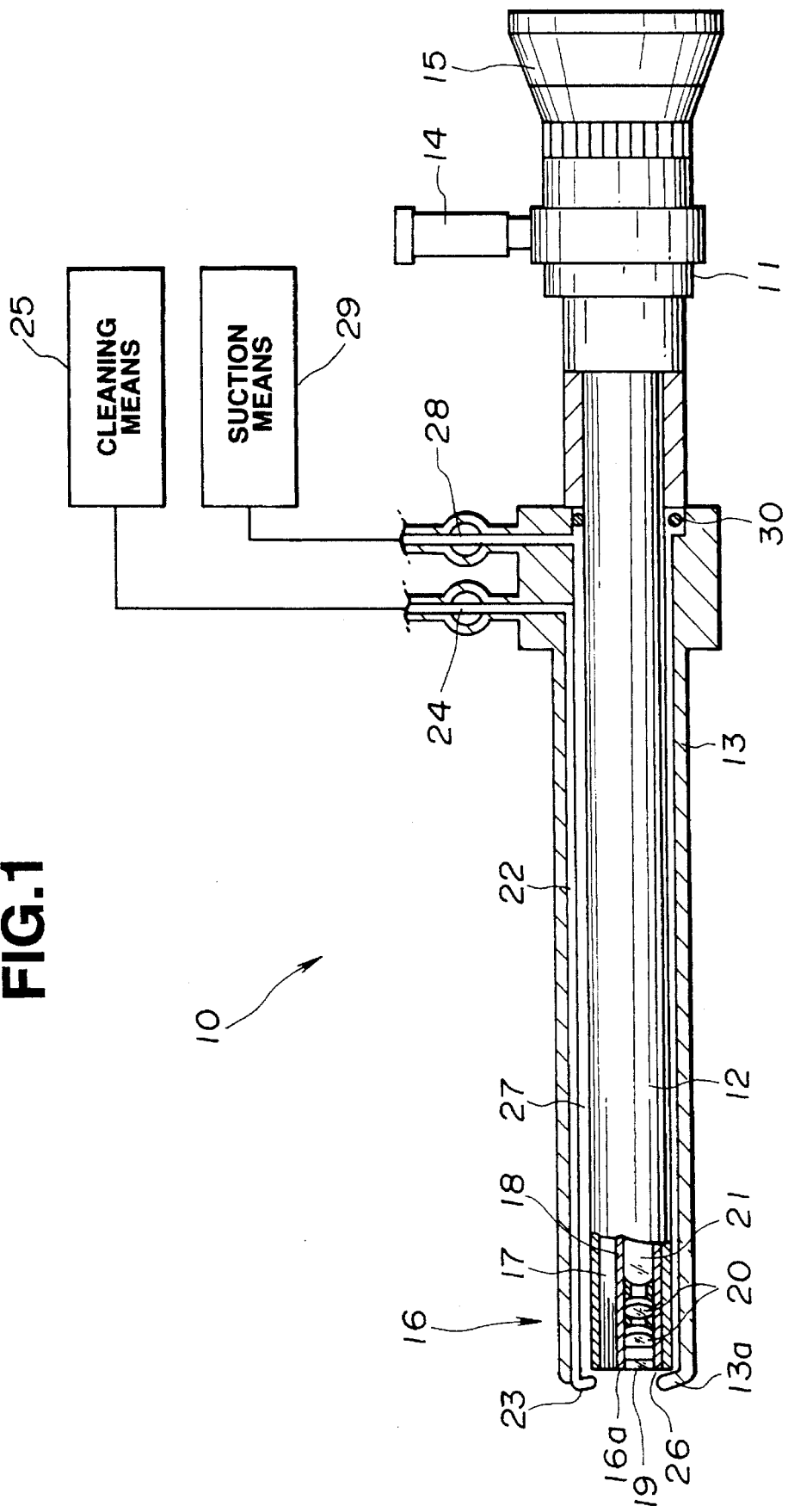
FIGS. 1 to 3 relate to a first embodiment of the invention, FIG. 1 being a schematic arrangement explanatory view of a whole endoscope apparatus.
Figure 2:
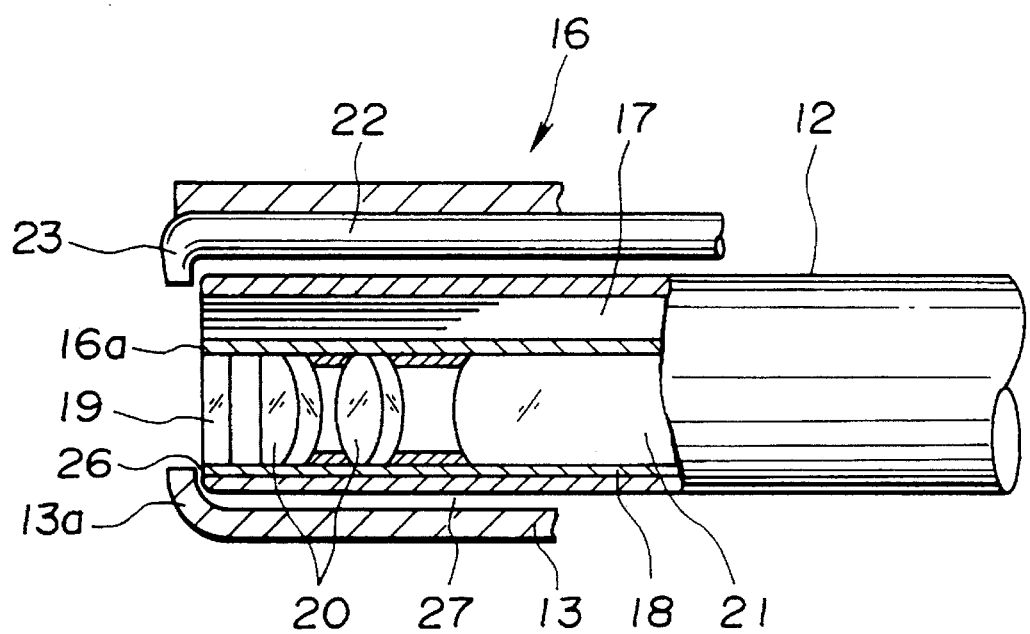
Figure 3:
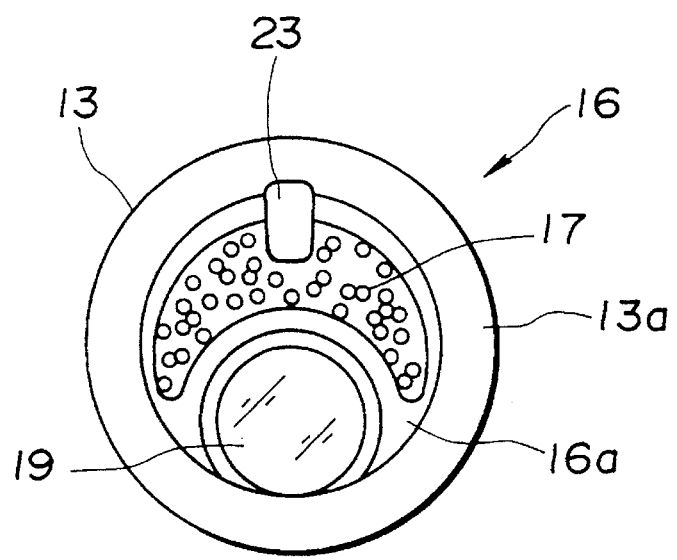

FIGS. 1 to 3 show a first embodiment of the invention. In this connection, FIG. 1 is a view showing a schematic arrangement of a whole endoscope apparatus, and FIG. 2 is a view showing, in enlargement, a distal part of an insertion section of the endoscope illustrated in FIG. 1, while FIG. 3 is a view in which the inserting section of the endoscope is viewed from the side of a forward end.

In these figures, the reference numeral 10 denotes the endoscope. The elongated inserting section 12 extends forwardly from an operating unit 11 of the endoscope 10. The insertion section 12 of the endoscope is inserted into a sheath 13. Further, a light guide base 14 is provided on a side surface of the outer periphery of the operating unit 11. An eyepiece 15 is provided in rear of the operating unit 11.

An light emission end surface of the light guide 17 is arranged at a forward-end surface 16*a* of the distal part 16 of the endoscope inserting section 12. The light guide 17 is adapted to be inserted through the endoscope inserting section 12, the operating unit 11, the light guide base 14 and a light guide cable (not shown), and to be led to a light source device (not shown), to transmit a light from the light source device to the forward end of the endoscope.

Moreover, a lens tube 18 is inserted into the endoscope inserting section 12 so that a surface of a cover glass 19 which blocks the lens tube 18 is exposed at the forward-end surface 16*a* of the distal part 16 of the endoscope inserting section. An objective lens system 20 and a relay optical system 21 are arranged in rear of the cover glass 19. An optical image which is formed by the objective lens system 20 is transmitted, by the relay optical system 21, to the eyepiece unit 15 through the operating unit 11.

Meanwhile, the sheath 13 is provided with a feed water channel 22 for leading cleaning liquid (water or the like) to a forward end of the sheath 13 from a Grip for an operator. The side of the forward end of the feed water channel 22 is provided with a nozzle 23 for blowing the cleaning liquid to the cover glass 19. The Grip for the operator of the feed water channel 22 is in communication with the feed water line 24 which is formed in the sheath 13. Furthermore, cleaning means 25 for feeding the cleaning liquid (water or the like) out is connected to the other end of the feed water line 24.

Further, the sheath 13 has a forward end thereof which is formed, on an inner side thereof, with an edge 13*a*. Under a state or condition in which the endoscope insertion section 12 is inserted into the sheath 13, a slight Gap, or a forward-end clearance 26 is defined between the inner surface of the edge 13a ad the forward-end surface 16a of the endoscope insertion section 12. The edge 13a is formed into such a predetermined dimension or size as not to narrow a field of view of visual field of observation due to the endoscope 10 (to block the upper portion of the cover glass 19, or the like).

Moreover, a slight gap, or an insertion-section clearance 27 is defined between the inner surface of the sheath 13 and the endoscope insertion section 12. The insertion clearance 27 is in communication with the forward-end clearance 26 at the side of the forward end, and is in communication with the suction line 28 formed in the sheath 13, on the grip of the operator. Furthermore, suction means 29 is connected to the other end of the suction line 28.

Further, an O-ring 30 is provided on the side of the grip of the operator, further from a portion at which the insertion-section clearance 27 and the suction passage 29 are in communication with each other so that air tightness at the side of the grip of the operator of the insertion- section clearance 27 is maintained.

Subsequently, operation of the embodiment which is arranged as described above will be described.

First, in case where an affected or diseased part in the body cavity or the like is observed by the endoscope 10 which is inserted into the body cavity, a white light from the light source device (not shown) is transmitted through the light guide 17, and is outputted toward an objective part, from an outputting end surface of the light guide 17 which is arranged at the forward-end surface 16a of the distal part 16 of the endoscope inserting section 12.

An image is transmitted to the operating unit 11 through the cover glass 19 by the objective lens system 20 and the relay optical system 21 so that there can be provided an observation image from the eyepiece 15.

Subsequently, in case where dirt or the like is adhered to a surface or the like of the cover glass 19 so that cleaning is performed to remove the dirt or the like, the cleaning water is blown, by the cleaning means 25, against the cover glass 19 from the nozzle 23, through the feed water line 24 and the feed water channel 22 which are provided in the sheath 13.

Subsequently, water drops or the like which remain on the surface of the cover glass 19 or the like are sucked by the suction means 29, through the suction line 28, the insertion-section clearance 27 between the inner surface of the sheath 13 and the endoscope insertion section 12 and the forward-end clearance 26 between the inner surface of the edge 13a on the inside of the forward end of the sheath 13 and the forward end surface 16a of the inserting section of the endoscope.

Here, since the edge 13a is provided on the inside of the forward end of the sheath 13, it is possible to perform suction in which a suction force is directed to the direction of the cover glass 19 reliably and substantially from the overall periphery, and which is strong and has no nonuniformity.

Moreover, not only the water drops or the like which remain on the surface of the cover glass 19 or the like, but also water drops or the like which remain on the forward-end surface 16a of the endoscope insertion section such as, for example, the outputting end surface of the light guide 17 or the like can be sucked by the suction, it is possible to always maintain the outputting light quantity superior.

Furthermore, even for or in the endoscope of the prior art arrangement, it is possible to use the sheath for the endoscope according to the embodiment to improve the suction effects. Thus, it is possible to sufficiently cope with aftermarket.

The arrangement of the embodiment is such that, under a state in which the sheath is covered on the inserting section of the endoscope, a flow passage for suction is defined by the forward-end clearance defined between the inner surface of the edge formed on the inside of the forward end of the sheath and the forward-end surface of the endoscope inserting section, and the insertion-portion clearance which is in communication with the forward-end clearance and which is defined between the inner surface of the sheath and the outer surface of the endoscope insertion section. At this time, the forward-end clearance serves as a nozzle, and the insertion-section clearance serves as the suction line. For this reason, only combination of the endoscope inserting section and the sheath enables the cleaning fluid passage to be formed easily.

Further, in case of this arrangement, combination of the endoscope insertion section and the sheath first forms the cleaning fluid passage. If the endoscope insertion section and the sheath are disassembled from each other, the fluid line is divided and is exposed. Accordingly, there is no fear that the suction line is clogged by filth or dirt or the like. Moreover, it is possible to easily perform also cleaning and disinfection of the endoscope and the sheath. Thus, it is possible to keep or maintain them clean. The sheath may be of a throwaway type which is to be disposed of after use and replaced by a new one.

By the cleaning fluid line formed in this manner, it is possible to perfectly remove the feed water droplets at the forward end of the endoscope insertion section. Thus, it is possible to secure a superior observation field of view.

Subsequently, a second embodiment of the invention will be described with reference to FIGS. 4 and 5. The second embodiment is also arranged substantially similarly to the aforesaid first embodiment. However, the second embodiment is different from the first embodiment in that the arrangement relating to the cleaning is provided on the side of the endoscope body, not on the side of the sheath.

In connection with this, the description of constitutional portions the same as those of the first embodiment will be omitted.

Figure 4:
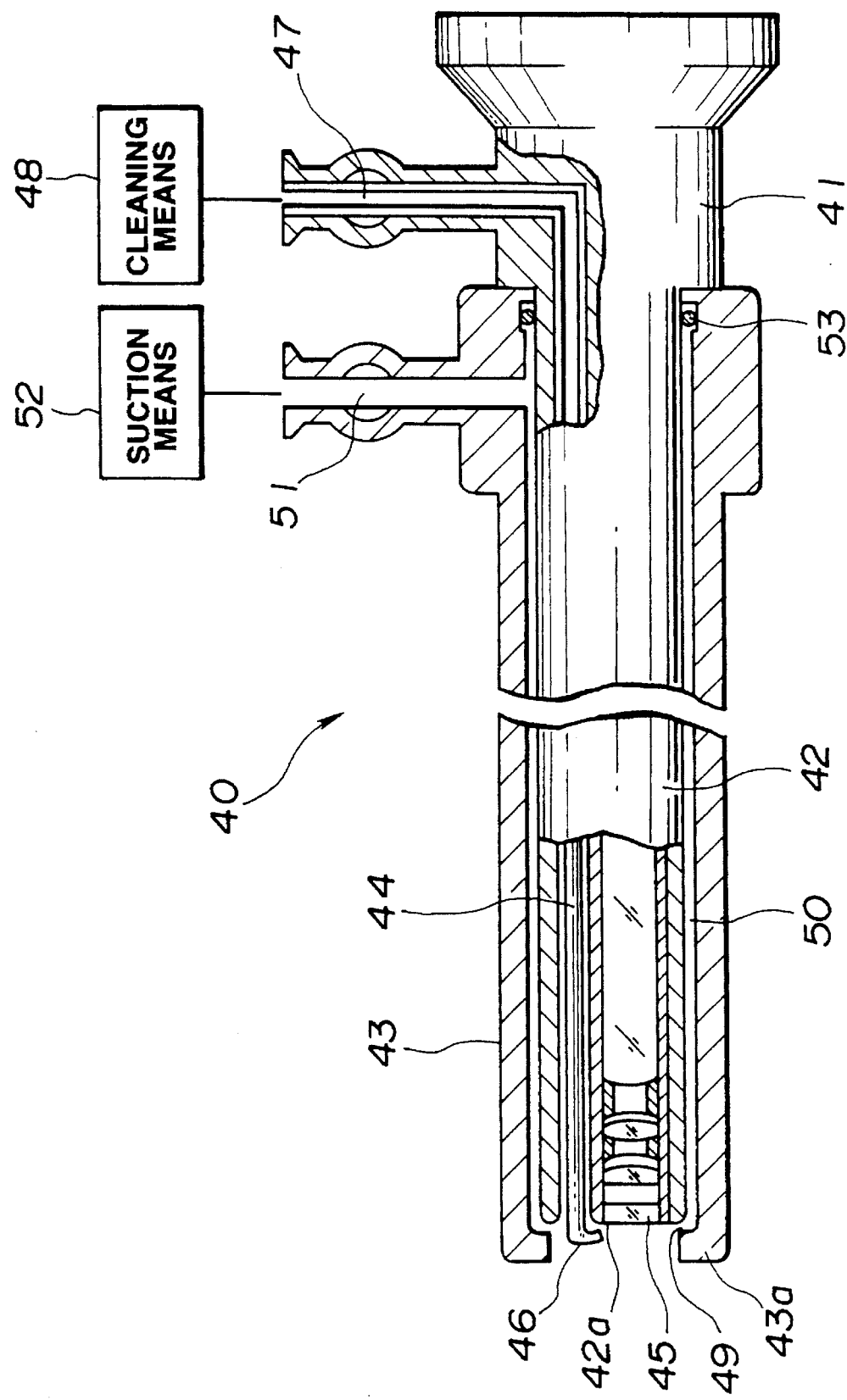
FIG. 4 is a schematic arrangement explanatory view of a whole endoscope apparatus according to a second embodiment of the invention.
Figure 5:
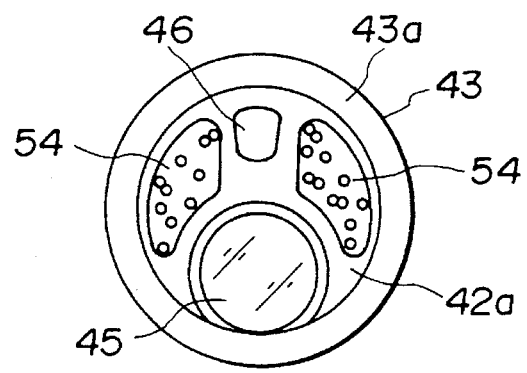
FIG. 5 is an explanatory view of the inserting section of the endoscope which is viewed from the side of the distal part of the endoscope according to the second embodiment.

Specifically, as shown in FIGS. 4 and 5, an elongated inserting section 42 extends forwardly from an operating unit 41 of an endoscope 40. The endoscope inserting section 42 is inserted into a sheath 43.

The endoscope inserting section 42 is provided therein with a feed water channel 44 for leading cleaning liquid (water or the like) from a grip for an operator to a forward end of the endoscope insertion section 42. A nozzle 46 for blowing the cleaning liquid against the cover glass 45 is provided on the side of the forward end of the feed water channel. The grip for the operator of the feed water channel 44 is in communication with a feed water line 47 which is provided in the operating unit 41. Further, cleaning means 48 for feeding the cleaning liquid (water or the like) out is connected to the other end of the water feed line 47.

Moreover, the forward end of the sheath 43 is formed, on the inside thereof, with an edge 43a. Under a condition in which the endoscope inserting section 42 is inserted into the sheath 43, a slight gap, that is, a forward-end clearance 49 is defined between an inner surface of the edge 43a and a forward-end surface 42a of the endoscope insertion section 42. The edge 43a is formed to such a predetermined size as not to narrow the field of view of observation due to the endoscope 40 (to block the upper portion of the cover glass 45, or the like).

Furthermore, a slight gap, that is, an insertion-section clearance 50 is defined between the inner surface of the sheath 43 and the endoscope inserting section 42. The insertion-section clearance 50 is, on the side of a forward end, in communication with the forward-end clearance 49, and is, on the side of a grip for an operator, in communication with a suction line 51 formed in the sheath 43. Further, suction means 52 is connected to the other end of the suction line 51.

Moreover, an O-ring 53 is provided on the grip for the operator further from the portion at which the insertion-section clearance 50 and the suction line 51 are in communication with each other so that air tightness is maintained at the grip for the operator of the insertion- section clearance 50.

In connection with the above, the reference numeral 54 in FIG. 5 denotes a light guide. In the endoscope apparatus arranged as described above, in case where the cover glass 45 at the forward end of the endoscope inserting section 42 is cleaned, the cleaning water is blown, by the cleaning means, against the cover glass 45 from the nozzle 46 through the water feed line 47 and the water feed channel 44.

Subsequently, water drops or the like remaining on the cover glass 45 are sucked by the suction means 52, through the suction line 51, the insertion-section clearance 50 between the inner surface of the sheath 43 and the endoscope inserting section 42 and the forward-end clearance 49 between the inner surface of the edge 43a on the inside of the forward end of the sheath 43 and the forward-end surface 42a of the endoscope inserting section.

In this manner, according to the embodiment, since the arrangement relating to the cleaning is provided on the side of the endoscope body, it is possible to simplify and small-size the arrangement or structure of the sheath.

Subsequently, a third embodiment of the invention will be described with reference to FIGS. 6 and 7.

The third embodiment is arranged substantially similarly to the aforementioned first embodiment. However, the third embodiment is different from the first embodiment in that the endoscope inserting section which is inserted into the sheath is further inserted into the sheath to improve suction advantages.

In connection with the above, the description of constitutional portions the same as those of the first embodiment will be omitted.

Figure 6:
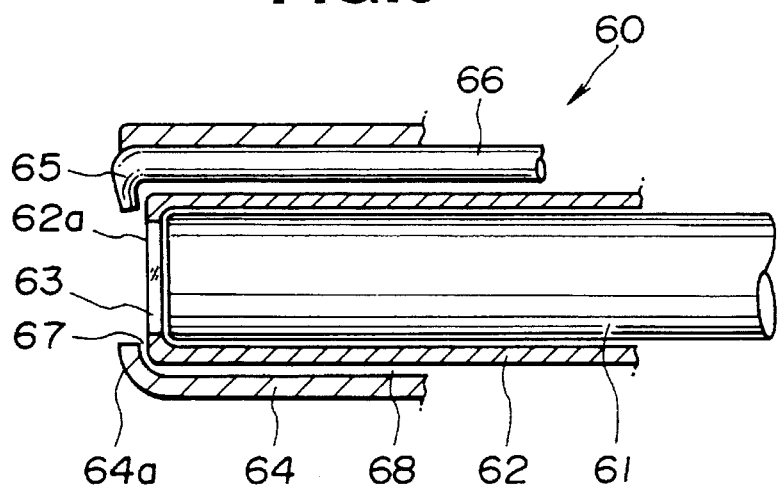
FIG. 6 is an enlarged explanatory view of a distal part of insertion section of an endoscope according to a third embodiment of the invention.
Figure 7:
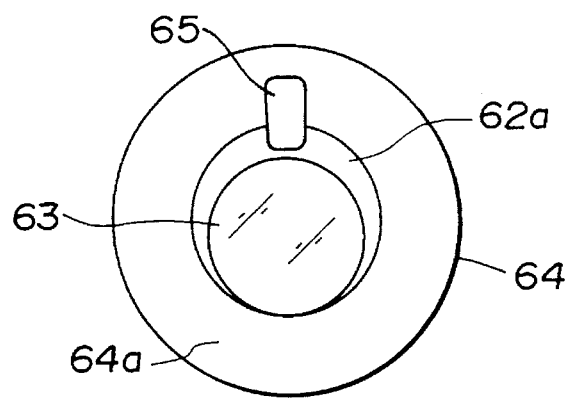
FIG. 7 is an explanatory view of the inserting section of the endoscope which is viewed from the side of the distal part of the endoscope according to the third embodiment.

Specifically, as shown in FIGS. 6 and 7, an inserting section 61 of an endoscope 60 is inserted into a first sheath 62. The first sheath 62 is provided, at a forward end thereof, with a transparent window 63 which cover substantially the entirety of a forward end surface of the endoscope 60 so that the a distal part is made to gas tightness. An outward surface of the transparent window 63 is a smooth surface having no irregularity. The transparent window 63 does not generate a step with respect to the forward end of the sheath 62, but is coplanar therewith. In this connection, such coating may be applied to the outward surface of the transparent window 63 that dirt is difficult to be adhered to the outward surface of the transparent window 63. Moreover, coating which makes it difficult that dirt is adhered may be applied to the outward surface of the transparent window 63. Furthermore, coating which makes it difficult that a blur occurs or is generated may be applied to the inner and outer surfaces of the transparent window 63.

Further, the endoscope inserting section 61 which is inserted into the first sheath 62 is further inserted into a second sheath 64. The second sheath 64 is provided, at the side of the forward end, with a water feed channel 66 having a nozzle 65, similarly to the first embodiment. The grip of the operator of the feed water channel 66 is in communication with cleaning means (not shown) through a feed water line (not shown).

Moreover, the forward end of the second sheath 64 is formed, on the inside, with an edge 64a. Under a state or condition in which the first sheath 62 is inserted into the second sheath, a slight gap, that is, forward-end clearance 67 is defined between the inner surface of the edge 64a and the forward-end surface 62a of the first sheath 62. The edge 64a is formed to such a predetermined size as not to narrow the field of view of observation due to the endoscope 60 (to block the upper portion of the cover window 63 of the first sheath 62, or the like).

Furthermore, a slight gap, that is, an insertion- section clearance 68 is defined between the inner surface of the second sheath 64 and the outer surface of the first sheath 62. The insertion-section clearance 68 is, on the side of a forward end, in communication with the forward-end clearance 67, and is, on the side of a grip for an operator, in communication with suction means through a suction line (not shown).

In the endoscope apparatus arranged in this manner, in case where the transparent window 63 at the forward end of the first sheath 62 is cleaned, cleaning water is blown, by cleaning means (not shown), against the transparent window 63 from a nozzle 66 through a feed water line (not shown) and feed water channel 66.

Subsequently, water drops or the like remaining on the surface of the transparent window 63 are sucked by suction means (not shown) through a suction line, an insertion-section clearance 68 between an inner surface of the second sheath 64 and an outer surface of the first sheath 62, and a forward-end clearance 67 between an inner surface of the edge 64a on the inside of the forward end of the second sheath 64 and the forward-end surface 62a of the first sheath 62.

In this manner, according to the embodiment, the sheaths are provided double, whereby it is possible to securely prevent the dirt from being adhered to the endoscope forward end.

Further, in case where the dirt is adhered to the sheath having, at an intermediate portion, the transparent window, the dirt is cleaned and is removed and, thereafter, suction of the water drops or the like is securely preformed. Thus, it is possible to maintain the observation field of view superior.

Figure 8:
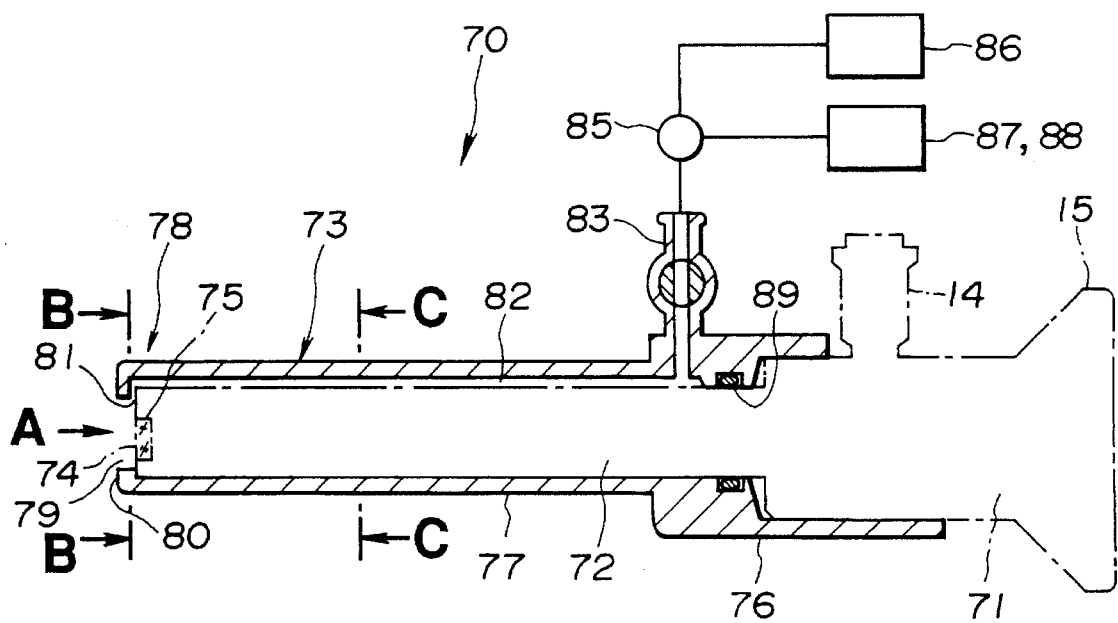
FIG. 8 is a schematic arrangement explanatory view of a whole endoscope apparatus according to a fourth embodiment of the invention.
Figure 9A:
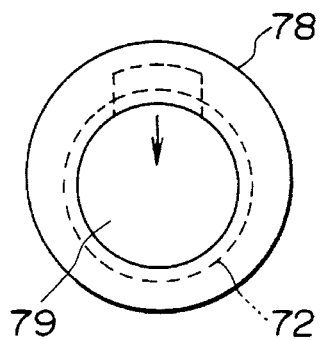
FIGS. 9(a) to FIG. 9(c) are enlarged explanatory views of an inserting section of an endoscope according to a fourth embodiment of the invention, FIG. 9(a) being a view as viewed from an A direction in FIG. 8.
Figure 9B:
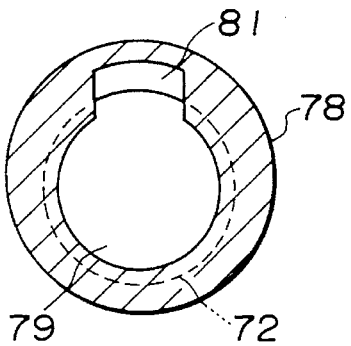
Figure 9C:
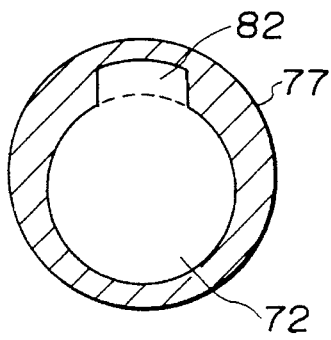
Figure 10:
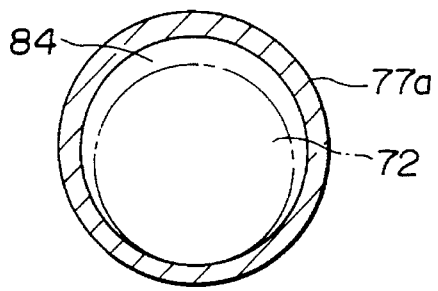
FIG. 10 is a cross-sectional explanatory view of a modification of the inserting section of the endoscope according to the fourth embodiment.

FIGS. 8 to 10 show a fourth embodiment of the invention. In this connection, FIG. 8 is a view showing a schematic arrangement of a whole endoscope apparatus, FIG. 9(a) is a view as viewed from an arrow in an A direction, FIG. 9(b) is a cross-sectional view taken along a line B—B in FIG. 8, and FIG. 9(c) is a cross-sectional view taken along a line C—C in FIG. 8, while FIG. 10 is a cross-sectional explanatory view showing a modification of the endoscope insertion section.

The fourth embodiment is an example in which an arrangement of the insertion-section clearance and the forward-end clearance for water feed and suction in the first embodiment is modified. In connection with this, the other portions are arranged substantially similar to those of the first embodiment. The description of constitutional elements the same as those of the first embodiment will be omitted.

Specifically, as shown in FIG. 8 and FIGS. 9(a)–9(c), an elongated inserting section 72 extends forwardly from a body 71 of an endoscope 70. The endoscope inserting section 72 is inserted into a sheath 73. Further, the endoscope body 71 has an outer peripheral side surface thereof which is provided therein a light guide base 14. An eyepiece unit 15 is provided in rear of the endoscope body 71.

Arranged on the endoscope 70 is a cover glass 75 which blocks an endoscope optical system which is provided within the inserting section, in the forward end surface 74 of the endoscope inserting section 72. A subject image in front of the cover glass 75 is formed by the endoscope optical system. The formed optical image is transmitted to the eyepiece unit 15. Meanwhile, the sheath 73 is so formed as to comprise the sheath body portion 76, a sheath inserting portion 77 and a sheath distal part 78. The endoscope inserting portion 72 is inserted into the sheath inserting portion 77. The sheath body 76 is so mounted as to be fixable with respect to the endoscope body 71. The sheath distal part 78 is provided therein with an opening 79. A light-guide outputting end surface (not shown) of the end surface 74 of the endoscope inserting section and the surface of the cover glass 75 are exposed from the opening 79. illumination and observation of the part to be examined are made possible through the opening 79.

Moreover, an edge 80 for covering a peripheral edge is provided in opposed relation to the endoscope inserting-section forward end surface 74. A distal-part groove or ditch 81 which serves as a forward-end clearance as shown in FIGS. 8 and 9(b) is provided on a part on the inside of the edge 80. On the inner peripheral portion of the sheath inserting portion 77, an inserting-section ditch 82 as shown in FIGS. 8 and 9(c) extends from the sheath body 76 to the sheath distal part 78. The side of the grip for the operator of the inserting-section ditch 82 is in communication with a fluid base 83 which is provided in the sheath body 76. The side of the forward end of the inserting-section ditch 82 is in communication with the distal-part ditch 81. In connection with the above, as a modification of the inserting-section clearance which is provided in the inserting section, as shown in FIG. 10, the arrangement may be such that a gap or clearance 84 is provided between the inner peripheral surface of the sheath inserting section 77a and an outer peripheral surface of the endoscope inserting section 72.

Feed water means 86 and suction means 87 (or feed gas means 88) are connected to the fluid base 83 through a three-way activity plug 85 for changing over the lines. Feed out, gas feed, suction and the like can be performed with respect to the endoscope inserting-section forward-end surface 74 by the feed water means 86, the suction means 87 and the feed gas means 88.

Further, an O-ring 89 is provided in the vicinity of the end on the side of the grip of the operator more than a confluence between the inserting-section ditch 82 and the fluid base 83 within the sheath 73. Gas tightness is maintained between the peripheral portion of the sheath inserting-section and the outer peripheral portion of the endoscope inserting section at the side of the grip of the operator of the inserting-section clearance.

Subsequently, operation of the embodiment which is arranged as described above will be described.

When observation of a diseased or affected part within a body cavity is performed by the endoscope 70, in case where dirt or the like is adhered to the surface of the cover glass 75 of the inserting-section distal part so that cleaning is performed in order to remove the dirt, the three-way activity plug is operated to feed the cleaning water from the feed water means 86 into the sheath. The cleaning water is led to the sheath distal part 78 through the inserting-section ditch 82 and the distal-part ditch 81 between the inner surface of the sheath 73 and the endoscope inserting section 72. The cleaning water is blown against the cover glass 75 by the distal-part ditch 81. Here, flow of the cleaning water or the like in the endoscope inserting-section forward-end surface 74 becomes that as shown by an arrow in FIG. 9(a). A three-way activity plug 85 is operated to cause the suction means 87 to communicate with the fluid base 83 of the sheath 73. Negative pressure is caused to occur on the endoscope inserting-section forward-end surface through the distal-part ditch 81 and the inserting-section ditch 82 to suck the water drops or the like which remain on the surface of the cover glass 75 or the like, from the distal-part ditch 81. In this connection, the arrangement may be such that the feed gas means 88 is in communication with the interior of the sheath 73 in place of the suction means 87, gas feed is performed through the distal-part ditch 81 and the inserting-section ditch 82, and the water drops or the like which remain on the surface of the cover glass or the like are blown away or off by gas of carbon dioxide gas, compressed air or the like.

According to the arrangement of the embodiment, it is possible to perform suction effectively from the overall periphery of the opening 79, including not only the distal-part ditch 81, but also the clearance between endoscope inserting-section forward-end surface 74 and the edge 80 of the sheath distal part 78 which is provided therein with the distal-part ditch 81.

Moreover, by the suction, it is possible to suck not only the water drops which remain on the surface of the cover glass 75 or the like, but also the water drops or the like which remain on the endoscope inserting-section forward-end surface, such as, for example, the outputting end surface of the light guide or the like. Accordingly, it is possible to always maintain the outputting light quantity, the luminous intensity distribution or the like superior.

Furthermore, even for or in the endoscope of the prior art arrangement, which has already been used in the market, the creation and the use of the sheath capable of combining with the prior art endoscope makes it possible to easily and efficiently the cleaning of the cover glass or the like on the overall periphery of the endoscope inserting-section forward end. Thus, it is possible to sufficiently cope with after-market.

Figure 11:
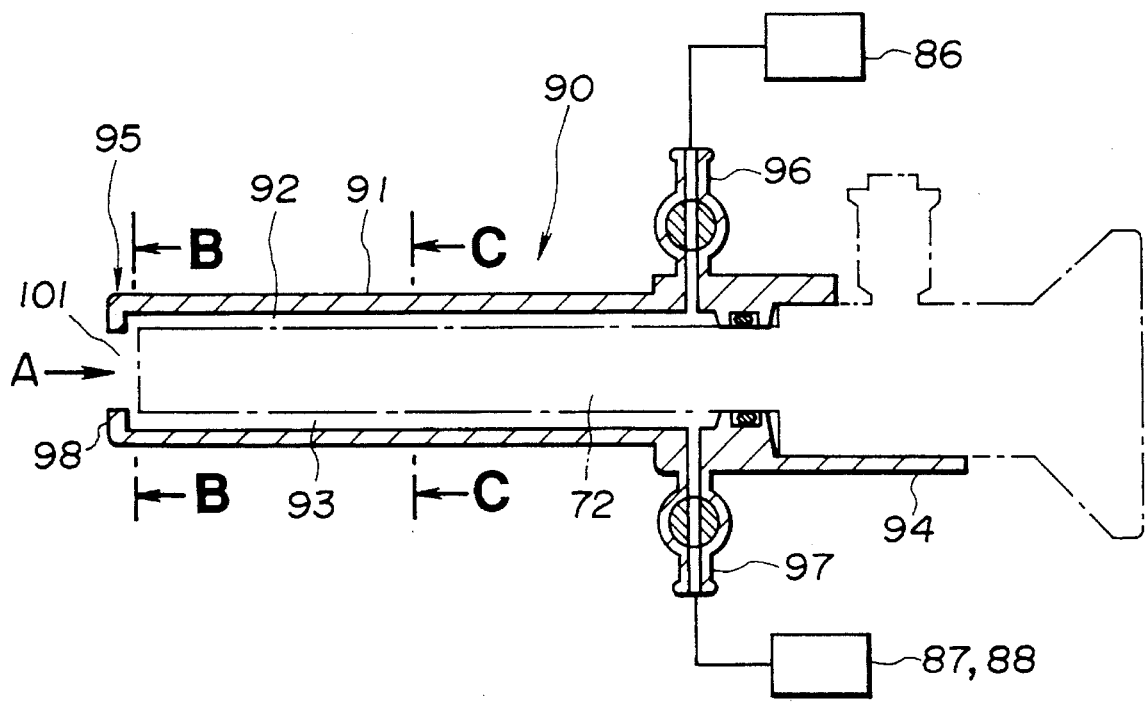
FIG. 11 is a schematic arrangement explanatory view of a whole endoscope apparatus according to a fifth embodiment of the invention.
Figure 12:
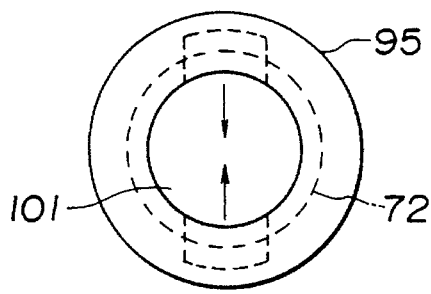
FIGS. 12(a) to FIG. 12(c) are enlarged explanatory views of an inserting section of an endoscope according to a fifth embodiment of the invention, FIG. 12(a) being a view as viewed from an A direction in FIG. 11.
Figure 12:
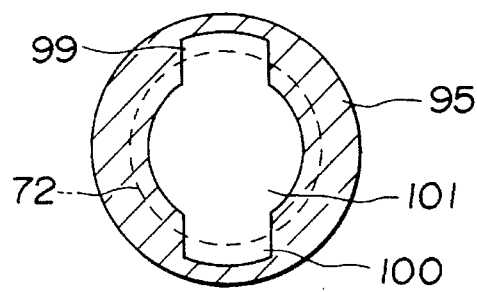
Figure 12:
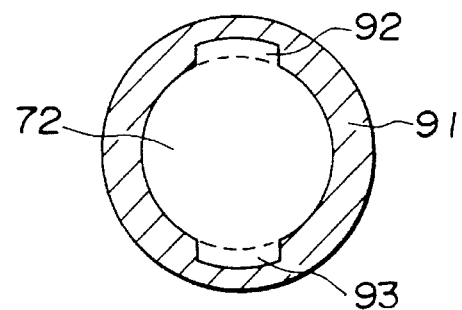

FIGS. 11 to 15 show a fifth embodiment of the invention. In this connection, FIG. 11 is a view showing a schematic arrangement of a whole endoscope apparatus, FIG. 12(a) is a view as viewed from an arrow from a A direction in FIG. 11, and FIG. 12(b) is a cross-sectional view taken along a line B—B in FIG. 11, while FIG. 12(c) is a cross-sectional view taken along a line C—C in FIG. 11.

The fifth embodiment is an example in which the clearance for water feed and the clearance for suction are provided separately from each other. In this connection, the other portions are arranged substantially similar to those of the first embodiment. The description of constitutional elements the same as those of the first embodiment will be omitted.

Specifically, as shown in FIG. 11 and FIGS. 12(a) ! A12(c), a feed-water inserting-section ditch 92 and a suction inserting-section ditch 93 serving as inserting-section clearances as shown in FIG. 12(c) extend from the sheath body 94 to the sheath distal part 95, in the inner periphery of the sheath inserting section 91 of the sheath 90 into which the endoscope inserting section 72 is inserted. The feed water inserting-section ditch 92 and the suction inserting-section ditch 93 have respective sides of a grip of an operator, which are in communication with a water feed base 96 and a suction base 97 which are respectively provided in the sheath body 94, while the feed water inserting-section ditch 92 and the suction inserting-section ditch 93 have respective sides of a forward end, which are in communication with a water-feed distal-part ditch 99 and a suction distal-part ditch 100 which serve as the forward-end clearances provided on the inside of the edge 98 of the sheath distal part 95. Furthermore, an opening 101 is provided in the sheath distal part 95, similarly to the forth embodiment. The endoscope inserting-section forward-end surface is exposed by the opening 101.

Feed water means 86 and suction means 87 (or gas feed means 88) are connected respectively to the feed water base 96 and the suction base 97.

In the sheath 90 arranged in this manner, when the endoscope inserting section 72 is inserted into the sheath 90, the feed water inserting-section ditch 92, the feed water distal part ditch 99 and the suction inserting section ditch 93, and the suction distal part ditch 100 form channels which are air-tight and which are independent of each other. Accordingly, feed water and suction (or feed gas) are made possible to be performed separately or simultaneously by the channels different from each other. At this time, flow of the cleaning water or the like in the endoscope inserting-section forward-end surface comes into that indicated by chain lines in FIG. 12(a).

Figure 13:
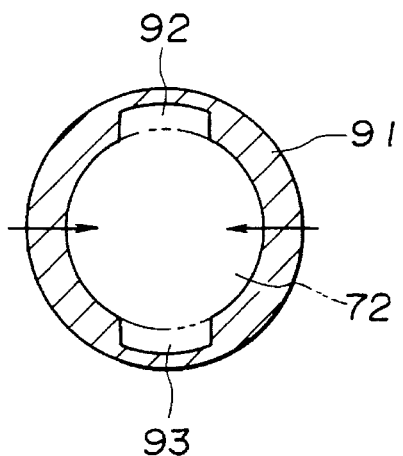
FIGS. 13 and 14 are views for the description of a gas-tight structure of a clearance portion between an insertion section and a sheath insertion section of an endoscope according to a fifth embodiment, FIG. 3 being a cross-sectional explanatory view of the sheath inserting section under a condition in which the endoscope is inserted.
Figure 14:
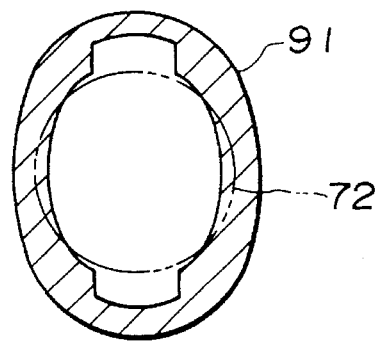

In order to make the feed-water inserting-section ditch 92 and the suction inserting-section ditch 93 to channels which are air-tight and which are independent of each other, the sheath inserting section 91 is arranged as shown, for example, in FIGS. 13 and 14. In this connection, FIG. 13 shows a cross-sectional configuration or shape or form of the sheath inserting section 91 under a condition in which the endoscope insertion section 72 is inserted, while FIG. 14 shows a cross-sectional configuration or shape or form of the sheath inserting section 91 under a condition prior to the fact that the the endoscope insertion section 72 is inserted.

Specifically, the arrangement is such that the sheath inserting section 91 is formed by an elastic member, and an inner diameter of a portion which does not form the feed water inserting-section ditch 92 and the suction inserting-section ditch 93, in the inner periphery of the sheath inserting section 91 (a lateral width in the figure) is so set as to be slightly smaller than an outer diameter of the endoscope inserting section 72. The sheath inserting section 91 is formed in this manner, whereby, when the endoscope inserting section 72 is inserted, a biasing force as indicated by broken lines in FIG. 13 by an elastic force of the sheath inserting section 91 so that the inner periphery of the sheath clamps the endoscope outer periphery and is in close contact therewith. Thus, it is possible to maintain the feed-water inserting-section ditch 92 and the suction inserting ditch 93 air-tight from each other.

Figure 15:
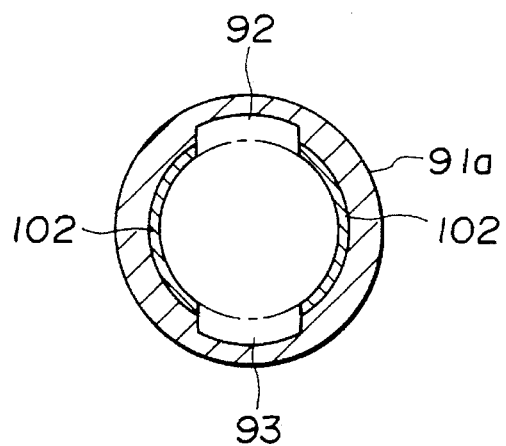
FIG. 15 is a cross-sectional explanatory view showing a modification of the gas-tight structure of the clearance portion.

Moreover, as a modification of the gas-tight structure of the clearance between the endoscope inserting section and the sheath inserting section, the arrangement may be such that, as shown in FIG. 15, an elastic material 102, such as rubber or the like, is provided on a portion which is in contact with the endoscope inserting-section outer periphery in the inner periphery of the sheath inserting section 91a, and the sheath inner periphery is in close contact with the endoscope outer periphery by the elastic material 102, so that gas tightness of the feed water inserting-section ditch 92 and the suction inserting-section ditch 93 is maintained.

According to the arrangement of the embodiment, the endoscope inserting section and the sheath are combined with each other, whereby it is possible to easily form the water feed passage and the suction or feed gas passage independently of each other.

Figure 16:
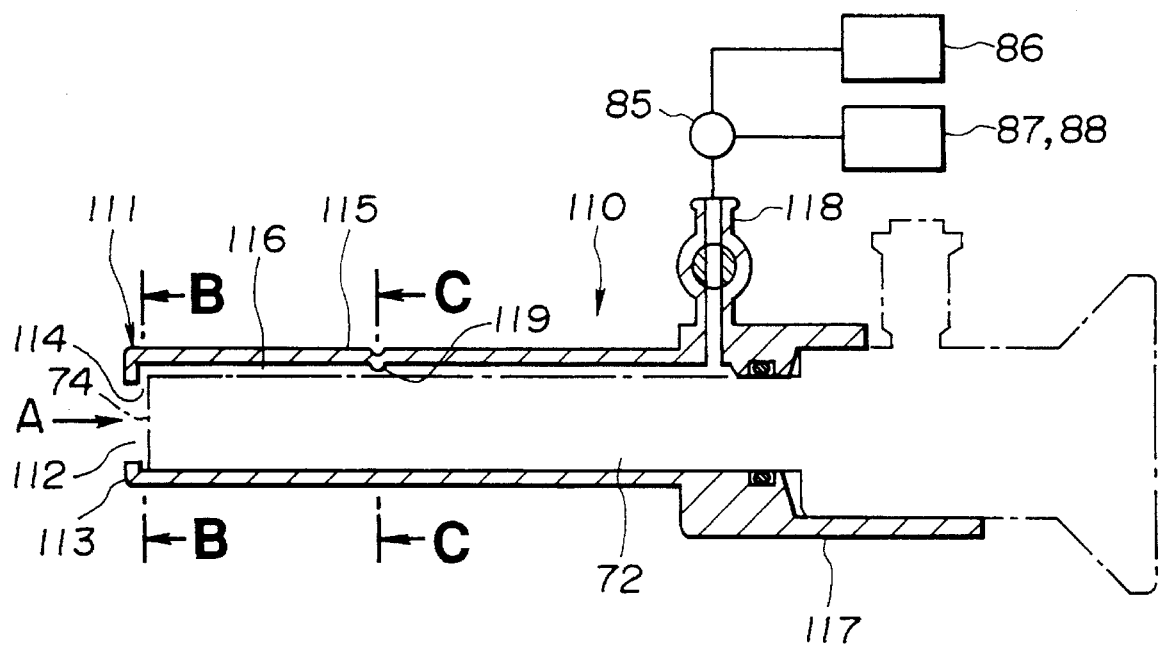
FIG. 16 is a schematic arrangement explanatory view of a whole endoscope apparatus according to a sixth embodiment of the invention.
Figure 17:
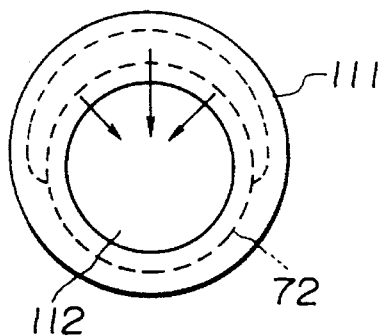
FIGS. 17(a) to FIG. 17(c) and FIG. 18 are enlarged explanatory views of an inserting section of an endoscope according to the sixth embodiment of the invention, FIG. 17(a) being a view as viewed from an A direction in FIG. 16.
Figure 17:
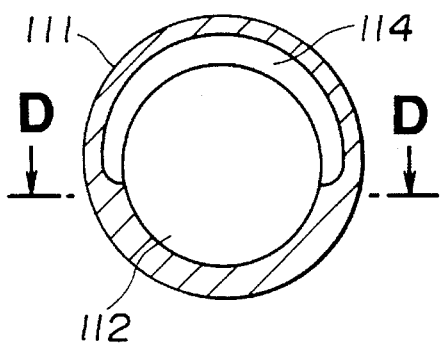
Figure 17:
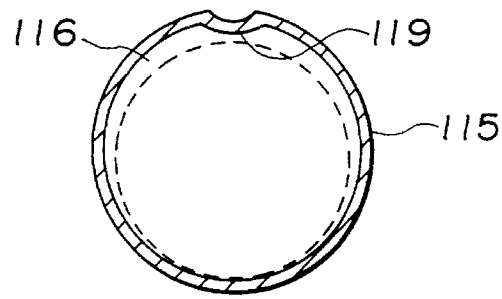
Figure 18:
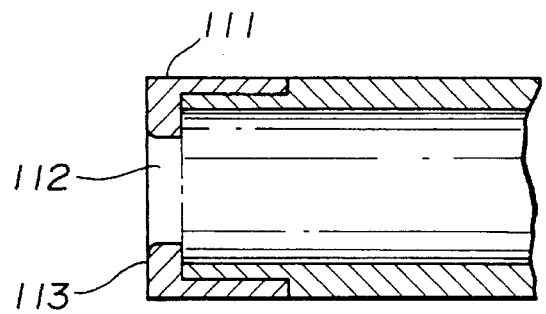
Figure 19:
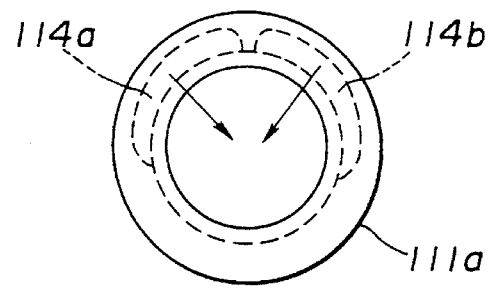
FIG. 19 is an explanatory view showing a modification of a gap portion at a sheath distal part according to the sixth embodiment.

FIGS. 16 to 19 show a sixth embodiment of the invention. In this connection, FIG. 16 is a view showing a schematic arrangement of a whole endoscope apparatus, FIG. 17(a) is a view indicated by an arrow as viewed from an A direction in FIG. 16, FIG. 17(b) is a cross-sectional view taken along a line B—B in FIG. 16, FIG. 17(c) is a cross-sectional view taken along a line C—C in FIG. 16, and FIG. 18 is a cross-sectional view taken along a line D—D in FIG. 17(b), while FIG. 19 is an explanatory view showing a modification of the clearance at the sheath distal part.

The sixth embodiment is a modification of the fourth embodiment. The embodiment is an example in which the arrangement of the clearance for the water feed and the suction in the fourth embodiment is modified. In this connection, the description of constitutional portions the same as those of the fourth embodiment will be omitted.

Specifically, as shown in FIGS. 16 to 18, a sheath distal part 111 into which the endoscope inserting section 72 is inserted is provided with an opening 112. An edge 113 is provided which covers a periphery in opposed relation to the endoscope inserting-section forward-end surface. A distal-part ditch 114 which serves as a forward-end clearance is formed in a part on the inside of the edge 113. Further, the sheath inserting section 115 is such that an inner diameter thereof is slightly larger than an outer diameter of the endoscope inserting section. As shown in FIG. 17(c), a clearance 116 is defined between the sheath inserting-section inner periphery and an outer periphery of the endoscope inserting section. The clearance 116 extends to the sheath distal part 111 from the sheath body 117. The side of a grip for an operator is in communication with the fluid base 118 which is provided on the sheath body 117, while the forward-end side is in communication with the distal part ditch 114. Moreover, a projection 119 which projects toward the side of the inner periphery of the sheath is provided non a part in the vicinity of the forward end of the sheath inserting section 115. Thus, a position is capable of being prescribed so that the positional relationship in a peripheral direction between the sheath inserting section 115 and the endoscope inserting section 72 is always made constant. In this connection, the arrangement may be such that a plurality of projections 119 are provided, and positioning of the endoscope inserting section 72 with respect to the sheath inserting section 115 is performed.

In the sheath 110 arranged in this manner, flow of the cleaning water or the like at the endoscope inserting-section forward-end surface comes into that indicated by broken lines in FIG. 17(a). Furthermore, in case where the water drops or the like which remain on the surface of the cover glass or the like are sucked, suction is possible from the overall periphery of the opening 112, including not only the forward-end ditch 114, but also the clearance between the endoscope inserting-section forward-end surface and the edge 113 which is provided therein with the distal-part ditch 114. Accordingly, it is possible to perform suction which is superior in efficiency.

In connection with the above, as a modification of the distal part ditch in the distal part of the sheath, the arrangement may be such that, as shown in FIG. 19, ditches divided into at least two like distal part ditches 114a and 114b are provided in the inside of the edge of the sheath distal part.

The distal part ditch is divided in this manner, whereby flow of the cleaning water or the like with respect to the cover glass at the forward-end surface of the endoscope inserting section comes into that as shown in arrows in FIG. 19. Thus, it is possible to improve flow of the water upon feeding of the water, to improve cleanliness or washability. Further, it is possible to improve suction efficiency.

Subsequently, the other arrangement example of the feed water means and the suction means will be indicated below as a cleaning mechanism.

Figure 20:
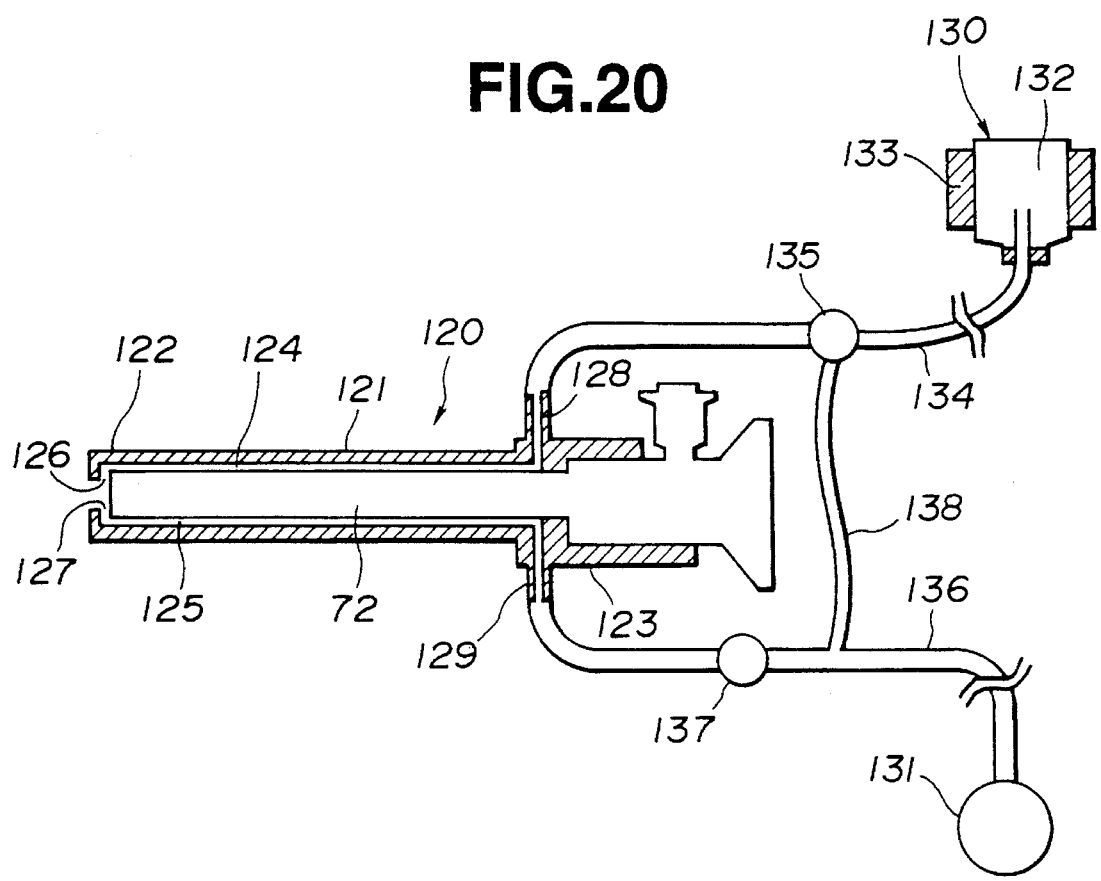
FIG. 20 is an arrangement explanatory view showing a first arrangement example of a cleaning mechanism.

FIG. 20 is an arrangement explanatory view showing a first arrangement example of the cleaning mechanism.

A sheath 120 into which an endoscope inserting section 72 is inserted is so arranged as to be provided with a feed water inserting-section ditch 124 and a suction inserting-section ditch 125 within the sheath inserting section 121, similarly to the aforesaid fifth embodiment. The feed water inserting-section ditch 124 and the suction inserting-section ditch 125 are arranged such that forward-end sides thereof are in communication with the feed water distal-part ditch 126 and the suction distal-part ditch 127 which are provided in the distal part, while the side of a grip of an operator is in communication with the water feed base 128 and the suction base 129 which are provided in the sheath body 123.

Feed water means 130 is connected to the feed water base 128, while suction means 131 provided with a suction pump is connected to the suction base 129. The feed water means 130 is provided with a feed water bottle 132 and heating means 133 which is provided on the periphery of the feed water bottle 132 for heating cleaning water within the bottle.

Moreover, the water feed means 130 and the sheath 120 are connected to each other by the feed water tube 134. A three-way activity plug 135 is provided in the vicinity of the feed water tube 134, on the side of the sheath, for guiding the cleaning water to the sheath 120 from the feed water means 130. Meanwhile, the suction means 131 and the sheath 120 are connected to each other by a suction tube 136. A valve 137 for opening and closing a line of the tube is provided in the vicinity of the suction tube 136, adjacent to the side of the sheath, for leading drainage or wastewater to the suction means 131 from the sheath 120. Furthermore, a communication tube 138 extends from the three-way activity plug 135 which is provided on the way of the feed water tube 134. The communication tube 138 is connected from the valve 137 of the suction tube 136 to a line on the side of the suction means 131.

Here, the arrangement of the three-way activity plug 135 will be described with reference to FIG. 21(*a*) FIG. 21(*c*). FIG. 21(*a*) shows a state or condition in which the cleaning water does not flow in any of the sheath and the suction tube under an OFF-state. FIG. 21(*b*) shows a state in which the cleaning water flows to the suction tube through a communication tube. FIG. 21(*c*) shows a state in which the cleaning water flows to the sheath.

A piston 140 is arranged within a three-way activity plug body 139. The piston 140 is biased upwardly by a spring 141. When the piston 140 is not operated, the piston 140 is in a state illustrated in FIG. 21(*a*). The body 139 is provided with bases 142, 143 and 144 to which a tube in communication with the feed water means 130, a tube in communication with the sheath 120 and a tube in communication with the suction means 131 are connected.

When the piston 140 is pushed one step, a state comes into a state of FIG. 21(*b*). The water feed means 130 is in communication with the communication tube 138 and the suction tube 136. Thus, the cleaning water flows to the suction tube 136. When the piston 140 is pushed further one step, a state comes into a state of FIG. 21(*c*). The water feed means 130 is in communication with the communication tube 134. Thus, the cleaning water flows to the suction tube 134. Under the state, it is possible to feed water to the endoscope distal part through the feed water ditch.

When cleaning of the endoscope inserting-section forward-end surface is performed, the three-way active plug 135 is first operated to communicate the feed water tube 134 and the suction tube 136 with each other. Then, the cleaning water which is heated to the body temperature by the heating means 133 flows out from the feed water means 130, and flows toward the side of the suction means 131 through the communication tube 138. At this time, since the feed water tube per se is the same as the room temperature prior to operation of the three-way active plug, heat is taken away from the cleaning water which remains within the feed water tube 134 prior to the operation, and the cleaning water which flows within the feed water tube 134 immediately after the operation, to the feed water tube so that the temperature of the cleaning water is reduced from the body temperature to the vicinity of the room temperature. However, when the cleaning water continues to flow to some degree, since the feed water tube 134 is warmed, the temperature of the flowing cleaning water comes into the temperature the same as that of the cleaning water which is warmed by the body temperature within the feed water bottle 132. Subsequently, the three-way active plug 135 is operated to cause the feed water tube 134 to communicate with the sheath 120. The cleaning water flows into the cleaning ditch in the sheath 120. Then, the cleaning water is sent to the sheath distal part 122, and is blown against the endoscope inserting-section forward-end surface so that the cover glass or the like is cleaned.

With the arrangement of the cleaning mechanism in this manner, it is possible to feed only the cleaning water which is warmed by the body temperature, into the sheath. Since the endoscope inserting section is not cooled by the cool cleaning water, it is possible to prevent the lens of the endoscope from being blurred, making it possible to secure a superior field of view.

FIG. 22 is an arrangement explanatory view showing a second arrangement example of the cleaning mechanism.

In the second arrangement example, a feed water tube 151 in communication with the feed water mans 130 and a suction tube 152 in communication with the suction means 131 are connected to the feed water valve 149 and the suction valve 150 which are provided in a body of a sheath 120. A feed water means 130 and a feed water tube 151 have respective outer peripheries thereof which are covered by the heating tuber 153 for warming the the cleaning water within the feed water means 130 and the feed water tube 151. Heating means 154 for warming the cleaning water to a temperature of the body temperature is connected to the heating tube 153.

By the fact that the heating means is provided to arrange the cleaning mechanism, it is possible to feed only the cleaning water which is always warmed to the body temperature, to the sheath 120. Thus, it is possible to prevent the lens of the endoscope from being blurred, similarly to the first arrangement example.

Moreover, the arrangement may also be such that, in place of the provision of the cleaning mechanism, the inserting-section distal part is warmed to prevent the lens of the endoscope from being blurred.

Figure 23:
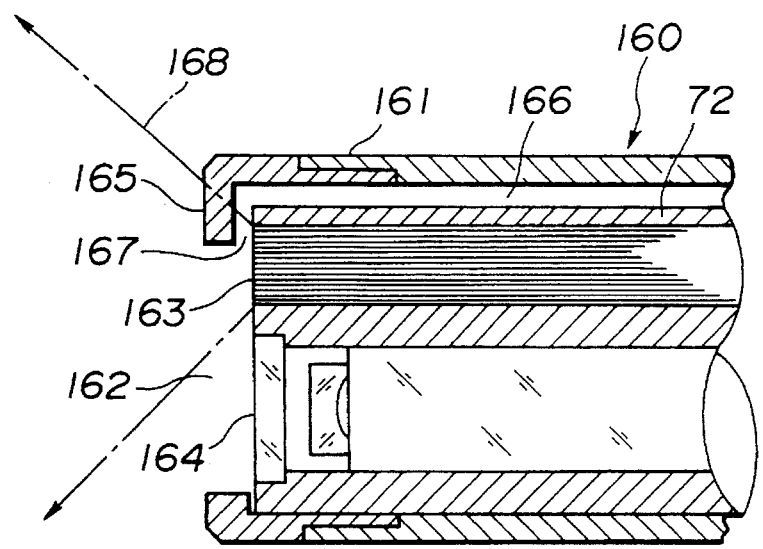
FIG. 23 is an arrangement explanatory view showing a first arrangement example of lens-blur preventing means.

A first arrangement example of the lens blur preventing means is shown in FIG. 23. The first arrangement example is an example in which the sheath distal part is arranged such that the cleaning-water jetting port in the inserting-section distal part is capable of being heated by an illuminating light.

An opening 162 is provided in the sheath distal part 161 of the sheath 160 into which the endoscope inserting section 72 is inserted. A light guide outputting end surface 163 of the endoscope inserting-section forward-end surface and a cover glass 164 are exposed from the opening 162. Illumination and observation of a region to be examined are made possible through the opening 162.

Furthermore, the sheath distal part 161 is provided with an edge 165 which covers a peripheral portion in opposed relation to the endoscope inserting-section forward- end surface. A distal-part ditch 167 which serves as a forward-end clearance is provided in a part of the edge 165 on the inside thereof. The distal-part ditch 167 is in communication with the clearance 166 which is provided in the inside of the sheath inserting section. The cleaning water which is sent from the feed water means into the sheath is adapted to be blown against the endoscope forward-end surface through the clearance 166 and the distal-part ditch 167.

In connection with the above, the sizes of the opening 162 and the edge 165 are set such that the illumination light 168 from the light guide outputting end surface strikes against or is applied to a portion of the edge 165 of the opening 162 in the sheath distal part 161.

In the endoscope apparatus in which the sheath distal part is arranged in this manner, a part of the illumination light which illuminates the region to be examined, which is outputted from the light guide outputting end surface 163 impinges against or is applied to a portion of the edge 165 of the opening 162 so that the opening 162 is warmed by the illumination light. Further, by the heat of the illumination light, the cleaning water which jetted from the end of the distal-part ditch 167 and the endoscope inserting-section distal-part is warmed.

Accordingly, since the endoscope inserting-section forward-end surface is not cooled by the cool cleaning water, it is possible to prevent the lens of the endoscope from being blurred.

Moreover, the outputting light of the light source device is used to warm the endoscope distal part prior to the fact that the endoscope is used, whereby it is also possible to prevent the lens of the endoscope from being blurred.

Figure 24:
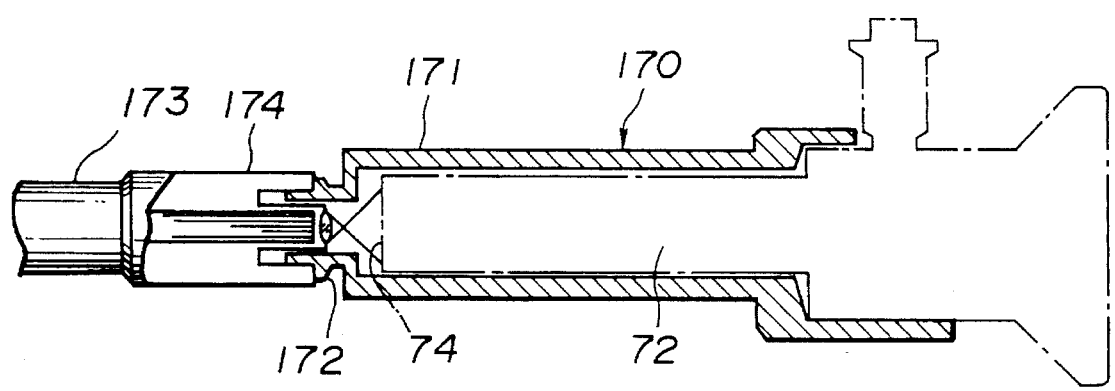
FIGS. 24 and 25 show an example which uses a light emission device as a second arrangement example of the lens-blur preventing means, FIG. 24 being an arrangement explanatory view of the neighborhood of the distal part of the sheath.
Figure 25:
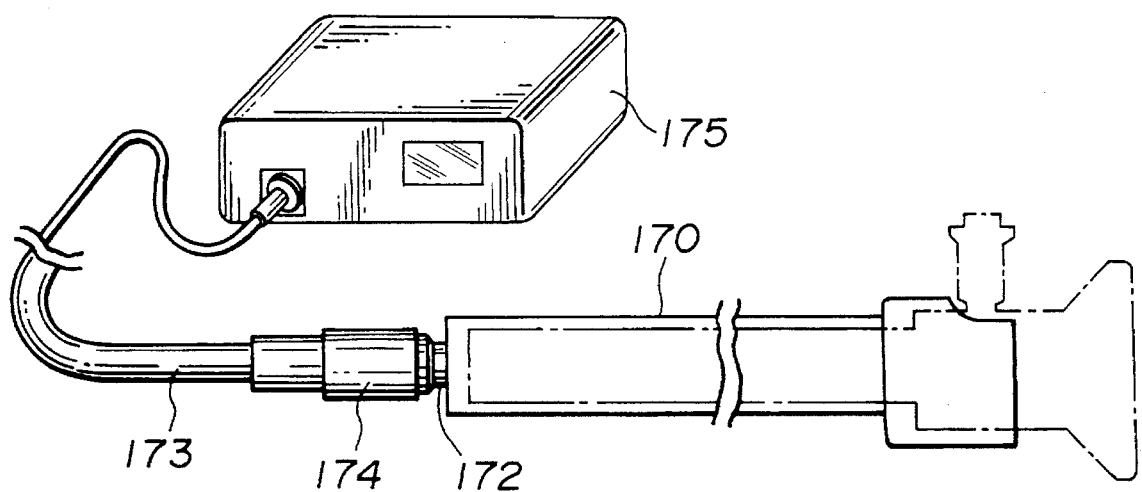

An example which uses the outputting light from the light source device is shown in FIGS. 24 and 25 as a second arrangement example of the lens blur preventing mean.

Generally, upon preparation of equipments prior to operation and upon security or insurance and operation of a path for narcosis or anesthesia, a path for disinfection of an affected or diseased part and a path for inserting the endoscope into a body cavity, or the like, the light source device, the light guide and the endoscope are not required or are unnecessary. Accordingly, in the example, the arrangement is adapted to be arranged such that the light source device at this time is used to connect the outputting end of the light guide cable which is connected to the light source device so that the endoscope distal part is warmed by a white light from the light source device.

An opening is provided in a sheath distal part 171 of a sheath 170 into which the endoscope inserting section 72 is inserted, similarly to the aforementioned embodiment. A base 172 is so provided as to protrude from the opening. A connecting portion 174 on the side the outputting end, of the light guide cable 173 which is connected to the light source device 175 is connected to the base 172. A white light from the light source device 175 is applied to the endoscope inserting-section forward-end surface 74 through the light guide cable 173. It is possible to warm the distal part of the endoscope by the white light from the light source device. Thus, it is possible to prevent the lens of the endoscope from being blurred which causes the field of view of the endoscope to be disturbed.

Further, in the example, prior to the fact that the endoscope is used, that is a preparation stage upon observation and therapeutics procedure due to the endoscope, the distal part is warmed to prevent the lens from being blurred. Accordingly, efficiency is superior in view of time. Further, special or specific equipments such as a scope heater and the like and expensive devices are not required or unnecessary as lens blur preventing means. Thus, it is possible to prevent the equipments within an operation ground or field from increasing in number. No especial economic burden is also applied to the operator.

Figure 26:
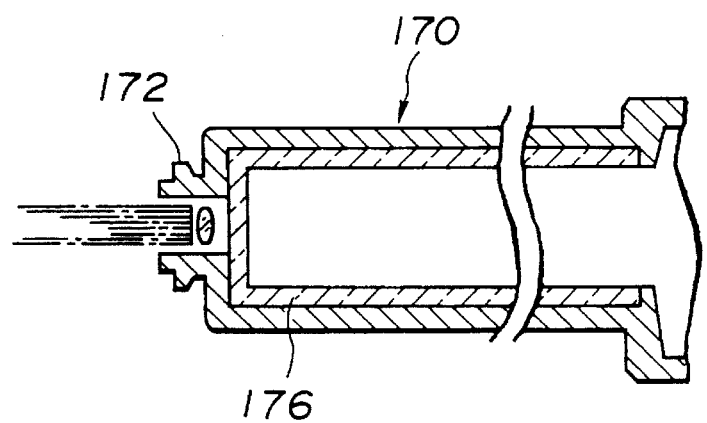
FIG. 26 is an arrangement explanatory view showing a modification of the lens-blur preventing means which uses the emitted light of the light source device.

Moreover, as a modification of the lens blur preventing means which uses the outputting light from the light source device, the arrangement may be such that, as shown in FIG. 26, a tube 176 which is made of heat conduction material and whose distal part is blocked is arranged within the sheath inserting section. In this manner, by the arrangement in which the illumination light from the light guide cable is applied to the forward-end surface of the tube 176, the arrangement may be such that the tube is first warmed by the illumination light, and the endoscope distal part and the endoscope inserting section are warmed by the warmed tube. According to the arrangement of the modification, it is possible to prevent deficiencies such as alteration of adhesives on the endoscope forward-end surface and the fact that burnt deposits of the dirt adhered to the endoscope forward-end surface are adhered to the forward-end surface, or the like, due to the fact that a light from the light guide directly strikes against or is directly applied against.

FIGS. 27 to 37 show a seventh embodiment of the invention.

Figure 27:
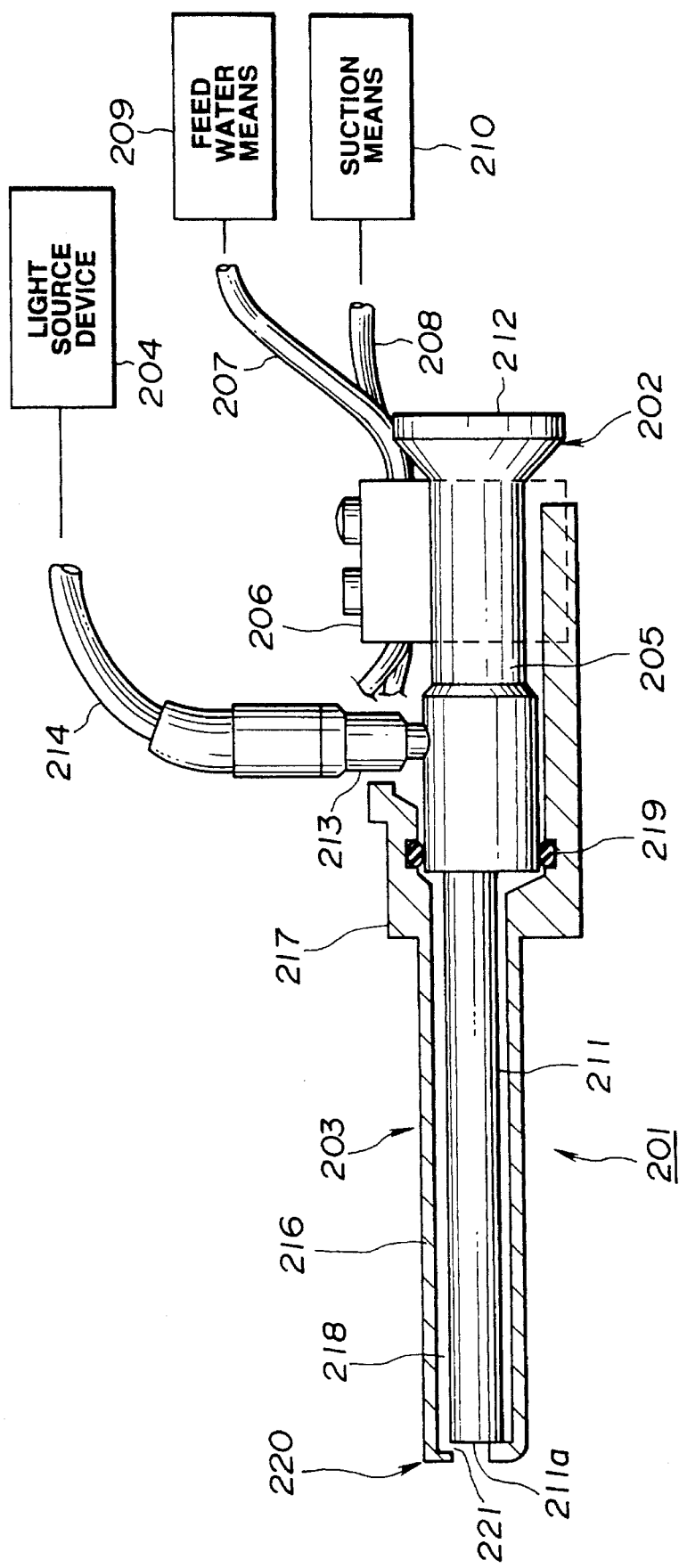

As shown in FIG. 27, an endoscope apparatus 201 according to the seventh embodiment is so arranged as to comprise a rigid endoscope 202, a sheath 203 over which the rigid endoscope 202 is covered, a light source device 204 for supplying an illumination light to the rigid endoscope 202, a valve unit 206 detachable mounted on an endoscope body 205 of the rigid endoscope 202 in a plurality of orientations, and feed water means 209 and suction means 210 connected respectively to a feed water tube 207 and a suction tube 208 which are connected to the valve unit 206.

The rigid endoscope 202 is so arranged as to comprise a rigid endoscope inserting section 211 which is formed by an elongated metal pipe or the like, a large diameter endoscope body 205 formed at a rearward end of the endoscope inserting section 211, and an eyepiece unit 212 which is provided at a rearward end of the endoscope body 205. A light guide (not shown) for transmitting an illumination light is inserted into the endoscope inserting section 211. The light Guide has a rearward end thereof which reaches a light guide base 213 which is provided on the endoscope body 205.

The light Guide base 213 is connected to the light source device 204 through the light Guide cable 214. The illumination light due to the light source device 204 is transmitted by a light guide (not shown) within the light cable 214 and within the rigid endoscope 202. The illumination light is outputted forwardly from a forward-end outputting surface which is mounted on an illumination window (not shown) in a forward end surface 211a of the endoscope inserting section 211.

A subject such as an illuminated affected or diseased part or the like is formed to a focal plane by an objective lens (not shown) which is mounted on an observation window formed adjacent to the illumination window in the forward end surface 211a. An optical image thereof is transmitted rearwardly by an image guide such as a relay optical system (not shown) or the like which is inserted into the endoscope inserting section 211. Thus, it is possible to observe, in enlargement, the (transmitted) optical image by the naked eye through an eyepiece (not shown) which is provided at the eyepiece unit 212.

The sheath 203 which is detachably mounted on the endoscope inserting section 211 and the endoscope body 205 has a sheath inserting section 216 which covers the endoscope inserting section 211, and a sheath body 217 which is formed at the rearward end of the sheath inserting section 216 and which covers the endoscope body 205.

A line 218 is formed or defined between the sheath inserting section 216 and the endoscope inserting section 211. The side of a grip of an operator is kept in gas tightness by an O-ring between the sheath body 217 and the endoscope body 205. The line 218 has the forward end side thereof which is in communication with the nozzle unit 221 which is provided on the sheath distal part 220.

As shown in FIG. 28, the side of the grip for the operator of the line 218 within the sheath 203 is in communication with one or more bases 223 and 224 which is or are provided in the sheath body in the vicinity of the side of the forward end of the O-ring 219.

In the seventh embodiment, the valve unit 206 is detachably mounted on the endoscope body 205 in a plurality of orientation and is regulated in position by the sheath body 217. The feed water tube 207 and the suction tube 208 are connected to the base 223 of the sheath 202 tough the mounting portion 225 of the valve unit 206. A cap 226 is mounted on the base 224 on which the mounting portion 225 is not mounted, of the bases 23 and 224 which are provided on the sheath body 217, to block an opening of the base 224.

To be described subsequently, in the feed water tube 207 and the suction tube 208, turning ON/OFF of feeding or suction of water flowing in the tube and flow regulation are made possible by operation of a feed water button 227 and a suction button 228 which are provided on the valve unit 206.

As shown in FIG. 28 and FIG. 29, narrow ditches 234 and 245 and a generally U-shaped ditch 233 having a wide width portion 231 slightly wider in width than a diameter of the light guide base 213 of the rigid endoscope 202 and a narrow width portion 232 which is located at the opening end and which is slightly smaller in width than the diameter of the light guide base 213 are provided alternately, whereby a pair of pawls 236 ad 237 are formed. When the endoscope inserting section 211 is inserted into the sheath inserting section 216, the light guide base 213 of the rigid endoscope 202 is put between the pair of pawl portions 236 and 237 so that the rigid endoscope 202 is prevented from being rotated or from slipping down or off longitudinally.

In connection with the above, the pawl portions 236 and 237 are formed by the generally U-shaped ditch 233 and the narrow ditches 234 and 235 which are provided in the sheath body 217, but may be arranged such that, as shown in FIG. 30(a) and 30(b), the light guide base 213 of the rigid endoscope 202 is fixed by the generally U-shaped pawl member 239.

Figure 31:
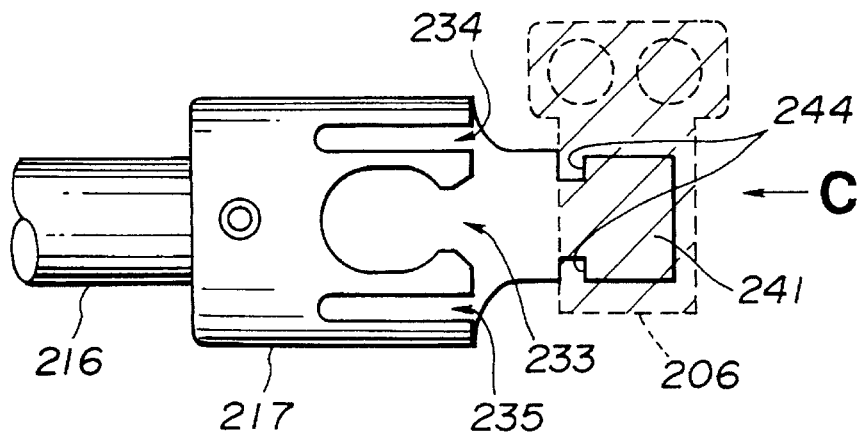
Figure 32:
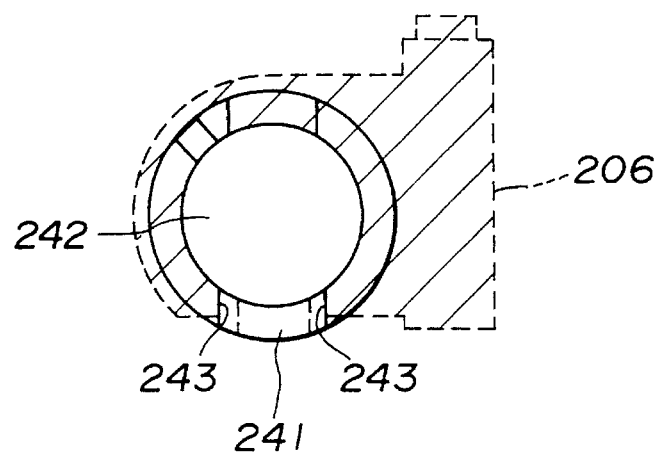
Figure 33:
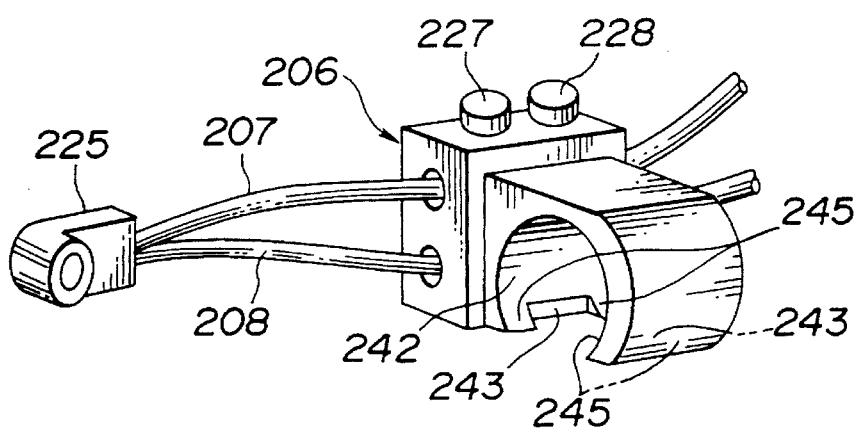

As shown in FIG. 31, FIG. 32 and FIG. 33, a receipt 241 for positioning, in mounting, the valve unit 206 ad for restricting or limiting the valve unit 206 such that a position of the valve unit 206 does not slip down or off is provided in rear of the lower side of the sheath body 217. When the valve unit 206 is fitted such that the whole opening 242 in the valve unit 206 surrounds the endoscope body 205, the edge 243 of the opening 242 in the valve unit 206 is fitted in the receipt 241 so that rotation of the valve unit 206 is limited.

In connection with the above, in order to facilitate understanding of the outer configuration or outer shape of the valve unit 206, the valve unit 206 is shown by broken lines and hatching in FIGS. 31 and 32.

Moreover, as shown in FIG. 31, two of the pawls 245 (refer to FIG. 33) which are provided at four (4) locations symmetrically on the left- and right-hand sides and longitudinally on both ends of the edge 243 in the valve unit 206 are fitted respectively in the pair of ditches 244 which are provided on a portion of the receipt 241 symmetrically with respect to the right-and left-hand sides, to limit that the valve unit 206 slips down or off axially of the rigid endoscope 202.

Figure 34A:
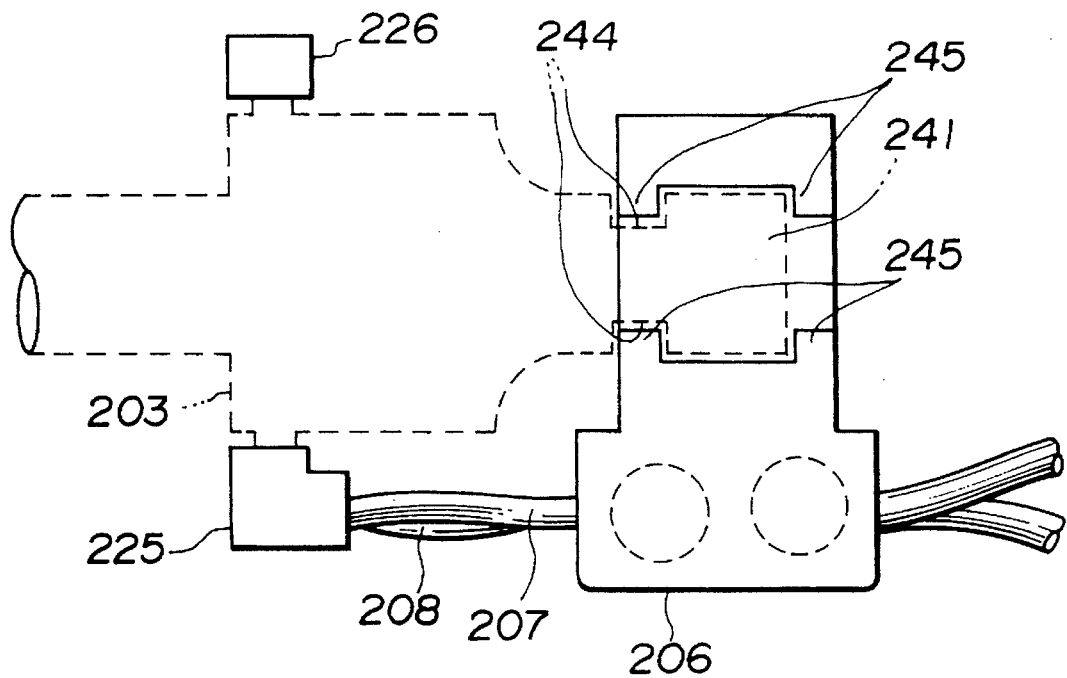
FIGS. 34(a) and 34(b) are explanatory views indicating that the valve unit is capable of being mounted on the endoscope body in a plurality of orientations.
Figure 34B:
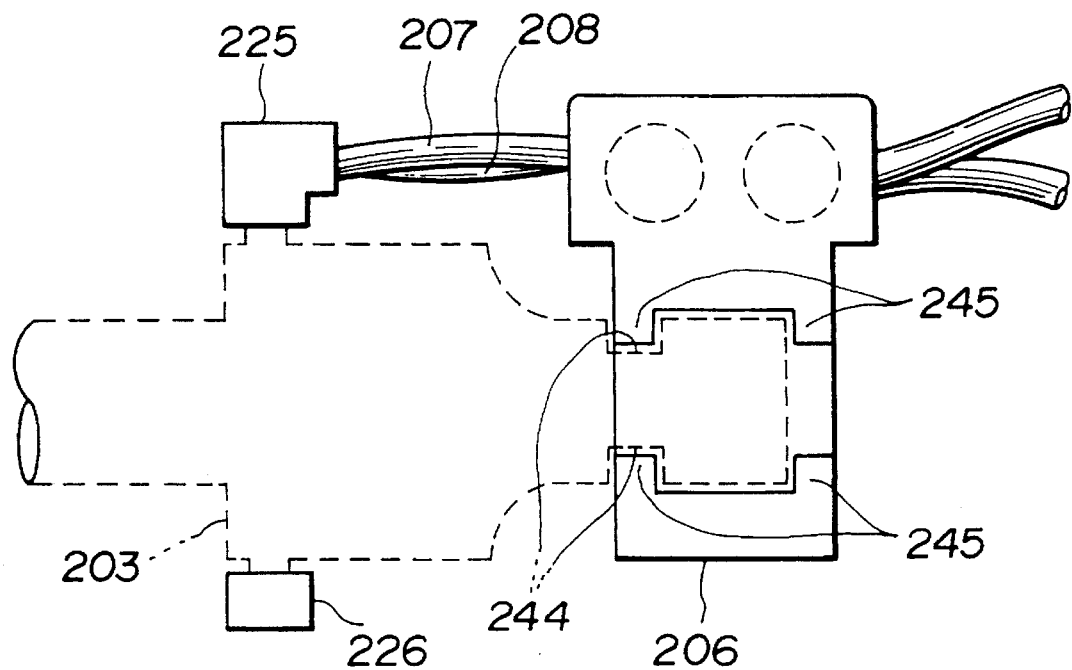

FIG. 34(a) shows a view for viewing, from the lower side of the rigid endoscope 202, a state or condition in which the valve unit 206 is mounted on the endoscope body 205. However, also in case where the position of the valve unit 206 is reverse with respect to the endoscope body 205, mounting is possible as shown in FIG. 34(b). It is possible to select one of them which is easy to operate.

In connection with the above, the arrangement may be such that, in FIG. 34(a) for example, a ditch in which the pawl 245 of the valve unit 206 can be fitted even in a position in front of the receipt 241, in addition to the ditch 244 in the receipt 241 which is provided in the body of the sheath 203 so that the valve unit 206 is detachably mounted on a plurality of positions in the longitudinal direction of the sheath 203. With this arrangement, the valve unit 206 can be mounted on a position and an orientation which are further easy to operate. Thus, the degree of freedom of selection can be widened.

Figure 35:
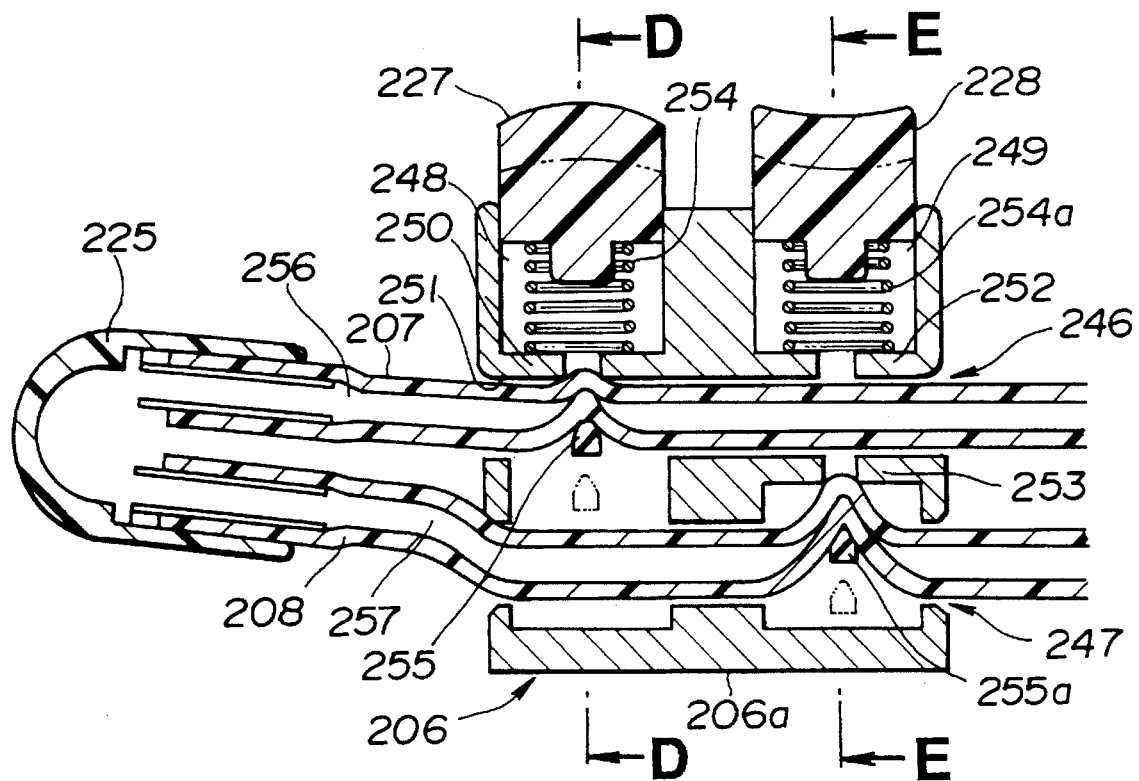
Figure 36:
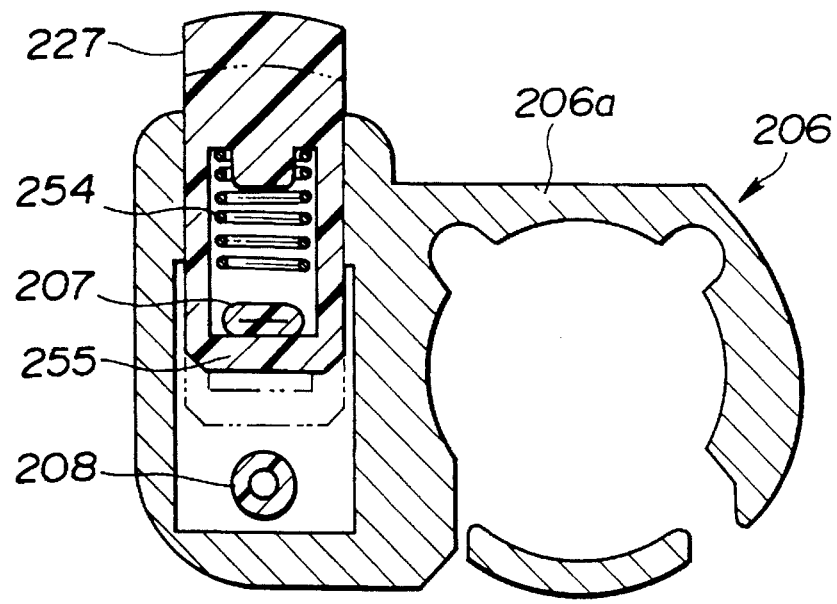
Figure 37:
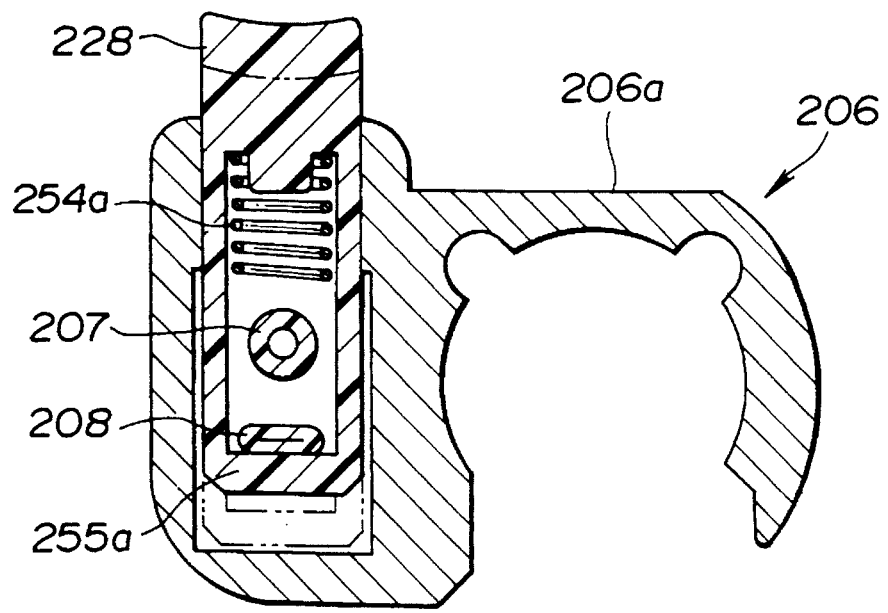

FIG. 35, FIG. 36 and FIG. 37 are cross-sectional views showing a structure of the valve unit 206 and the mounting portion 225. The valve body 206a is provided therein with a feed water lateral hole 246 and a section lateral hole 247 which are vertically arranged and which are so bored as to pass through horizontally, a feed water longitudinal hole 248 and a suction longitudinal hole 249, which are vertically bored so as to be intersected with the pair of lateral holes 246 and 247.

The water feed longitudinal hole 248 is provided therein with a spring retainer 250 and a water feed tube fastener 251 are provided in the feed water longitudinal hole 248, and a spring retainer 252 and a suction tube fastener 253 are provided in the suction longitudinal hole 249

A water feed button 227 which is vertically movably fitted in the water feed longitudinal hole 248 is so provided as to be pushed upwardly with respect to the spring retainer 250 by a spring 254. A lateral shank 255 is provided at a lower end of the feed water button 227 so as to be positioned at the lower side of the feed water tube 207. The arrangement is such that, in keeping with the fact that the feed water button 227 is pushed upwardly by the spring 254, the lateral shank 255 urges the feed water tube 207 against the feed water tube fastener 251 so that the tube 207 is crushed and thus, the line 256 within the tube 207 is closed.

The feed water button 227 is pushed downwardly by a large or great force which overcomes the spring 254, whereby an upper surface of the water feed button 227 is moved to a position indicated by two-dot-and-chain line in FIGS. 35 and 36. Thus, a force by which the feed water tube 207 is urged upwardly is reduced or weakened. The water feed tube 207 is rounded by the elasticity of the feed water tube 207 per se. The line 256 within the tube 207 is opened. The water begins to flow. Furthermore, an amount through which the feed water button 227 is pushed downwardly is adjusted whereby the amount of feed water can also be adjusted.

Meanwhile, similarly to the case of the aforesaid feed water tube 207, the suction tube 208 is arranged as follows. That is, the suction button 228 is pushed downwardly by such a large or great force as to overcome the spring 254a. The lateral shank 255a reduces or weakens a force which urges the suction tube 208 upwardly, to open the suction line 257 within the suction tube 208. Thus, an upper surface of the suction button 228 and the lateral shank 255a are moved to a position indicated by two-dot-and- chain line in FIGS. 35 and 37. It is possible to turn ON/OFF the suction and to adjust the quantity of suction. According to the arrangement of the seventh embodiment, the valve unit 206 is possible to be detachably mounted on the endoscope body 205, and the mounting orientations can be selected as shown in FIGS. 34(a) and 34(b). Accordingly, an operator can mount the endoscope in the orientation easy to operate and can operate the endoscope. Further, in case where operation is not required, the endoscope can be dismounted to perform the endoscope examination.

Thus, in addition to the advantage that, similarly to the first embodiment, only combination of the endoscope inserting section and the sheath facilitates formation of the cleaning fluid line, the seventh embodiment has a merit that operability can be improved more than the case where the valve unit is fixed. Accordingly, even for an operation in which delicate operation is required and for an operation which extend to a long period of time, the endoscope is easy to be had. The button operation of the valve unit 206 can easily be performed. The proceeding of the operation can smoothly be performed. Moreover, fatigue of the operator can be reduced.

In connection with the above, in the seventh embodiment, a structure in which the valve unit is detachably mounted on the endoscope body has been described (the position regulation mechanism is provided on the sheath body). However, a structure may be such that the valve unit is detachably mounted on the sheath body. Further, a structure may be such that the valve unit is detachably mounted on both of them.

Figure 38:
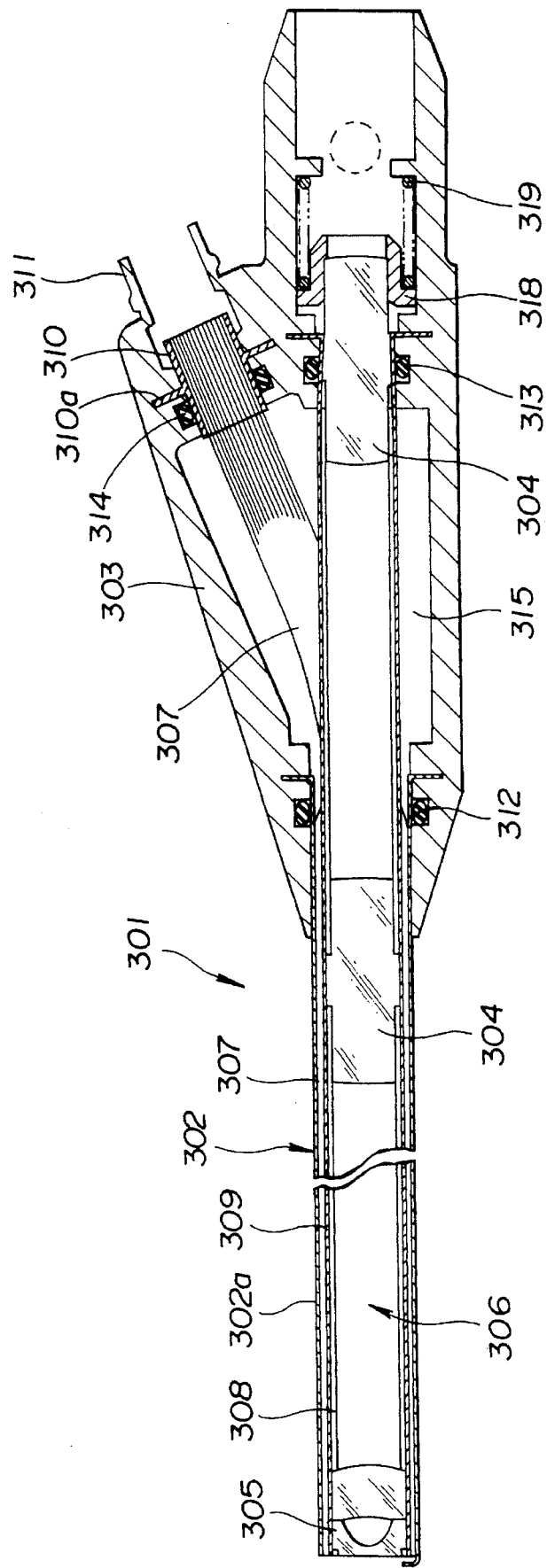
FIG. 38 is a cross-sectional view showing an arrangement of an inserting section of an endoscope according to an eighth embodiment of the invention.
Figure 39:
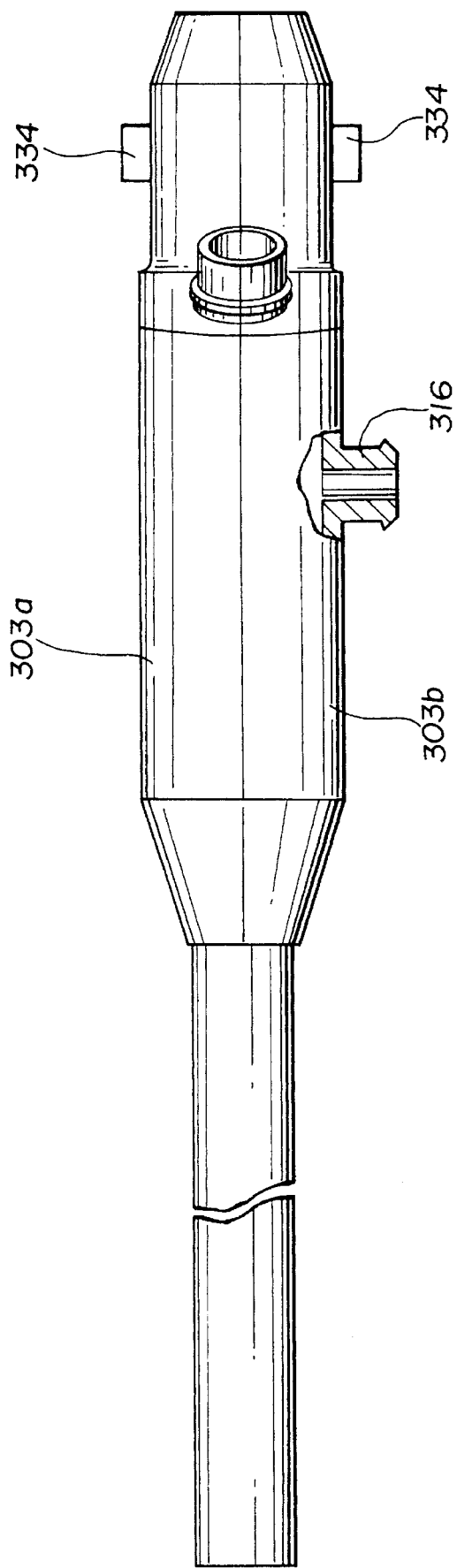
FIG. 39 is a top plan view showing an arrangement of the inserting section of the endoscope according to the eighth embodiment.

FIGS. 38 to 40 show an eighth embodiment of the invention.

The eighth embodiment shows an arrangement example of the endoscope of disposable type in which, after the endoscope as been used, the endoscope is cancelled.

An endoscope 301 according to the embodiment is so arranged as to comprise a rigid elongated inserting section 302 which is inserted into a body cavity or the like, and an endoscope body 303 which is connected to a distal part of an inserting section 302. In case where the endoscope is arranged in consideration of disposability, it is adequate that the body 303 is made of resin.

The inserting section 301 is provided, within an outer tube 302a of the inserting section, with an optical unit 306 including a relay lens 304 and an objective lens 305 and an illumination optical system 307 for transmitting the illumination light so arranged as to bundle plastic fiber, glass fiber or the like around an outer periphery of the optical unit 306, to the distal part. The optical unit 306 is arranged with the relay lens 304 being determined in intervals by interval tubes 308. An objective lens 305 is arranged at a distal part. These relay lens 304 and objective lens 305 are so arranged as to be housed within a pipe-like inner tube 309.

The illumination optical system 306 has a proximal end is arranged such that disconnected or disjointed fibers are caulked so as to be put together into one by a caulking member 310. The caulking member 310 is provided with a flange 310a for fixing the proximal end of the illumination optical system 307 to the body 303. Thus, a distance with respect to a light guide cable outputting end surface which is connected to a light guide base 11 is adapted to be maintained constant by the flange 310a. In this connection, it is desirable that an inputting end surface of the illumination optical system 307 is polished in case of glass, is polished after fusion in case of plastics, or the like, to improve inputting efficiency.

The body 303, and the inserting-section outer tube 302a, the optical unit 306 and the illumination optical system 307 are maintained water-tightly respectively by O-rings 312, 313 and 314. As shown in FIG. 39, the body 303 is adapted to be capable of being split into a pair like 303a and 303b in view of a manufacturing problem, and is integrated by ultrasonic fusion, adhesion or the like. Thus, a chamber 315 is formed water-tightly in the interior by the O-rings 312, 313 and 314 and the body 303. Moreover, a base 316 which is in communication with the chamber 315 is provided in a side of the body 303, as shown in FIG. 39. A tube which performs feed water, feed gas, suction or the like for cleaning the objective lens 305 can be connected to the base 316.

Figure 40A:
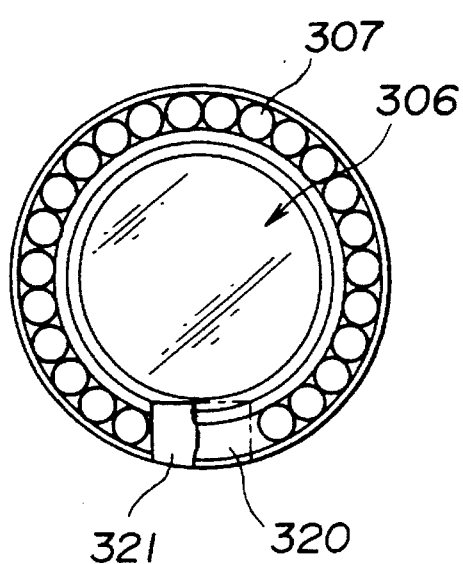
FIG. 40(*a*) and 40(*b*) show an arrangement of a distal part of the inserting section of the endoscope according to the eighth embodiment, FIG. 40(*a*) being a front elevation view as viewed from a forward end.
Figure 40B:
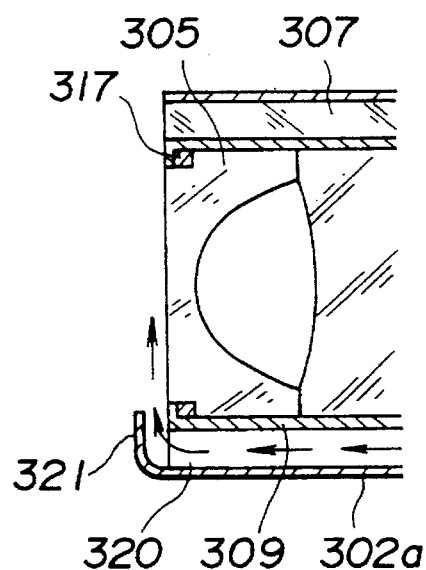

A detailed arrangement of the distal part of the inserting section 302 is shown in FIG. 40(a) and FIG. (b). As shown in FIG. 40(b), the objective lens 305 is exposed to the forward-end surface of the inserting section. A distal part of the inner tube 309 which covers the optical unit 306 is bent or folded approximately 90° along the end surface of the inserting section. A packing 317 is provided between the folded portion of the inner tube 309 and the objective lens 305 so that the water tightness of the optical unit 306 is maintained or retained. Because of this water-tight structure, a spring retainer 318 is provided at the proximal end of the optical unit 306, as shown in FIG. 38. A spring 319 is engaged between the spring retainer 318 and the body 303. The relay lens 304 is pushed forwardly by a biasing force of the spring 319, and a force thereof is transmitted to the objective lens 305. The packing 317 is urged against the inner tube 309. Thus, water tightness is kept or maintained.

As shown in FIG. 40(a), an illumination optical system 307 is arranged around the optical unit 306. A portion in which the fibers are partially lacking is provided whereby a clearance portion 320 is provided. A canopy top 321 which projects in the form of an L-shape so as to be opposed against the opening position of the clearance 320 is formed by the fact that the distal part of the inserting-section outer tube 302a is worked or processed, and is provided. A feed water or suction passage is defined by the clearance 320. A jetting nozzle directed toward the objective lens is formed by the portion of the canopy top 321.

In case where cleaning of the objective lens is performed when the endoscope arranged in this manner is used, feed water liquid for cleaning is fed to the endoscope through the feed water tube by a pressurizing pump, a roller pump or the like. If the water feed tube is connected to the base 316 so that water is fed upon cleaning, the feeding water which enters the chamber 315 from the base 316 passes through the clearance between the inserting-section outer tube 302a, and the inner tube 309 of the optical unit 306 and the illumination optical system 307 travels toward the clearance 320 which opens at the distal part. Thus, the feeding water is led to the distal part. As shown by the arrows in FIG. 40(b), the feed water liquid which flows through the clearance 320 is bent in water feeding direction by approximately 90° or more by the canopy top 321, and is jetted toward the surface of the objective lens 305. Thus, it is possible to remove blood or steam which is adhered to the objective lens.

In connection with the above, the arrangement may also be such that the suction means is connected to the base 316 so that water drops or the like remaining on the surface of the objective lens 305 or the like is sucked through the clearance 320.

As described above, according to the arrangement of the embodiment, the clearances between the inserting-section outer tube 302a, the optical unit 306 and the illumination optical system 307 are used as the passages for water feed and the like, whereby it is possible to easily form the cleaning line. Further, it is not required or it is not necessary to additionally provide the nozzle, the tube and the sheath. Even in the structure having the objective lens cleaning function, it is possible to reduce the cost, and the assembling can also be improved.

Figure 41:
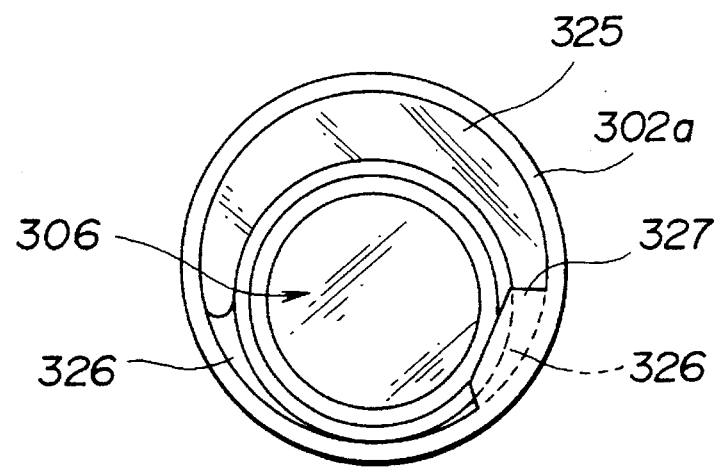
FIG. 41 is a front elevation view showing an arrangement of a distal part of an inserting section of an endoscope according to a ninth embodiment of the invention.

Subsequently, a ninth embodiment of the invention will be described with reference to FIG. 41. The ninth embodiment is a modification in which the arrangement of the inserting section of the endoscope in the eighth embodiment is modified.

The ninth embodiment is an example in which a plastic mold is used in place of the fibers, as the illumination optical system, to form the ninth embodiment. The other fundamental or principle arrangement is similar to that of the eighth embodiment.

Specifically, an optical unit 306 and an illumination optical system 325 made of a plastic mold and having a cross-section which is a crescent shape in cross-section so as to surround the optical unit 306 are incorporated into the interior of the outer tube 302a of the inserting section 302. Further, a clearance 326 is defined between the inserting-section outer tube 302a and the optical unit 306 and the illumination optical system 325. A canopy top 327 for changing or altering an orientation of water flow which is sent from the clearance 326 is provided at a position which is opposed against the opening in the one clearance 326. In this connection, in FIG. 41, the canopy top 327 is provided only on the one clearance 326. However, the canopy tops may be provided correspondingly respectively to both clearances 326.

When water is fed to the endoscope in case where cleaning of the objective lens is performed, the sent feed water liquid passes through the clearance 326, and is led to the distal part. The sent feed water liquid is discharged from the opening in the clearance 326, and is changed in orientation by the canopy top 327. Thus, the sent water liquid is jetted toward the surface of the objective lens 305.

The arrangement of the ninth embodiment can produce advantages similar to those of the eighth embodiment. Since the plastic mold is used in the illumination optical system, a step of bundling the fibers upon assembling is dispensed with as compared with the eighth embodiment. Thus, operation is simple, and it is possible to further improve assembling ability or performance.

Figure 42:
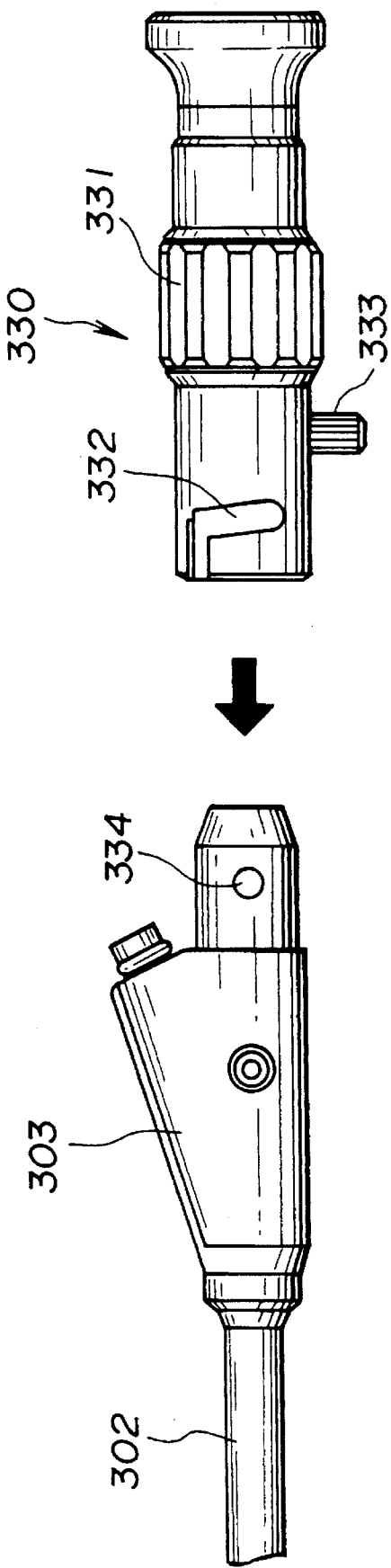
FIGS. 42(*a*) and 42(*b*) are arrangement explanatory views showing an arrangement of the side rearward from a proximal part of the insertion part of the endoscope according to the eighth embodiment.
Figure 42:
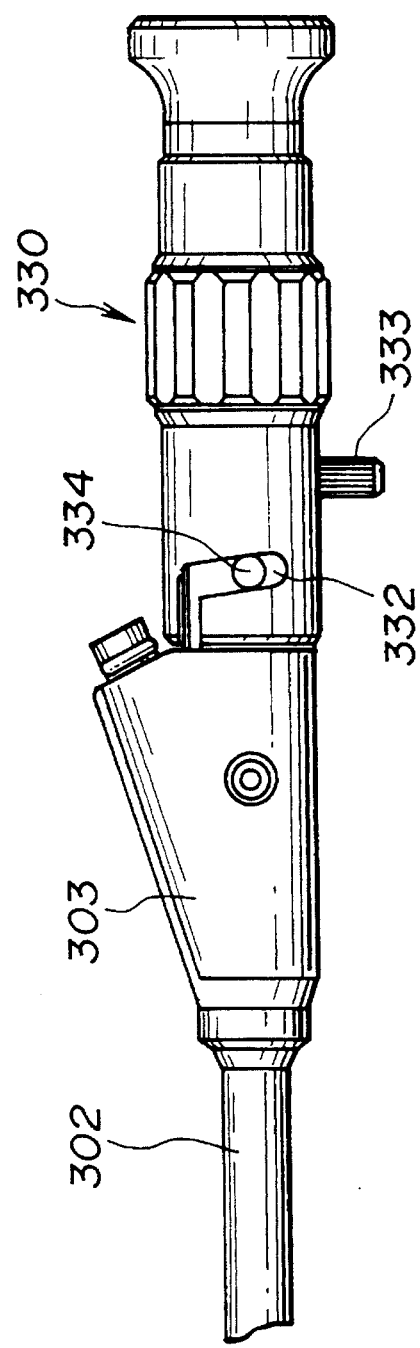

Subsequently, the whole arrangement of the endoscope 301 according to the aforesaid eighth embodiment will by described. FIG. 42(a) and FIG. 42(b) show the arrangement of the endoscope 301 in rear of the inserting-section proximal end.

In the endoscope 301, the lens within the optical unit, the illumination optical system, the body or the like is formed by the plastics in order to come into a disposable type, so that an attempt is made to reduce the cost. However, the plastics are used in the lens, whereby aberration occurs. In case where a glass lens is used in order to take the aberration, it is impossible to reduce the cost at which the glass lens is disposable. For this reason, the embodiment is arranged such that the glass lens portion is made to a reusable type and is provided on the side of the rear end of the endoscope body, and the body and the inserting section of the plastic lens portion are made to a reusable type.

As shown in FIG. 42(a), the endoscope body 303 and the inserting section 302, and the eyepiece adaptor 330 are formed separately from each other. An optical system having a glass lens is arranged within the eyepiece adaptor 330, and a focus ring 331 for focusing is provided within the eyepiece adaptor 330. Moreover, a cam groove or ditch 332 is provided in a connection of the end of the eyepiece adaptor 330 with respect to the endoscope body 303. A knob 333 is provided laterally adjacent to the cam ditch 332.

Meanwhile, as shown in FIG. 39 and FIG. 42(a), a projection 34 which projects laterally and which is engaged with the cam ditch 332 is provided on the proximal end of the endoscope body 303.

When the endoscope body 303 and the eyepiece adaptor 330 are connected to each other, as shown in FIG. 42(b), the projection 334 of the endoscope body 303 is engaged with the cam ditch 332 in the eyepiece adaptor 330 so that the proximal end of the endoscope body 303 is fitted therein. The knob 333 is clamped to rotate the eyepiece adaptor 330. Thus, the projection 334 is fixed to the cam ditch 332 in the projection 334.

As an arrangement which connects the eyepiece adaptor 330 and the endoscope body 303 to each other, an arrangement which connects them to each other by the cam ditch is considered as shown in FIG. 42(b) and, in addition thereto, various dismounting mechanisms which use snap fit, a screw or a magnetic force, and the like are considered.

Figure 43:
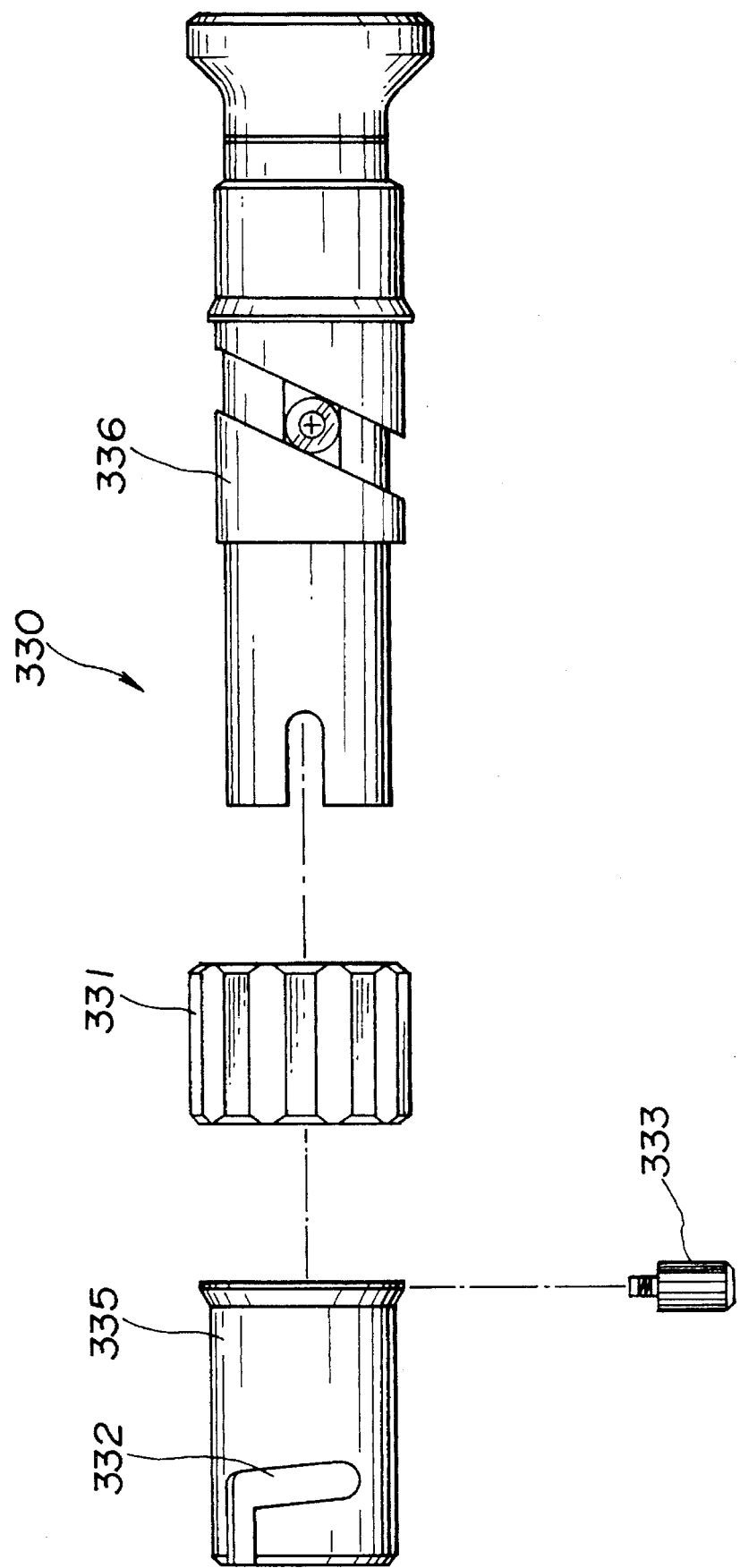
FIG. 43 is an explanatory view showing a state in which an eyepiece adaptor in FIG. 42(*a*)

An exploded view of the eyepiece adaptor 330 is shown in FIG. 43. The arrangement of the eyepiece adaptor 330 is such that, when the knob 333 on the lateral side is disengaged, the connection 335 having therein the cam ditch 332 and the focus ring 331 can be dismounted from the adaptor body 336. Thus, upon cleaning after having been used in the operation or the like, it is possible to disassemble the eyepiece adaptor 330, whereby it is possible to easily or simply clean various parts of the eyepiece adaptor 330 every nook and corner. Accordingly, handling is simple and convenient.

In this manner, the endoscope body and the inserting section and the eyepiece are so formed as to be separate form each other, and only the body and the inserting section are disposable. Thus, it is possible to arrange the disposable portions at low cost. It is realized to make the rigid endoscope to the arrangement which is more suitable for a disposable type.

Figure 44:
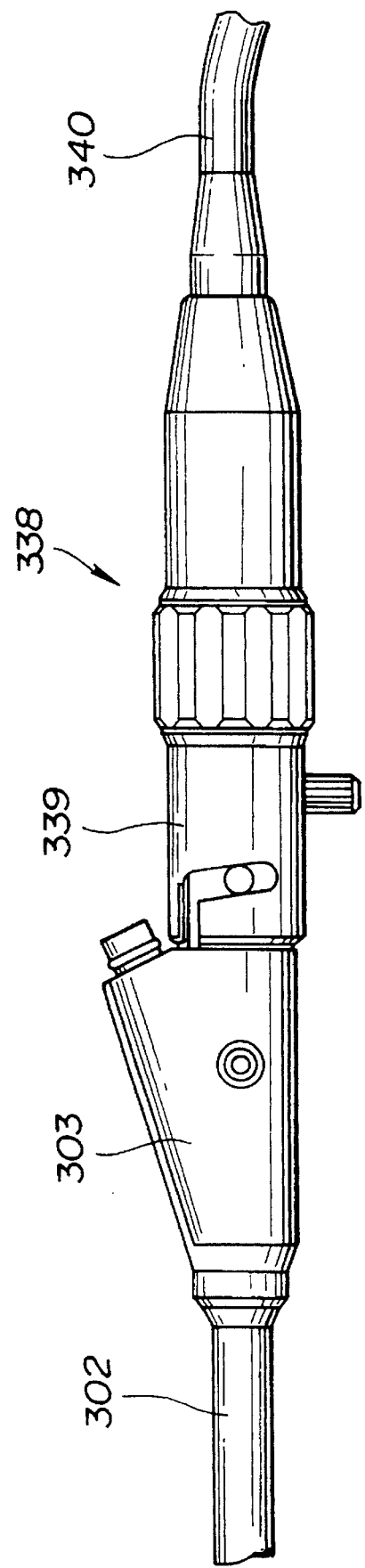
FIG. 44 is an arrangement explanatory view showing a modification of the endoscope in which a disposable portion is separately arranged.

As a modification of the endoscope in which the disposable portions are so arranged as to be separate from each other, as shown in FIG. 44, it is possible also to arrange such that the camera head 338 is detachable with respect to the proximal end of the endoscope body 303. The camera head 338 has an eyepiece unit 339 having a cam groove or ditch whose arrangement is similar to that of the eyepiece adaptor 330. The camera head 338 is provided therein with an image pickup optical system and an image pickup element. The camera head 338 is connected to a camera control unit for performing image-signal processing, through the signal cable 340 which extends from the rearward end thereof.

Also in the present modification, only the body and the inserting section are made to disposable. Thus, it is possible to arrange the endoscope at low cost.

Subsequently, the arrangement of a relay lens and a spacer tube within the optical unit of the endoscope 301 will be described.

Figure 45:
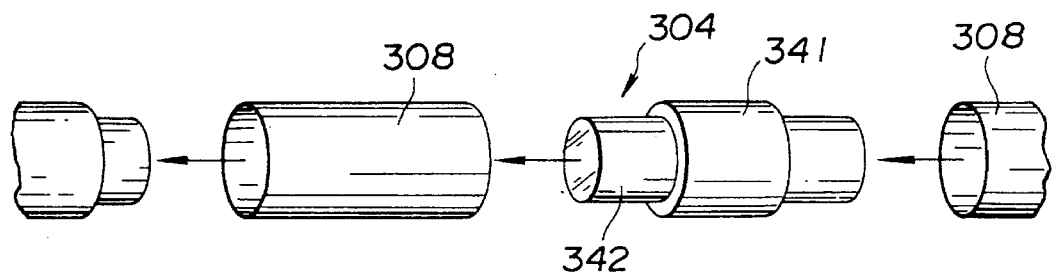
FIG. 45 is an arrangement explanatory view showing an arrangement of a relay lens and a spacing tube within an optical unit of the endoscope according to the eighth embodiment.

If a relay lens 304 and a spacer tube 308 which cooperate with each other to arrange or form the relay optical system in an optical unit 306 of an endoscope 301 shown in FIG. 38 are disassembled, the relay lens 304 and the spacer tube 308 come into an arrangement as shown in FIG. 45. The relay lens 304 has a diameter thereof which is the same as the outer diameter of the spacer tube 308, and comprises a large diameter portion 341 in contact with the inner tube 309, and a reduced diameter portion 342 having a diameter thereof smaller than the large diameter portion 341. An outer diameter of the reduced diameter portion 342 comes into one which is capable of being press-fitted or interfitted with respect to the inner diameter of the spacer tube 308.

When the relay optical system is assembled, the spacer tube 308 is interfitted in the reduced diameter portion 342 of the relay lens 394, whereby the relay lens 304 and the spacer tube 308 are assembled with each other. The relay lens 304 is provided, at both ends thereof, with the reduced diameter portion 342. Accordingly, the relay lens 304 ad the relay lens are combined with each other subsequently like blocks, whereby it is possible to easily assemble the relay optical system. A relay optical unit in which all the relay lens 304 and the spacer tube 308 are assembled with each other to make a columnar shape is integrally inserted into the inner tube 309.

The relay lens and the spacer tube are arranged in this manner. Thus, in the prior art, the spacer tube and the relay lens are so assembled with each other as to be put into the inner tube carefully one by one. However, the interior relay lens and spacer tube are first integrally assembled with each other exteriorly and, subsequently, the integrated relay optical system is inserted into the inner tube so that it is possible to assemble the optical unit. Thus, it is possible to perform assembling of the optical unit easily. It is possible to remarkably reduce the assembling time. Furthermore, it is also possible to reduce the cost.

Figure 46:
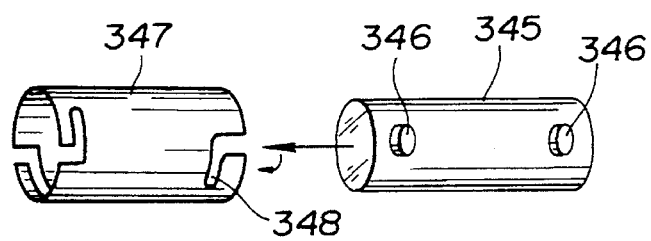
FIG. 46 is an arrangement explanatory view showing a first modification of the relay lens and the spacing tube.

Hereunder, a modification of the arrangement of the relay lens and the spacing tube is shown. FIG. 46 shows a first modification of the relay lens and the spacing tube.

The relay lens 345 is provided, on the sides thereof, with four (4) ribs 346 in sum, which project in the form of a columnar shape, at positions which are opposed against each other at both ends thereof. Meanwhile, the spacer tube 347 is provided with a cam ditch 348 with which the ribs 346 are engaged. The arrangement is such that, when the relay lens 345 and the spacer tube 347 are connected to each other, the rib 346 is engaged with the cam ditch 348 and is fixed thereto.

When the relay optical system is assembled, the rib 346 of the relay lens 345 and the cam ditch 348 of the spacer tube 347 are engaged with each other, and are successively assembled with each other. Thus, it is possible to easily assemble the relay optical system unit.

Figure 47:
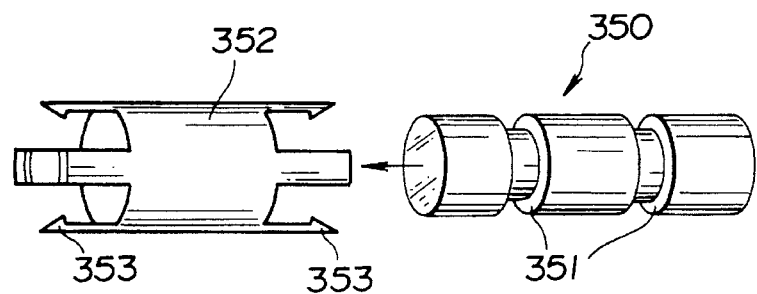
FIG. 47 is an arrangement explanatory view showing a second modification of the relay lens and the spacing tube.

FIG. 47 shows a second modification of the relay lens and the spacer tube.

The relay lens 350 is provided, at both ends thereof, with engaging ditches 351 in the form of an orbit. Meanwhile, the spacer tube 352 is formed with a pawl 353 which is engaged with the engaging ditch 351. By these elements, a connecting mechanism of a snap fit time is formed. The arrangement is such that, when the relay lens 350 and the spacer tube 352 are connected to each other, the pawl 353 is engaged with the engaging ditch 351 and is caught thereby so that the pawl 353 is fixed.

When the relay optical system is assembled, as the relay lens 350 is inserted into the spacer tube 352, the pawl 353 is caught at the engaging groove 351 so that the relay lens 350 and the spacer tube 352 are fixed. Similarly, the relay lens 350 and the spacer tube 352 are successively assembled with each other, whereby it is possible to easily assemble the relay optical system unit. In the present example, because of the connecting mechanism of snap fit type, assembling is more simplified.

Figure 48:
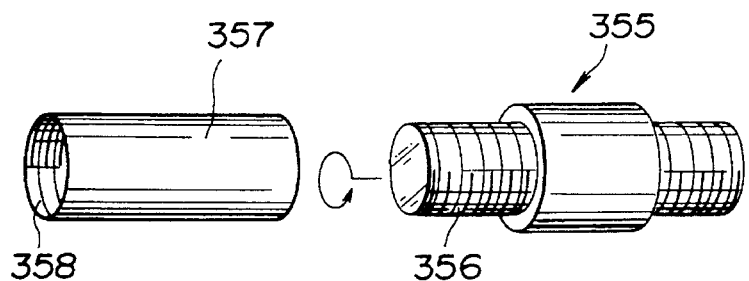
FIG. 48 is an arrangement explanatory view showing a third modification of the relay lens and the spacing tube.

FIG. 48 shows a third modification of the relay lens and the spacer tube.

The relay lens 355 is formed with a large diameter portion and a reduced diameter portion, similarly to the arrangement illustrated in FIG. 45. Male threads 356 are provided in the reduced diameter portion at both ends of the relay lens 355. Meanwhile, the spacer tube 357 has an inner periphery thereof which is provided with female threads 358. The male threads 356 are threadedly engaged with the female threads 358 so as to be fixed.

When the relay optical system is assembled, the male threads 356 of the relay lens 355 are screwed into the female threads of the spacer tube 357 so that the relay lens 355 and the spacer tube 357 are connected to each other. Similarly, the relay lens 355 and the spacer tube 357 are successively connected to each other. Thus, it is possible to easily assemble the relay optical system unit.

Thus, also in the above modifications, the relay optical system unit, comprising relay lenses and spacer tubes, can be assembled easily and in a short time, thereby enabling the apparatus to be constructed at low costs.

As described above, according to the eighth and ninth embodiments of the present invention, an endoscope can be constructed at low costs and in a structure having a satisfactory assembling performance. Further, the passage or nozzle for cleaning can be formed in a simple structure, thereby providing the apparatus with an objective cleaning function easily and at low costs. Thus, the apparatus can have a structure suitable for throwaway-type uses.

A tenth embodiment of the present invention will be described with reference to FIGS. 49 through 53.

Figure 49:
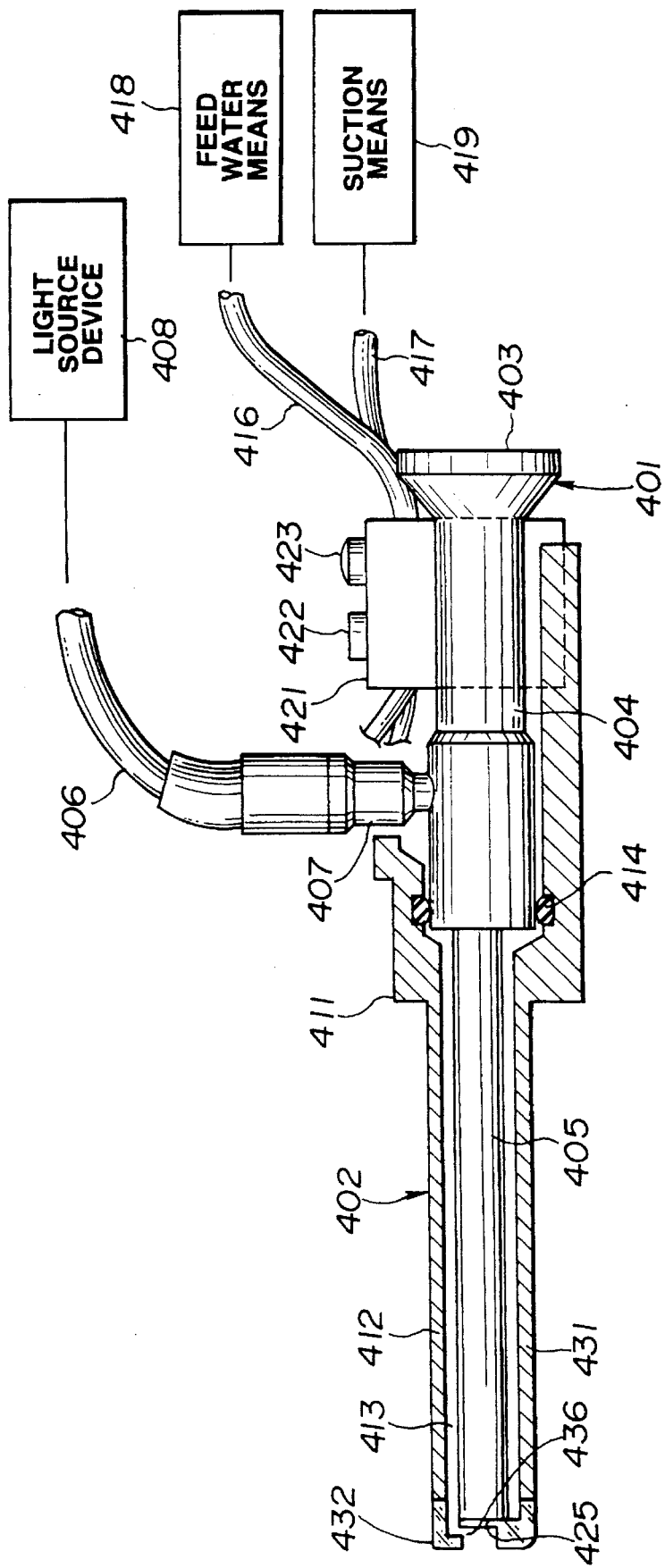
FIG. 49 is an explanatory view showing a whole schematic arrangement of an endoscope apparatus according to a tenth embodiment of the invention.

FIG. 49 schematically shows the overall construction of the endoscope apparatus. In FIG. 49, numeral 401 indicates a rigid endoscope, and numeral 402 indicates an anti-fogging sheath device to be attached to the rigid endoscope 401. The rigid endoscope 401 comprises an endoscope body 404 equipped with an eyepiece section 403 containing an eyepiece, and an endoscope insertion section 405 consisting of a rigid straight tube. The endoscope body 404 is provided with a connector 407 for connecting it with a light guide cable 406. The light guide cable 406 is connected to an illuminating light source device 408.

The anti-fogging sheath device 402 comprises a sheath body 411 to be fitted onto the endoscope body 404 of the rigid endoscope 401, and a sheath insertion section 412 consisting of a cover tube coaxially fitted onto the endoscope insertion section 405 of the endoscope 401. The inner diameter of the sheath insertion section 412 is larger than the outer diameter of the endoscope insertion section 405. As a result, when the sheath insertion section 412 is fitted onto the endoscope insertion section 405, a fluid supply duct 413 is defined between them. The duct 413 communicates with a nozzle section 436 which is formed at the forward end of the sheath insertion section 412 in the manner described below.

A ring-shaped seal member 414 is attached to the inner surface of the sheath body 411. The seal member 414 is closely fitted into the gap between the inner surface of the sheath body 411 and the outer surface of the endoscope 404 to airtightly or fluid-tightly stop the section of the duct 413 nearer to the operator. The seal member 414 is formed, for example, of an elastic material. This seal member consists of a silicon rubber member, elastic O-ring member, etc. In particular, an elastic synthetic resin is preferable for its material.

As in the seventh embodiment described above, in the sheath body 411, one or a plurality of bases (not shown) are provided at positions nearer to the forward end than the position of the seal member 414 in such a way as to communicate with the duct 413. In this embodiment, two or more bases are provided. One base is connected to a feed water tube 416, and the other base is connected to a suction tube 417. The feed water tube 416 leads to a feed water means (a feed water device) 418, and the suction tube 417 leads to a suction means (a suction device) 419.

The fluid passages of the feed water tube 416 and the suction tube 417 are selectively switched through operation of a feed water button 422 and a suction button 423 provided on a valve unit 421, whereby the water feeding or suction through the tubes 416 and 417 can be turned on and off, and, further, the flow rate therein can be adjusted. Thus, the water feeding operation and sucking operation for the duct 413 can be controlled. Further, it is also possible to utilize the duct 413 in feeding air from the nozzle section 436. As in the seventh embodiment, the valve unit 421 is detachably mounted on the sheath body 411.

A light guide (not shown) is provided within the endoscope 401. This light guide leads illuminating light, which is led through the light guide cable 406, to an illumination window formed in a forward end surface 425 of the endoscope, thereby illuminating the section to be observed in the body cavity. Further, the endoscope forward end surface has an observation window having an objective lens and formed beside the illumination window. Further, the endoscope contains an observed-image transmission optical system (not shown) for transmitting an image of the viewing field formed by the objective lens of the observation window. The image transmitted through the transmission optical system can be observed through the eyepiece section 403. Further, the endoscope 401 used in this embodiment is not restricted to a rigid type one. Any type of endoscope, e.g., soft type, electronic type, etc., is applicable to this embodiment.

Figure 50:
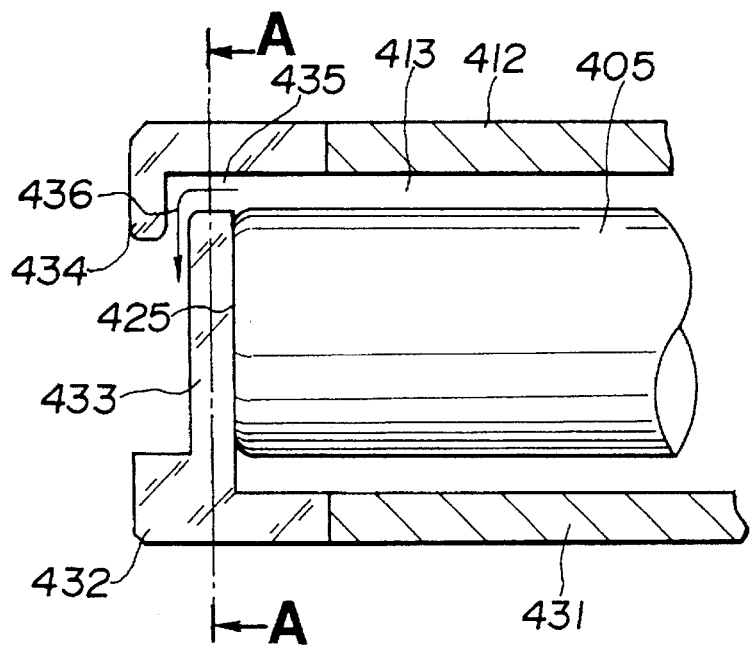
FIG. 50 is a longitudinal cross-sectional view showing the neighborhood of a distal part in the endoscope apparatus according to the tenth embodiment.
Figure 51:
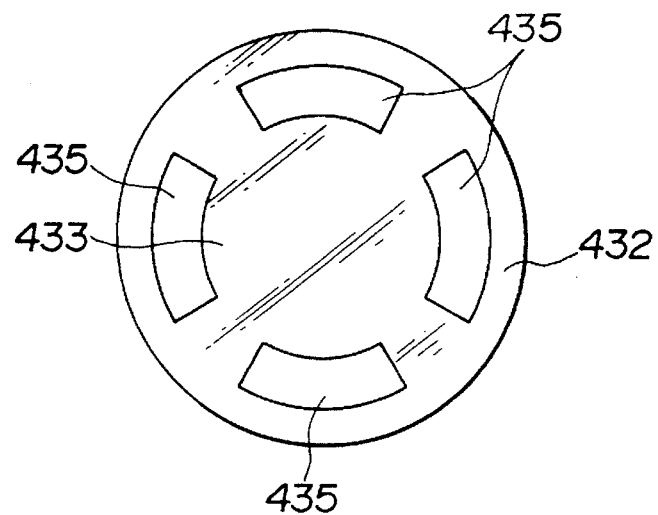
FIG. 51 is a cross-sectional view taken along a line A—A in FIG. 50.

The sheath insertion section 412 of the anti-fogging sheath device 402 is formed by joining the forward end of a sheath pipe member 431 to a forward end cover member 432 having the same outer diameter as the sheath pipe member 431. As shown in FIGS. 50, 51, 52(*a*) and 52(*b*), the forward end cover member 432 consists of an integrally molded, short cylindrical member generally having a bottom and formed of a resin which is optically transparent. Its flat bottom section (central section) constitutes a transparent observation window 433. Formed in the periphery of the observation window 433 is a cylindrical flange section 434 slightly protruding forward beyond it. It is desirable that the inner diameter of the flange section 434, formed as a cylinder, be not so large as to interfere with the viewing field of the endoscope 401.

In the forward end cover member 432, that end where the flange section 434 is formed will be referred to as the forward end, and the end opposite thereto as the base end. At least one hole 435 not reaching the flange section 434 and directly communicating with the duct 413 extends from the base end. In this embodiment, four holes 435, upper, lower, right and left ones, are provided.

As shown in FIG. 52(*b*), each of the holes 435 has at its forward end an opening which is bent toward the central axis of the forward end cover member 432, thereby forming a nozzle section 436 extending from the base end and bent at right angles at the forward end. The forward end opening of the nozzle section is directed toward the surface of the observation window 433 and connected thereto.

A plurality of short rearward projections 437 are formed in the rear periphery of the forward end cover member 432. The radial thickness of the projections 437 is equal to the wall thickness of the sheath pipe member 431. As shown in FIG. 52(*a*), the projections 437 of this embodiment are arranged at equal intervals between the holes 435, in an alternate order. The number of projections 437 is not limited to four. It may also be one, two or three or more.

Although the holes 435 and the projections 437 have a substantially rectangular longitudinal sectional configuration, their inner and outer sides are in the circumference of the same circle having its center in the central axis of the forward end cover member 432. The circle has a size which coincides with the inner diameter circle of the sheath pipe member 431. Further, as shown in FIG. 52(*a*), although the right and left sides of the holes 435 and the projections 437 are flat, they exhibit a wedge-like configuration smaller on the inner side when seen in cross section. The diameter of the circle connecting the inner sides of the projections 437 is limited to that in the above example. However, it is necessary for the diameter to be at least somewhat larger than the outer diameter of the endoscope insertion section 405 fitted into the sheath insertion section 412.

As shown in FIG. 53, a plurality of cutouts 438 are formed at equal intervals at the forward end of the sheath pipe member 431 to be connected to the forward end cover member 432, the cutouts 438 having a configuration corresponding to that of the projections 437 for butt-joint. When joining the forward end cover member 432 with the sheath pipe member 431, the forward end cover member 432 and the sheath pipe member 431 are coaxially butted against each other so as to fit the projections 437 into the cutouts 438. Due to the wedge-like configuration of the projections 437 and the cutouts 438, the forward end cover member 432 and the sheath pipe member 431 are of necessity coaxially aligned with each other. In this way, at least a pair of protrusion 437 and cutout 438 are fitted together and the joint between the forward end cover member 432 and the pipe member 431 is secured by adhesion, fusion, etc.

The resin of which the forward end cover member 432 is formed is a transparent one, for example, methacrylic resin (PMMA) or polycarbonate resin (PC). Further, an anti-fogging processing is performed at least on the transparent portion of the observation window 433 of the forward end cover member 432.

The anti-fogging processing may consist, for example, of resin coating, pellet mixing, or sheet-like member gluing. It is desirable that this anti-fogging processing be performed on both sides of the observation window portion 433 in the forward end cover member 432. The anti-fogging processing will be described in more detail. Examples of the coating process include vacuum deposition, dipping, spin coating, etc. In vacuum deposition, a high-polymer-type material having hydrophilic and hydrophobic groups is evaporated on a transparent member in a vacuum to form a film. In dipping, such a transparent member is immersed in a processing liquid to form an anti-fogging layer. In spin coating, the processing liquid material is dripped onto a rotating transparent member to form an anti-fogging layer. In pellet mixing, a surface active agent is mixed in pellets of a plastic molding material; after molding, a film of hydrophilic groups is formed on the surface of a transparent member. In the method in which a sheet-like material is glued, an anti-fogging film in the form of a thin sheet, prepared by the coating or pellet mixing, is glued to the surface of a transparent member.

By such anti-fogging processing, what is called an anti-fogging coat or water absorptive coat is obtained. Due to the anti-fogging processing, fine droplets of water adhering to the surface of a transparent member, which water, if allowed to remain in the form of droplets, would cause fogging, are dispersed in a uniform, film-like state to cover the surface of the transparent member, thereby removing or preventing fogging.

The operation of this endoscope apparatus will now be described. In the state in which a defogging sheath device 402 is attached to a rigid endoscope 401 as illustrated in FIG. 49, an observation window 433 of a forward-end cover 432 of the sheath device 402 is closely bonded to an endoscope end surface 425 of an endoscope insertion section 405 provided with an observation window and an illumination window next to each other, as shown in FIG. 50. The endoscope insertion section 405 is located on a plurality of projections 437 of a forward-end cover 432 or on the inner surface of a pipe 431. The inner surface of the observation window 433 subjected to the defogging treatment is watertightly placed on the endoscope end surface 425. With such a construction, illumination and observations are performed with the endoscope 401 through the transparent observation window 433.

When observations are hampered by dirt or waterdrops adhered to the observation window 433, a cleaning liquid blows against the observation window 433 to remove the waterdrops or dirt. More specifically, a feed water button 422 of a valve unit 421 is depressed to perform the feed liquid operation so as to allow a cleaning fluid flowing through a pipe 413 formed between the endoscope insertion section 405 and the sheath insertion section 412 to inject into the outer surface of the observation window through a nozzle 436. After cleaning, the fluid, such as waterdrops, remaining on the outer surface of the observation window 433 can be removed by means of the suction by depressing a suction button 423 of the valve unit 421 or by means of gas fed from other feed means through the nozzle 436. Such an operation can be performed while the endoscope remains within the body. Even when the endoscope stained with blood, or the like, is cleaned, it can be prevented from fogging, thereby ensuring a 100% clear vision and shortening an operation time without requiring the removal of the endoscope 401 from a body cavity.

According to the construction of this embodiment, the projections 437 of the forward-end cover 432 are fit into notches 438 of the pipe 431, thereby ensuring reliable and simple bonding of both components. The forward-end cover 432 provided with the projections 437 is bonded to the thin-walled pipe 431 provided with the notches 438, thereby guaranteeing the bonding strength. As shown in FIG. 52(*a*), the inner edges of holes 435 and a flange 434 of the forward-end cover 432 are aligned along the axis of the insertion section, and thus, the cover 432 can be easily released from a mold when formed.

This embodiment shows that a sheath provided with a defogging-treated transparent portion is attached to the front surface of the endoscope observation window and can be easily replaced by a new one when the old sheath is no longer effective in protecting the observation window from fogging, thus ensuring 100% defogging effects. As described above, the sheath device of this embodiment is simple in construction, thereby easily obtaining an inexpensive endoscope apparatus free from fogging.

The nozzle is formed at the forward-end cover of the sheath, and the endoscope insertion section and the sheath are simply combined to form a cleaning fluid passage easily. The observation window is cleaned through this cleaning nozzle so as to remove dirt or eliminate fog. Also, the cleaning fluid passage is formed only when the endoscope insertion section and the sheath are combined. A suction passage is thus free from being clogged with dirt, or the like, and the sheath is detached from the endoscope insertion section so that the endoscope and the sheath can be easily cleaned and sterilized, thus keeping them clean.

An eleventh embodiment of the present invention will now be explained with reference to FIGS. 54(*a*) and 54(*b*).

The eleventh embodiment can be accomplished by modifying the construction of the forward end of the insertion section of the defogging sheath device shown in the tenth embodiment. That is, an exchangeable transparent plate is provided with the forward end of the insertion section.

The defogging sheath device is provided with a flange 442 projecting toward the center axis at the end of a sheath insertion section 441 formed of a pipe 440. A groove 444 is also arranged inside the flange 442 toward the center axis thereof so as to provide a space for forming a nozzle 443. The defogging-treated transparent plate 447 as discussed above is adapted to be sandwiched between the flange 442 of the sheath insertion section 441 and the endoscope end surface 425 of the endoscope insertion section 405.

Figure 54:
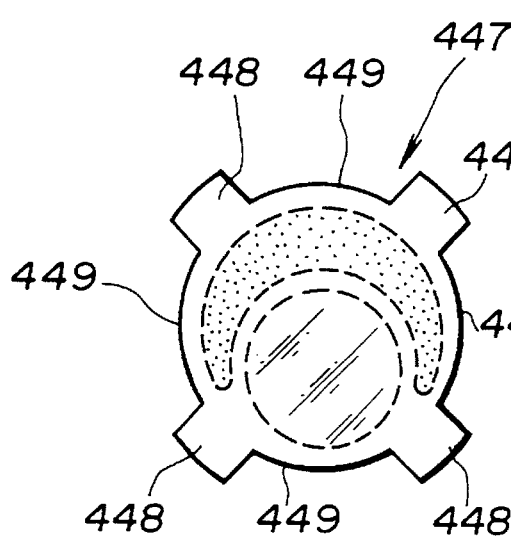
FIG. 54(*a*) is a longitudinal cross-sectional view of a distal part of an endoscope apparatus according to an eleventh embodiment of the invention.
Figure 54:
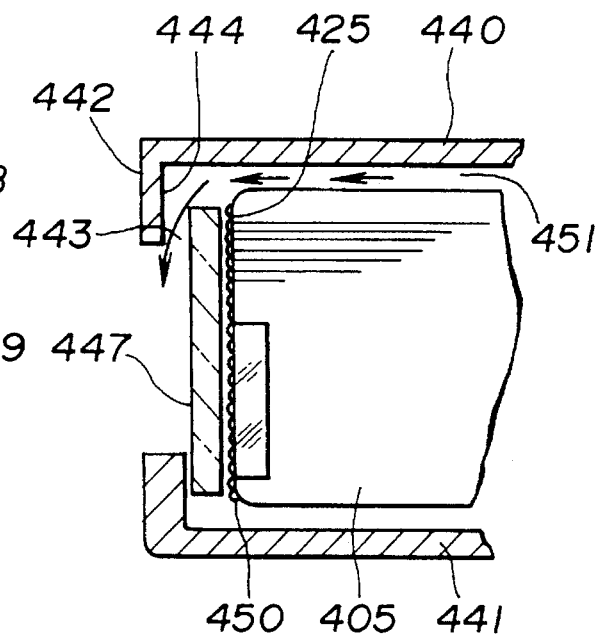

As shown in FIG. 54(*b*), a plurality of projections 448 and depressions 449 are alternately arranged on the outer periphery of the transparent plate 447. The projections 448 are sized small enough to be fit into the internal diameter of the sheath insertion section 41. The bottom of the depressions 449 has substantially the same dimensions of the outer periphery of the endoscope insertion section 405. The diameter of the circle obtained by plotting the apexes of the projections 448 is smaller than the internal diameter of the flange 442. The flange 442 of the sheath insertion section 441 abuts against the projections 448 of the transparent plate 447 so as to allow the transparent plate 447 to press against the endoscope end surface 425 so that water would not enter a clearance between the transparent plate 447 and the endoscope end surface 425. Such a clearance has been filled with water or a transparent adhesive 450. The adhesive 50 may be a transparent high-adherent water soluble material, a silicon material, or the like.

The defogging sheath device constructed as described above is assembled by inserting the endoscope insertion section 405 into the sheath insertion section 441 from the operator's side, as illustrated in FIG. 54(*a*). As in the foregoing embodiments, a passage 451 is formed between the sheath insertion section 441 and the endoscope insertion section 405 so as to communicate with the nozzle 443.

When the cleaning water flows into the passage 451 as described above, it flows onto the outer surface of the transparent plate 447 through the passage 451 via the nozzle 443 formed by the depressions 449 of the transparent plate 447 and the groove 444 of the flange 442. A partial vacuum is applied to the passage 451 so as to allow the waterdrops on the outer surface of the transparent plate 447 to flow backward to the passage 451 and to be sucked out toward the operator.

The transparent plate 447 is simple in construction and is thus manufactured at low cost so that it can be replaced by a new one in every operation. This transparent plate 447 is disposed after use. Alternatively, it may be reused after sterilizing. Although water runs on the transparent plate 447, it can be protected from fogging since the surface thereof is subjected to a defogging treatment. The defogging sheath device of this embodiment is simple in construction, and it is easy to replace the transparent plate 447 which can be separated from the sheath insertion section 441.

The transparent plate 447 is placed in a known sheath, thereby also enabling the provision of an inexpensive endoscope apparatus which is free from fogging and is capable of cleaning the outer surface of an objective lens of the observation window stained with blood, or the like.

The adhesive 450 is filled with a clearance between the transparent plate 447 and the endoscope end surface 425, thereby easily and reliably maintaining liquid tightness between the endoscope end surface 425 and the transparent plate 447.

As described above, a defogging-treated transparent plate is attached to the front surface of the endoscope observation window. This transparent plate is adjusted to be disposable or usable for a few times and to be easily replaced by a new one at low cost when its defogging advantage is no longer effective, thereby maintaining the constantly good defogging effect. The sheath device of this embodiment is simple in construction, and accordingly, an endoscope apparatus free from fogging can be obtained at low cost. When such a defogging advantage ceases to be effective or weakened, the old transparent plate can be simply replaced by a newly defogging-treated plate, thereby constantly ensuring clear viewing fields.

Figure 55:
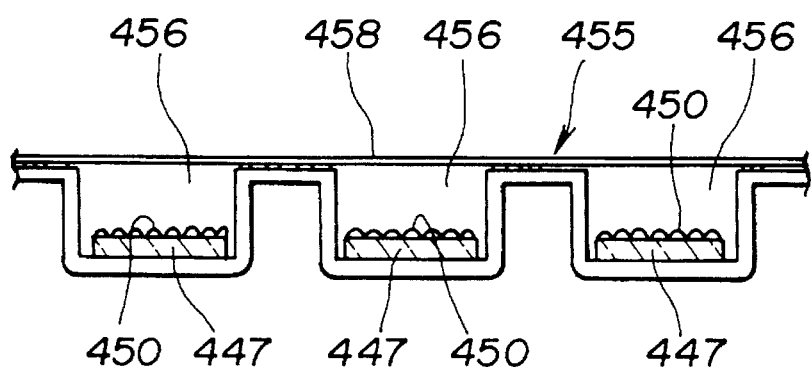
FIG. 55 is a cross-sectional view showing a container which accommodates the transparent plate in the eleventh embodiment of the invention.

FIG. 55 illustrates an example of the construction of a container 455 for accommodating the transparent plates 447. The container 455 is constructed to comprise accommodating chambers 456 which are arranged in series and are each formed of a recess for accommodating each transparent plate 447 one surface of which is coated with the adhesive 450 so as to be bonded to the endoscope end surface 425. An opening of each of the accommodating chambers 456 is covered with a detachable sterilizing cover 458. The container 455 may comprise only one accommodating chamber 456. The container 455 is sterilizable therein and the transparent plate 447 has underwent a sterilizing treatment.

The defogging-treated transparent plate 447 is accommodated into the accommodating chamber 456 of the container 455 in the state in which the surface coated with the adhesive 450 faces upward. Hence, the sterilizing cover 458 is removed and the endoscope insertion section 405 is inserted into the accommodating chamber 456 so as to allow the adhesive 450 to be in contact with the endoscope end surface 425, thereby easily affixing the transparent plate 447 to the endoscope end surface 425. The endoscope insertion section 405 having the transparent plate 447 affixed thereto is inserted to the sheath insertion section 441 and is provided for use.

Figure 56:
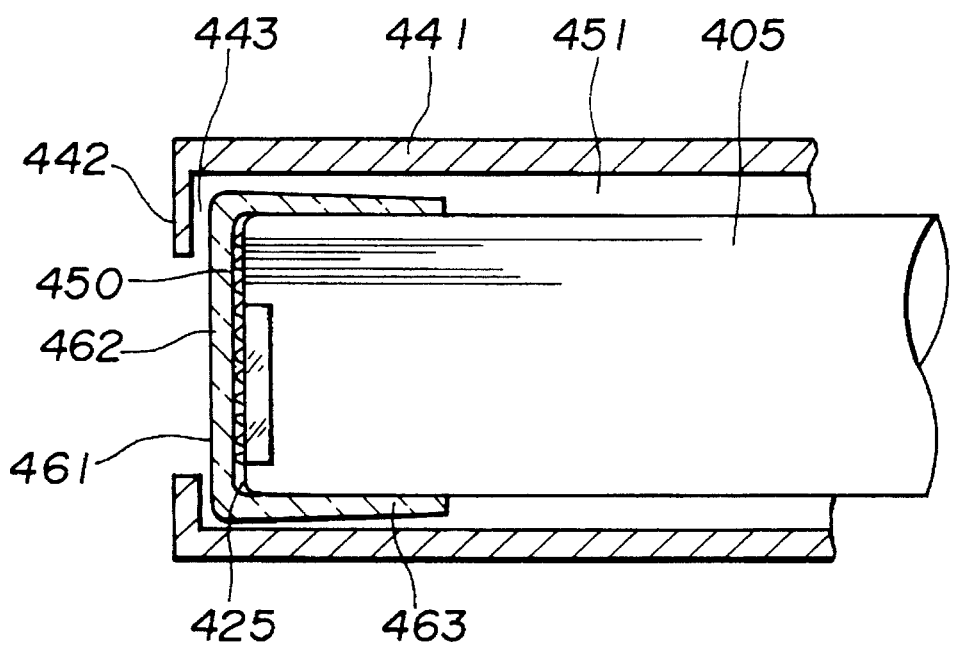
FIG. 56 is a longitudinal cross-sectional view of a distal part of an endoscope apparatus according to a twelfth embodiment of the invention.

A twelfth embodiment of the present invention will now be described with reference to FIG. 56.

The twelfth embodiment, as well as the eleventh embodiment, is accomplished by modifying the construction of the insertion forward-end portion of the defogging sheath device. It is modified such that an exchangeable cap-like transparent member is provided for the insertion forward-end. An explanation of the construction of the same components as those shown in the eleventh embodiment will be omitted.

In this embodiment, the cap-like transparent member 461 is prepared in place of the foregoing transparent plate 447 and covers the forward end of the endoscope insertion section 405 so as to be clamped between the flange 442 of the sheath insertion section 441 and the endoscope end surface 425, as in the eleventh embodiment. The cap-like transparent member 461 comprises an optically flat bottom 462 subjected to a fogging treatment and edge portions 463 having the internal diameter slightly greater than the external diameter of the endoscope insertion section 405.

Figure 57:
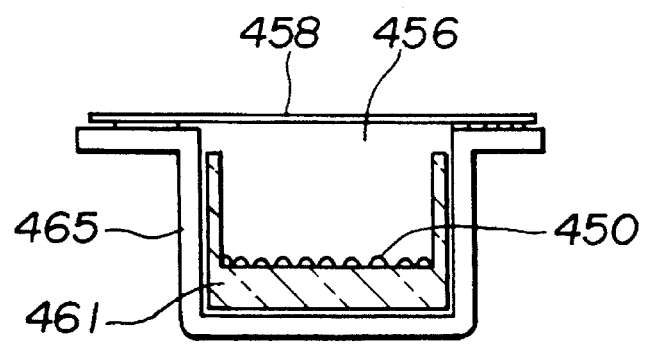
FIG. 57 is a cross-sectional view showing a container which accommodates the transparent plate in the twelfth embodiment of the invention.

A container 465 for accommodating this cap-like transparent member 461 is shown in FIG. 57. The cap-like transparent member 461 is accommodated into the accommodating chamber 456 of the container 465, the inner surface of the transparent member 461 coated with the adhesive 450 facing upward. The opening of the accommodating chamber 456 is covered with the detachable sterilizing cover 458. The container 456 is kept to be sterilizable therein.

The sterilizing cover 458 for the container 465 is removed and the endoscope insertion section 405 is inserted into the recess of the container 465 so as to allow the cap-like transparent member 461 to be affixed to the endoscope end surface 425. The endoscope insertion section having the cap-like transparent member 461 affixed to the forward end thereof is inserted and fixed in the sheath insertion section 441.

Without the application of the adhesive 450 to the transparent plate 447 of the foregoing eleventh embodiment or the cap-like transparent plate 461 of the twelfth embodiment, there is the possibility of producing fog between the endoscope and the transparent plate or the cap-like transparent member. Accordingly, it is necessary to intimately contact the two components or to fill the sterilized water into a clearance therebetween. In contrast thereto, in this embodiment, the transparent plate 447 or the cap-like transparent member 461 is coated with the adhesive 450, thereby making preparations in a short time.

Further, in this embodiment, the transparent member provided for the forward end of the sheath insertion section is formed in a cap shape, thereby preventing possible play with the endoscope insertion section or the sheath insertion section.

An explanation will now be given of a thirteenth embodiment of the present invention with reference to FIGS. 58, 59(a) and 59(b).

The thirteenth embodiment is an example achieved by applying the construction of the foregoing eleventh embodiment to a channeled endoscope.

Figure 58:
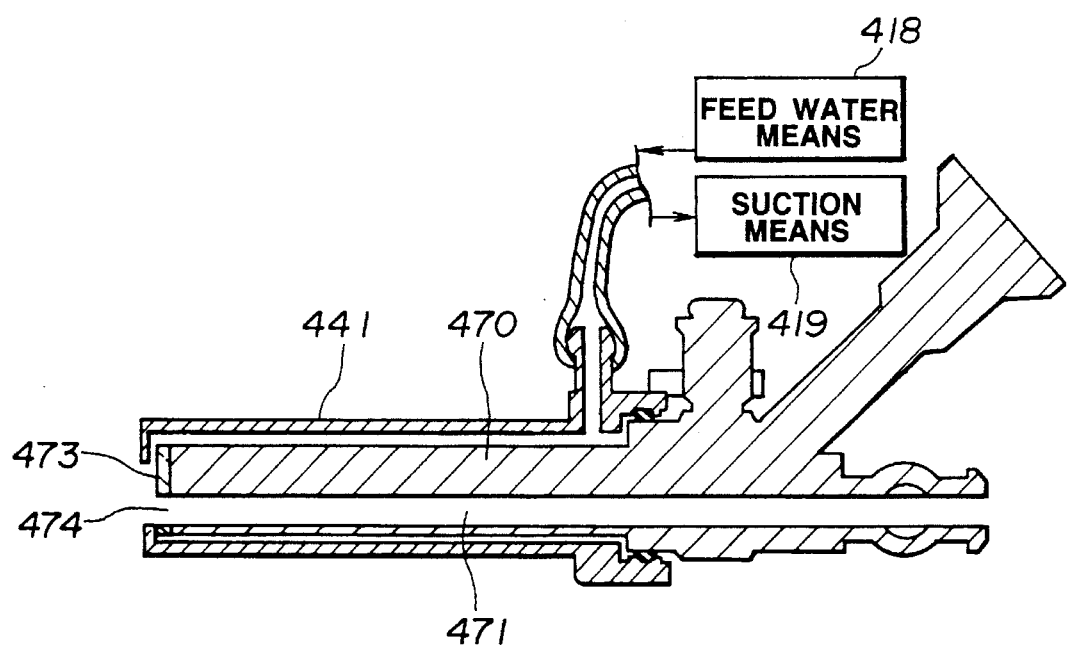
FIG. 58 is a cross-sectional view of an endoscope apparatus according to a thirteenth embodiment of the invention.
Figure 59B:
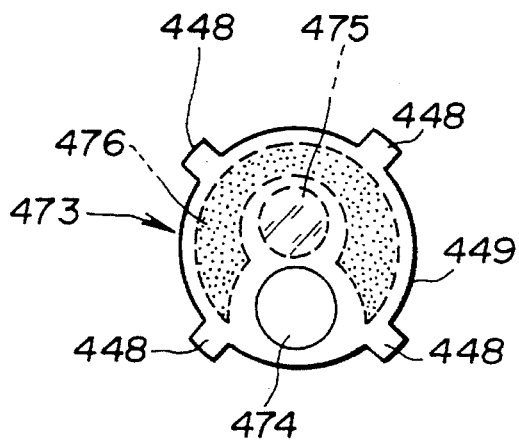
FIG. 59(*a*) is a cross-sectional view of the endoscope apparatus according to the thirteenth embodiment.
Figure 59A:
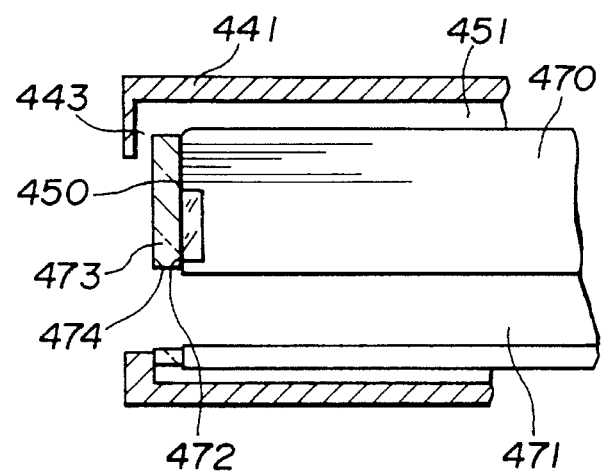

As shown in FIGS. 58 and 59(a), a channel 471 is axially arranged for an endoscope insertion section 470, and a transparent plate 473 to be attached to an endoscope end surface 472 is provided with an opening 474 positioned corresponding to an opening at the forward end of the channel 471, the dimensions of the opening 474 being equivalent to or slightly greater than that of the channel 471.

Since the endoscope insertion section 470 of this embodiment is provided with the channel 471, an observation window 475 is eccentrically placed on the endoscope end surface 472, as shown in FIG. 59(b). On the other hand, an illumination window 476 generally formed in a crescent shape is placed away from the channel 471 and the observation window 475. The constructions of the other components are similar to those in the eleventh embodiment.

The transparent adhesive 450 adheres to one surface of this transparent plate 473, which is thus intimately connected to the endoscope end surface 472. The endoscope insertion section 470 having the transparent plate 473 attached thereto is inserted and fixed into the sheath insertion section 441. In this embodiment, a treatment tool (not shown) is inserted into the channel 471 so as to perform various treatments. Such a treatment tool (not shown) inserted through the channel 471 reaches a section to be treated through the opening 474 of the transparent plate 473.

According to this embodiment, it is possible to perform a treatment through the channel 471 of the endoscope while observing a clear vision free of fog. As a result, the effects accomplished in the eleventh embodiment can be obtained for the endoscope apparatus formed by assembling the channeled endoscope and the sheath.

A description will now be given of a fourteenth embodiment of the present invention with reference to FIGS. 60(a), 60(b), 61(a) and 61(b).

The fourteenth embodiment is an example of another construction of the sheath insertion section of the defogging sheath device.

Figure 60A:
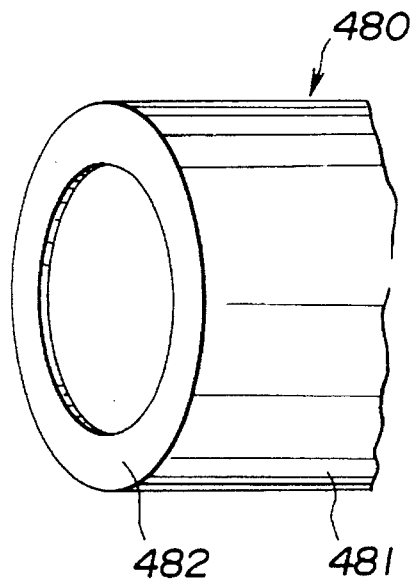
FIG. 60(*a*) is a perspective view of a sheath distal part of an endoscope apparatus according to a fourteenth embodiment of the invention.
Figure 61A:
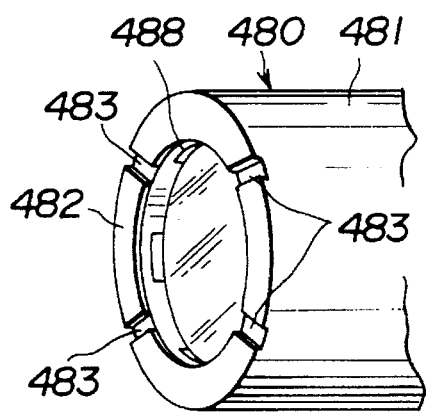
FIG. 61(*a*) is a perspective view of a distal part of the endoscope apparatus according to the fourteenth embodiment.

As illustrated in FIG. 60(a), in this embodiment, the sheath insertion section 480 of the defogging sheath device is constructed such that a flange 482 is formed to perpendicularly project inward at the forward end by perpendicularly folding the forward end of a pipe 481 inward or by molding the pipe 481 in one piece. When the flange 482 is formed by folding the pipe 481, as illustrated in FIG. 61(a), one or more notches 483 are arranged for part of the portion to be formed into the flange 482, thereby enhancing an easy folding process.

Figure 60B:
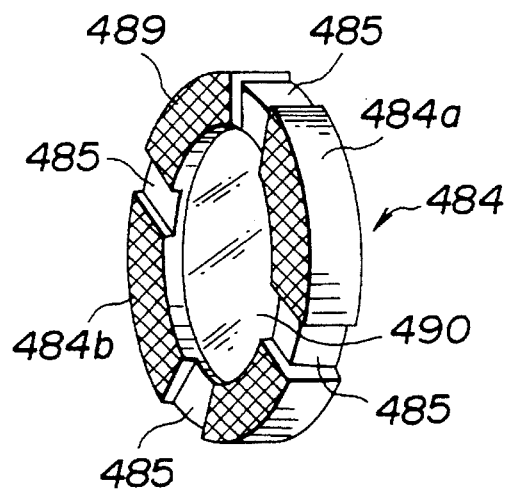

A plate-like transparent cover 484 subjected to a defogging treatment shown in FIG. 60(b) is placed inside the forward end of the sheath insertion section 480. This transparent cover 484 is most preferably placed to be barely in contact with the inner surface of the flange 482.

Figure 61B:
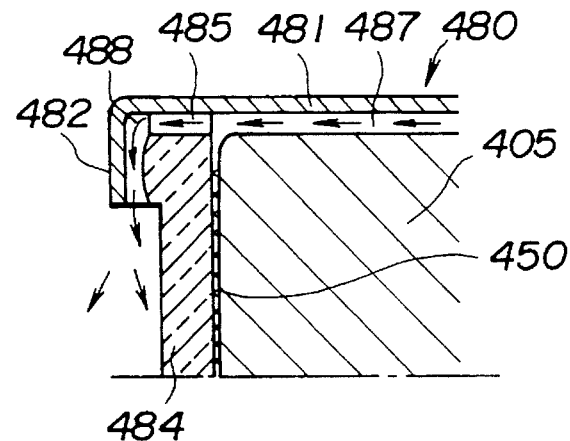

The cover 484 is provided with notch grooves 485 so that it is divided into a plurality of sections each formed of a part of an outer peripheral surface 484a and a part of a forward-end edge 84b which is to be in contact with the inner surface of the flange 482. In this embodiment, the notch grooves 485 are formed in four places, that is, at the top, bottom, right and left of the cover 484. As shown in FIG. 61(b), such notch grooves 485 are combined with the flange 482 so as to form a nozzle 488 which communicates with a passage 487 formed between the inner surface of the pipe 481 constituting the sheath insertion section 480 and the outer peripheral surface of the endoscope insertion section 405.

That is, the cover 484 is constructed such that the surface of the forward-end edge 484b serves the function of a contact surface 489 to be bonded or welded to the flange 482. This contact surface 489 is fixed to the inner surface of the flange 482, thereby forming the nozzle 488 by a space provided by the notch grooves 485. The nozzle 488 may be formed by clamping the cover 484 by means of the flange 482 and the endoscope end surface, instead of by bonding or welding the cover 484 to the flange 482. The forward end of the nozzle 488 is directed perpendicularly to the center axis of the sheath insertion section 480 or directed toward the outer surface of the cover 484.

Transparent compounds, such as a methacrylate resin (PMMA) or a polycarbonate resin (PC), are used for the cover 484, as well as the forward-end member or the transparent plate shown in the foregoing embodiments. Alternatively, the cover 484 may be formed of a transparent member, such as sapphire or glass. Also, the cover 484 may be molded in one piece or produced by attaching a ring-like part having the contact surface 489 and the nozzle notch grooves 483 arranged thereon to a flat separate part having a center portion 490 equivalent to the defogging-treated transparent plate.

The endoscope insertion section 405 is inserted into the sheath insertion section 480 having the defogging-treated cover 484 fit into the forward end thereof. Prior to this insertion, the adhesive 450 has been preferably applied between the end surface of the endoscope insertion section 405 and the cover 484 with a view to enhancing watertightness, stability and other characteristics. With the foregoing construction, the feed water means, or the like, are used to permit a fluid flowing through the passage 487 to pass through the nozzle 488 and to inject toward the outer surface of the cover 484. The fluid remaining on the outer surface of the cover 484 can be removed by the suction or a gas flow through the passage 487 and the nozzle 488, as described above.

As this embodiment is constructed as described above, a cleaning passage and a nozzle can be formed with a simple construction in this embodiment, as well as in the eleventh embodiment.

Figure 62:
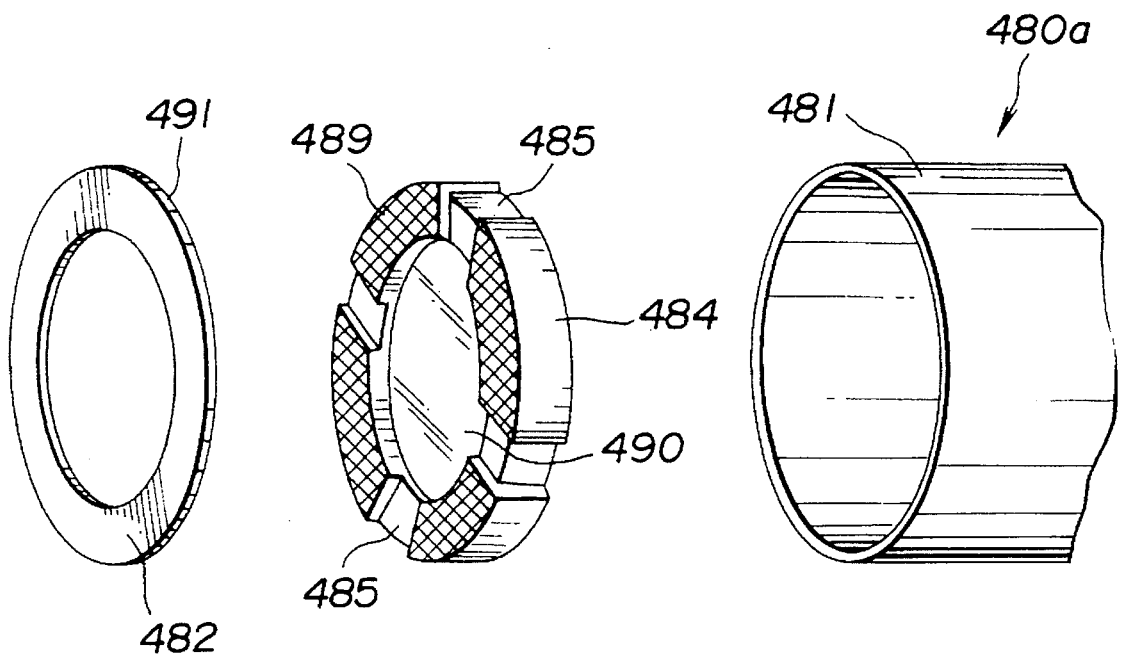
FIG. 62 is a perspective view in which a distal part of an endoscope apparatus according to a first modification of a blur-preventing sheath is developed.

FIG. 62 illustrates a first modification of the defogging sheath insertion section shown in the fourteenth embodiment.

In this first modification, a washer 491 is attached to the forward end of the pipe 481 constituting the sheath insertion section 480a so as to form the flange 482 which has been obtained by folding the forward end of the pipe 481 in the fourteenth embodiment. As in the fourteenth embodiment, the resultant cover 484 is fixed to the inside of the sheath insertion section 480a. Thus, a defogging sheath device similar to that in the fourteenth embodiment can be formed in this modification.

Figure 63:
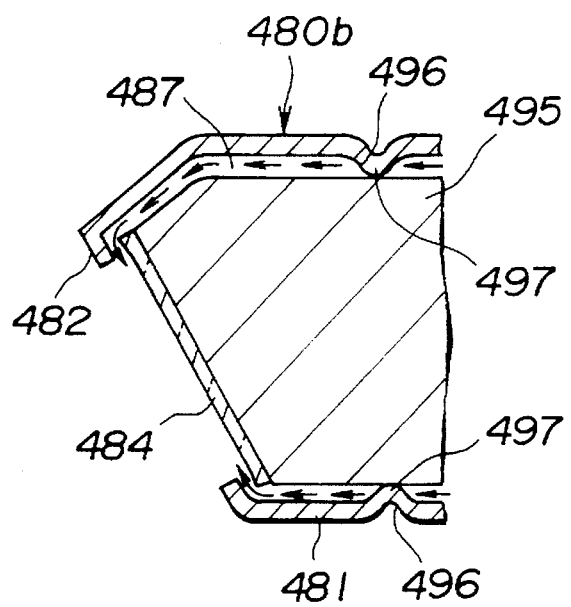
FIG. 63 is a cross-sectional view of a distal part of an endoscope apparatus according to a second modification of the blur-preventing sheath.

FIG. 63 illustrates a second modification of the defogging sheath insertion section shown in the fourteenth embodiment.

In this second modification, the forward end of the pipe 481 constituting the sheath insertion section 480b is obliquely molded with respect to the center axis of the sheath insertion section 480b so that an oblique endoscope insertion section 495 can be attached to the resultant sheath insertion section 480b. Similarly, it is also possible to construct a defogging sheath device compatible for a side-view endoscope by laterally displacing such a sheath device.

Further, in this second modification, a plurality of, for example, three or four recesses 496 projecting inward are arranged to be uniformly spaced on the periphery of the inner surface of the forward end of the pipe 481 constituting the sheath insertion section 480b. Projections 497 of such recesses 496 abut against the outer peripheral surface of the endoscope insertion section 495, thereby positioning the endoscope insertion section 495 in the sheath insertion section 480b.

According to the second modification, a defogging sheath device similar to that shown in the fourteenth embodiment can be constructed compatible for an oblique or side-view endoscope.

As many apparently widely different embodiments of this invention may be made without departing from the spirit and scope thereof, it is to be understood that the invention is not limited to the specific embodiments thereof except as defined in the appended claims.

What is claimed is:

1. An endoscope apparatus comprising:

an endoscope including an insertion section;

a sheath attached thereto covering at least said insertion section of the endoscope, wherein a forward end gap portion is formed between an inner surface of an edge portion formed in a forward end portion of said sheath and an outer surface of a forward end portion of said insertion section of the endoscope, and wherein a fluid passage which communicates with said forward end gap portion is formed between an inner surface of said sheath and an outer surface of said insertion section of the endoscope; and a tubular cleaning channel arranged within said fluid passage for transporting cleaning fluid toward said forward end portion of said insertion section of the endoscope.

2. An endoscope apparatus comprising:

an endoscope including an insertion section;

a sheath attached thereto covering at least said insertion section of the endoscope, wherein an insertion-section gap portion is formed between an inner surface of said sheath and an outer surface of said insertion section of the endoscope, wherein a forward end gap portion which communicates with said insertion-section gap portion is formed between an inner surface of an edge portion formed in a forward end portion of said sheath and an outer surface of a forward end portion of said insertion section of the endoscope, and wherein a fluid passage for passing a cleaning fluid or a sucked object is provided in said insertion-section gap portion;

a tubular cleaning channel arranged within said fluid passage for transporting cleaning fluid toward said forward end portion of said insertion section of said endoscope; and a nozzle section communicating with said tubular cleaning channel for spraying said cleaning fluid onto an observation window portion formed in the forward end portion of said insertion section of the endoscope is provided in said forward end gap portion.

3. An endoscope apparatus according to claim 1, wherein said forward end gap portion includes a jetting port for spraying a cleaning fluid onto an observation window portion formed in the forward end portion of said insertion section of the endoscope.

4. An endoscope apparatus according to claim 1, wherein said sheath is detachably attached to said insertion section of the endoscope, and wherein, when united together, said insertion section of the endoscope and said sheath define said forward end gap portion and said fluid passage.

5. An endoscope apparatus according to claim 1, wherein said fluid passage communicates with a suction means to constitute a suction passage for a sucked object.

6. An endoscope apparatus according to claim 1, wherein said fluid passage communicates with a liquid feeding means to constitute a liquid feeding passage for passing a cleaning fluid.

7. An endoscope apparatus according to claim 1, wherein said fluid passage communicates with a liquid feeding means and a suction means through a flow passage switching means to serve as both a liquid feeding passage for passing a cleaning liquid and a suction passage for passing a sucked object.

8. An endoscope apparatus according to claim 1, further comprising a second sheath covering an outer peripheral surface of the body of said insertion section of the endoscope, wherein said forward end gap portion and said fluid passage are defined between an outer surface of said second sheath and the inner surface of said sheath.

9. An endoscope apparatus according to claim 1, wherein a groove is provided in the inner surface of the edge portion of the forward end portion of said sheath, said forward end gap portion being formed by a space defined between said groove and the outer surface of the forward end portion of said insertion section of the endoscope.

10. An endoscope apparatus according to claim 1, wherein said forward end gap portion has a plurality of openings facing a forward end surface of said insertion section of the endoscope so as to form a plurality of jetting ports for spraying a cleaning fluid onto an observation window portion in the forward end portion of said insertion section of the endoscope.

11. An endoscope apparatus according to claim 1, further comprising a positioning protrusion protruding from the inner surface of said sheath and serving to control the distance between the inner surface of said sheath and the outer surface of said insertion section of the endoscope.

12. An endoscope comprising:

an outer tube covering an insertion section;

an optical unit for observation arranged inside said insertion section;

a gap portion which is formed between an insertion-section body, including said optical unit, and said outer tube and which extends along the axial dimension of said insertion section, wherein a fluid passage for effecting at least one of liquid feeding, suction and air feeding is provided in said gap portion; and a tubular cleaning channel arranged within said fluid passage for transporting cleaning fluid toward said forward end portion of said insertion section of the endoscope.

13. An endoscope apparatus comprising:

an insertion-section body including an observation means;

a covering means for covering said insertion-section body;

a gap portion which is formed between said insertion-section body and an inner surface of said covering means and which extends along the axial dimension of the insertion section, wherein a fluid passage for performing at least one of liquid feeding, suction and air feeding is provided in said gap portion; and a tubular cleaning channel arranged within said fluid passage for transporting cleaning fluid toward said forward end portion of said insertion section of the endoscope.

* * * * *